(12) United States Patent
Stewart et al.

(10) Patent No.: US 10,252,984 B2
(45) Date of Patent: *Apr. 9, 2019

(54) INHIBITING G PROTEIN COUPLED RECEPTOR 6 KINASE POLYPEPTIDES

(71) Applicant: Mayo Foundation for Medical Education and Research, Rochester, MN (US)

(72) Inventors: Alexander Keith Stewart, Scottsdale, AZ (US); Artem Plekhov, Fremont, CA (US); Robert Greenhouse, Newark, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/354,326

(22) PCT Filed: Oct. 26, 2012

(86) PCT No.: PCT/US2012/062206
§ 371 (c)(1),
(2) Date: Apr. 25, 2014

(87) PCT Pub. No.: WO2013/063458
PCT Pub. Date: May 2, 2013

(65) Prior Publication Data
US 2014/0309185 A1    Oct. 16, 2014

Related U.S. Application Data

(60) Provisional application No. 61/552,015, filed on Oct. 27, 2011.

(51) Int. Cl.
| | | |
|---|---|---|
| *C07D 403/10* | (2006.01) |
| *C07D 221/18* | (2006.01) |
| *C07D 237/34* | (2006.01) |
| *C07D 239/70* | (2006.01) |
| *C07D 249/12* | (2006.01) |
| *C07D 285/135* | (2006.01) |
| *C07D 295/13* | (2006.01) |
| *C07D 311/30* | (2006.01) |
| *C07D 311/58* | (2006.01) |
| *C07D 401/08* | (2006.01) |
| *C07D 401/12* | (2006.01) |
| *C07D 403/12* | (2006.01) |
| *C07D 405/12* | (2006.01) |

(Continued)

(52) U.S. Cl.
CPC .......... *C07C 233/65* (2013.01); *A61K 31/352* (2013.01); *A61K 31/4196* (2013.01); *A61K 31/4245* (2013.01); *A61K 31/433* (2013.01); *A61K 31/454* (2013.01); *A61K 31/47* (2013.01); *A61K 31/496* (2013.01); *A61K 31/4985* (2013.01); *A61K 31/506* (2013.01); *A61K 31/5377* (2013.01); *A61K 31/549* (2013.01); *A61K 31/55* (2013.01); *C07D 221/18* (2013.01); *C07D 237/34* (2013.01); *C07D 239/70* (2013.01); *C07D 249/12* (2013.01); *C07D 285/135* (2013.01); *C07D 295/13* (2013.01); *C07D 311/30* (2013.01); *C07D 311/58* (2013.01); *C07D 401/08* (2013.01); *C07D 401/12* (2013.01); *C07D 403/10* (2013.01); *C07D 403/12* (2013.01); *C07D 405/12* (2013.01); *C07D 409/04* (2013.01); *C07D 413/14* (2013.01); *C07D 417/04* (2013.01); *C07D 417/12* (2013.01); *C07D 471/04* (2013.01); *C07D 487/04* (2013.01); *C07D 491/056* (2013.01); *C07H 15/22* (2013.01)

(58) Field of Classification Search
CPC .................. C07D 403/10; C07D 285/135; C07D 249/12; C07D 401/12; C07D 413/14; C07D 401/08; C07D 487/04; C07D 405/12; C07D 403/12; C07D 491/056; C07D 409/04; C07D 311/58; C07D 417/12; C07D 311/30; C07D 417/04; C07D 239/70; C07D 221/18; C07D 471/04; C07D 237/34; C07D 295/13; C07H 15/22; C07C 233/65
USPC ....... 514/255.05, 256, 326, 236.2, 291, 456, 514/300
See application file for complete search history.

(56) References Cited

U.S. PATENT DOCUMENTS 5,463,071 A * 10/1995 Himmelsbach ...... C07D 233/64
544/122
7,226,941 B2   6/2007 Park et al.
(Continued)

FOREIGN PATENT DOCUMENTS

EP          0014810       9/1980
WO    WO2003032916 A2    4/2003
(Continued)

OTHER PUBLICATIONS

14354356 STN search result. See p. 201-203.. Wang et al. Study on the nucleophilic substitution of 3-aryl-5-mercapto-1,2,4-triazoles. Youji Huaxue (1997), 17(6), 535-541. STN search result on Jul. 12, 2015.*

(Continued)

*Primary Examiner* — Yih-Horng Shiao
(74) *Attorney, Agent, or Firm* — Fish & Richardson P.C.

(57) ABSTRACT

This document relates to inhibitors of G protein coupled receptor 6 kinase (GRK6) polypeptides as well as methods and materials for using such inhibitors to treat hematological malignancies, inflammation diseases, and autoimmune disorders.

28 Claims, 29 Drawing Sheets

(51) Int. Cl.

| | |
|---|---|
| C07D 409/04 | (2006.01) |
| C07D 413/14 | (2006.01) |
| C07D 417/04 | (2006.01) |
| C07D 417/12 | (2006.01) |
| C07D 471/04 | (2006.01) |
| C07D 487/04 | (2006.01) |
| C07D 491/056 | (2006.01) |
| C07C 233/65 | (2006.01) |
| C07H 15/22 | (2006.01) |
| A61K 31/4196 | (2006.01) |
| A61K 31/433 | (2006.01) |
| A61K 31/454 | (2006.01) |
| A61K 31/496 | (2006.01) |
| A61K 31/506 | (2006.01) |
| A61K 31/5377 | (2006.01) |
| A61K 31/352 | (2006.01) |
| A61K 31/4245 | (2006.01) |
| A61K 31/47 | (2006.01) |
| A61K 31/4985 | (2006.01) |
| A61K 31/549 | (2006.01) |
| A61K 31/55 | (2006.01) |

(56) References Cited

U.S. PATENT DOCUMENTS

| | | | |
|---|---|---|---|
| 2002/0034767 | A1 | 3/2002 | Benovic et al. |
| 2005/0288347 | A1 | 12/2005 | Hodge et al. |
| 2006/0029983 | A1 | 2/2006 | Oakley et al. |
| 2006/0100235 | A1 | 5/2006 | Andersen et al. |
| 2006/0173006 | A1 | 8/2006 | Sun et al. |
| 2009/0149389 | A1 | 6/2009 | Panitch et al. |
| 2010/0099683 | A1 | 4/2010 | Tomkinson et al. |
| 2011/0139654 | A1 | 6/2011 | Klein et al. |
| 2011/0257211 | A1 | 10/2011 | Chand et al. |
| 2012/0190708 | A1* | 7/2012 | Mackerell et al. ............ 514/301 |
| 2017/0050939 | A1 | 2/2017 | Stewart et al. |
| 2017/0050979 | A1 | 2/2017 | Stewart et al. |

FOREIGN PATENT DOCUMENTS

| | | | |
|---|---|---|---|
| WO | WO2005092873 A2 | | 10/2005 |
| WO | WO2005113788 A2 | | 12/2005 |
| WO | WO 2009/053694 | * | 4/2009 |
| WO | WO 2010/118208 | * | 10/2010 |
| WO | WO 2013/063458 | | 5/2013 |

OTHER PUBLICATIONS

Westwood et al. Identification of arylamine N-acetyltransferase inhibitors as an approach towards novel anti-tuberculars. Protein & Cell 2010, 1(1): 82-95.*

Zareef et al. Synthesis and antimicrobial activity of some derivatives of acylhydrazine including novel benzenediazasulfonamides. ARKIVOC 2008 (ii) 141-152.*

Glossary of medical education terms, Institute of International Medical Education. http://www.iime.org/glossary.htm Accessed in Mar. 2013. (Year: 2013).*

Packiriswamy et al. G-protein-coupled receptor kinases in inflammation and disease. Genes and Immunity (2015) 16, 367-377. Year: 2015).*

Lefevre et al. Fibrinogen is localized on dark zone follicular dendritic cells in vivo and enhances the proliferation and survival of a centroblastic cell line in vitro. J. Leukoc. Biol. 82:666-677; 2007. (Year: 2007).*

Caliper Life Sciences, "Fragment-based screening of enzyme drug targets: Microfluidic mobility shift assay improves confidence in candidate selection." Caliper Life Sciences White Paper (2010).

Matysiak, "QSAR of Antiproliferative Activity of N-Substituted 2-Amino-5-(2,4-dihydroxyphenyl)-1,3,4-thiadiazoles in Various Human Cancer Cells," QSAR & Combinatorial Science, (27)5:607-617, Epub Nov. 13, 2007.

Mazzone et al., "Synthesis and biological evaluation of some 5-aryl-2-amino-1, 3, 4- oxa(thia)diazoles," Farmaco, Edizione Scientifica, 37(10):685-700, 1982 (abstract) [online] Retrieved from STN on the Web, Database CA: 98:100754, compound of the formulae I , I I, compounds with RN 35314-01-3, 83796-35-4.

Mazzone et al., "Synthesis of pharmaceutically significant I-aryl-4H(R)-thiosemicarbazides, the corresponding 5-aryl-4H(R)-1, 2, 4-triazoline-3-thiones and some derivatives," Farmaco, Edizione Scientifica, 36(3):181-196, 1981, (Original in Italian) [English abstract] [on-line] Retrieved from STN on the Web, Database CA: 95:6695, compound of the formula II, compounds with RN 77803-55-5, 77803-57-7.

Pollack et al., "A comparative study of fragment screening methods on the p38a kinase: new methods, new insights," J Comput Aided Mol Des., 25(7):677-687, Epub Jul. 6, 2011.

Puglisi et al., "Antiinflammatory and analgesic activities of 3-(carboxymethylthio)-5-aryl-4-methyl- and -4-phenyl-4H-1, 2, 4-triazoles," Farmaco, Edizione Scientifica, 37(9):633-640, 1982, (Original in Italian) [English abstract] [on-line] Retrieved from STN on the Web, Database CA: 97:207757, compound of the formula I , compound with RN 58755-01-4D.

Stockman et al., "Identification of allosteric PIF-pocket ligands for PDK1 using NMR-based fragment screening and 1H-15N TROSY experiments," Chem Biol Drug Des., 73(2):179-188, Feb. 2009.

Tiedemann et al., "Kinome-wide RNAi studies in human multiple myeloma identify vulnerable kinase targets, including a lymphoid-restricted kinase, GRK6," Blood, 115(8):1594-1604, Epub Dec. 7, 2009.

International Search Report and Written Opinion for PCT/US2012/0622006 dated Mar. 28, 2013, 15 pages.

International Preliminary Report on Patentability for PCT/US2012/062206, dated May 8, 2014, 10 pages.

European Search Report for EP12844282 dated Apr. 14, 2015, 12 pages.

European Search Report for EP12844282 dated Jul. 24, 2015, 22 pages.

European Communication Pursuant to Article 94(3) EPC in Application No. 12844282.9, dated Feb. 20, 2017, 9 pages.

CAS RN 77803-55-5, STN Registry Database, entered STN Nov. 16, 1984, Accessed Jun. 23, 2017.

European Search Report for International Application No. EP15782804.7, dated Aug. 21, 2017, 10 pages.

European Search Report for International Application No. EP15783914.3, dated Aug. 24, 2017, 10 pages.

International Preliminary Report on Patentability in International Application No. PCT/US2015/26926, dated Oct. 25, 2016, 8 pages.

International Search Report and Written Opinion in International Application No. PCT/US2015/26926, dated Oct. 19, 2015, 15 pages.

Invitation to Pay Additional Fees for International Application No. PCT/US2015/26926, dated Aug. 6, 2015, 12 pages.

Karampuri et al., "Structure based molecular design, synthesis and biological evaluation of α-pyrone analogs as anti-HSV agent," *Bioorganic & Medicinal Chemistry Letters*. 22(19):6261-6266, Oct. 2012.

PubChem Compound Summary for CID 43164245, created Jul. 21, 2009.

Extended European Search Report for International Application No. EP15783914.3, dated Nov. 24, 2017, 9 pages.

Extended European Search Report for International Application No. EP15782804.7, dated Nov. 24, 2017, 9 pages.

U.S. Appl. No. 15/305,808, filed Oct. 21, 2016, Pub. No. 20170050979, dated Feb. 23, 2017, Stewart et al.

U.S. Appl. No. 13/305,809, filed Oct. 21, 2016, Pub. No. 20170050939, dated Feb. 23, 2017, Stewart et al.

* cited by examiner

| Structure | IC50 |
|---|---|
| 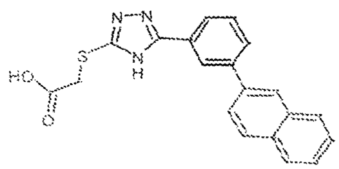 | 0.417 |
| 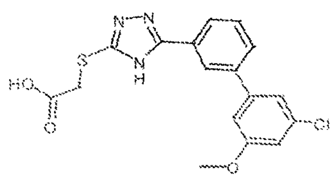 | 0.426 |
| 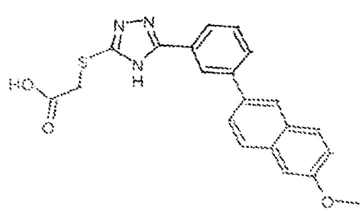 | 0.510 |
| 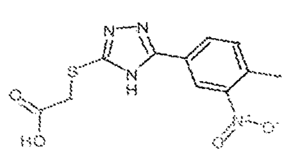 | 0.751 |

| | |
|---|---|
|  | 0.757 |
|  | 0.919 |
|  | 1.050 |
|  | 1.050 |

| Structure | Value |
|---|---|
| 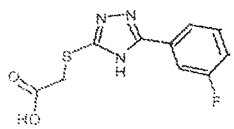 | 4.700 |
| 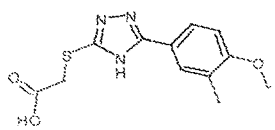 | 4.990 |
| 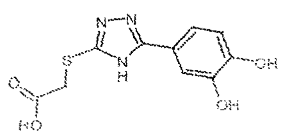 | 5.020 |
| 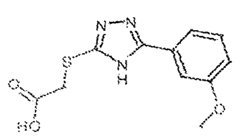 | 5.850 |

FIG. 3 (continued)

| | |
|---|---|
|  | 6.540 |
|  | 6.800 |
|  | 6.880 |
|  | 7.300 |

| | |
|---|---|
|  | 8.750 |
|  | 8.830 |
|  | 8.830 |
|  | 8.840 |

| | |
|---|---|
|  | 9.560 |
|  | 9.900 |
|  | 10.700 |
|  | 11.600 |

|  | 15.900 |
|  | 16.200 |
|  | 17.500 |
|  | 18.300 |

| | |
|---|---|
|  | 18.900 |
|  | 20.700 |
|  | 20.900 |
|  | 21.900 |

| | |
|---|---|
|  | 23.700 |
|  | 25.800 |
|  | 34.800 |
|  | 35.300 |

| | |
|---|---|
| | 40.000 |
| | 45.300 |
| | 51.800 |
| | 74.100 |

| | |
|---|---|
|  | 77.500 |
|  | 81.700 |
|  | 87.000 |
|  | > 100 |

| | |
|---|---|
|  | > 100 |
|  | > 70 |
|  | > 74 |
|  | > 100 |

| | |
|---|---|
|  | > 100 |
|  | > 100 |
|  | > 100 |
|  | > 100 |

| Structure | Value |
|---|---|
| (1-methyl-5-(m-tolyl)-triazole thiopropanoic acid) | > 100 |
| (triazole thio acetic acid with 2-carbamoylphenyl) | > 100 |
| (triazole thio acetic acid with 2-carboxyphenyl) | > 100 |
| (triazole thio acetamide with m-tolyl) | > 100 |

FIG. 3 (continued)

INHIBITING G PROTEIN COUPLED RECEPTOR 6 KINASE POLYPEPTIDES

CROSS-REFERENCE TO RELATED APPLICATIONS

This application is a National Stage application under 35 U.S.C. § 371 of International Application No. PCT/US2012/062206, having an International Filing Date of Oct. 26, 2012, which claims priority to U.S. Provisional Application Ser. No. 61/552,015, filed on Oct. 27, 2011, both of which are incorporated by reference in their entirety herein.

TECHNICAL FIELD

This document relates to inhibitors of G protein coupled receptor 6 kinase (GRK6) polypeptides as well as methods and materials for using such inhibitors to treat hematological malignancies, inflammation diseases, and autoimmune disorders.

BACKGROUND

GRK6 is a member of the enzyme group of kinases. Kinases regulate many different cell proliferation, differentiation, and signaling processes by adding phosphate groups to proteins. The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250-300 amino acid catalytic domain. The N-terminal domain, which contains subdomains I-IV, generally folds into a two-lobed structure, which binds and orients the ATP (or GTP) donor molecule. The larger C terminal lobe, which contains subdomains VI-XI, binds the protein substrate and carries out the transfer of the gamma phosphate from ATP to the hydroxyl group of a serine, threonine, or tyrosine residue. Subdomain V spans the two lobes.

SUMMARY

This document provides inhibitors of G protein couple receptor 6 kinase (GRK6) polypeptides as well as methods and materials for using such inhibitors to treat hematological malignancies, inflammation diseases, and autoimmune disorders. As described herein, an inhibitor of a GRK6 polypeptide provided herein can be used to inhibit activity of a GRK6 polypeptide. For example, the inhibitors provided in Table 1 can be used to inhibit activity of a GRK6 polypeptide. In some cases, a patient afflicted with a disease or disorder characterized by unwanted expression or activity of a GRK6 polypeptide or a polypeptide in a GRK6 signaling pathway can be treated with an inhibitor provided herein (e.g., an inhibitor set forth in Table 1). For example, an inhibitor provided herein can be used to treat hematological malignancies (e.g., B cell cancers such as lymphoma and myeloma) and inflammation diseases (e.g., autoimmune diseases and undesired immune responses).

In some embodiments, an inhibitor provided herein is an inhibitor of Formula (1):

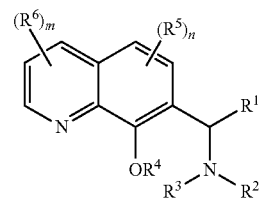

or a pharmaceutically acceptable salt form thereof,
wherein:
$R^1$ is selected from the group consisting of: $(C_3-C_7)$ cycloalkyl, $(C_3-C_7)$heterocycloalkyl, $(C_5-C_{14})$aryl, and $(C_5-C_{14})$heteroaryl;
$R^2$ and $R^3$ are independently selected from the group consisting of: H, $(C_1-C_6)$alkyl, substituted or unsubstituted $(C_3-C_7)$ cycloalkyl, substituted or unsubstituted $(C_3-C_7)$ heterocycloalkyl, substituted or unsubstituted $(C_5-C_{14})$ aryl, and substituted or unsubstituted $(C_5-C_{14})$heteroaryl;
$R^4$ is selected from H and $(C_1-C_6)$alkyl;
each $R^5$ and $R^6$ is independently selected from the group consisting of: H, $(C_1-C_6)$alkyl, halo, —CN, —NR$^7$R$^8$, $(C_1-C_6)$haloalkyl, —O$(C_1-C_6)$haloalkyl, —OR$^7$, and —C(O)R$^7$;
each $R^7$ and $R^8$ is independently selected from the group consisting of: H and $(C_1-C_6)$alkyl;
m is an integer from 0 to 3; and
n is an integer from 0 to 2.

In some embodiments, $R^1$ is a $(C_5-C_{14})$heteroaryl. For example, $R^1$ can be a pyridinyl moiety. In some embodiments, $R^2$ is selected from substituted or unsubstituted $(C_5-C_{14})$aryl and substituted or unsubstituted $(C_5-C_{14})$heteroaryl. For example, $R^2$ can be a pyridinyl moiety or a substituted $(C_5-C_{14})$aryl. In some embodiments, $R^3$ is H. In some embodiments, $R^4$ is H. In some embodiments, m and n are 0.

Non-limiting examples of an inhibitor of Formula (1) include:

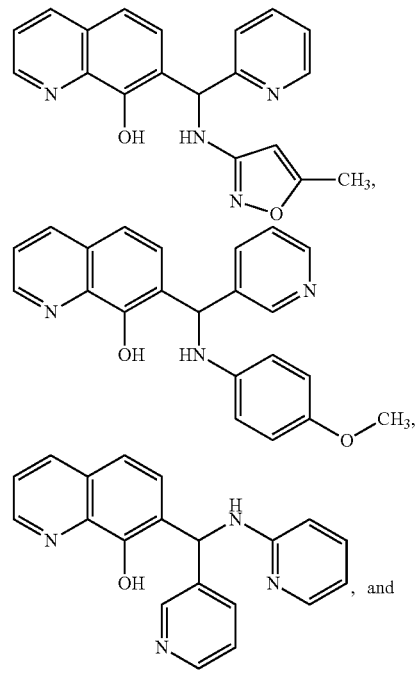

3

-continued

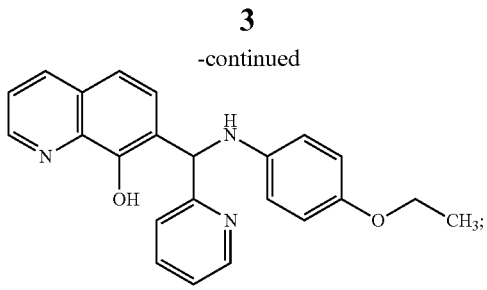

or a pharmaceutically acceptable salt form thereof.

Also provided herein is an inhibitor of Formula (2):

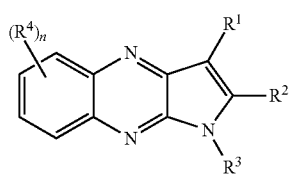

or a pharmaceutically acceptable salt form thereof,
wherein:
$R^1$ is selected from the group consisting of: —C(O)O($C_1$-$C_6$)alkyl) and —CN;
$R^2$ is $NR^5R^6$;
$R^3$ is selected from the group consisting of: ($C_1$-$C_6$)alkyl, ($C_2$-$C_6$)alkenyl, ($C_2$-$C_6$)alkynyl, ($C_3$-$C_7$) cycloalkyl, and ($C_3$-$C_7$)heterocycloalkyl;
$R^4$ is selected from the group consisting of: H, ($C_1$-$C_6$)alkyl, halo, —CN, —$NR^5R^6$, ($C_1$-$C_6$)haloalkyl, —O($C_1$-$C_6$) haloalkyl, —$OR^5$, and —C(O)$R^5$;
each $R^5$ and $R^6$ is independently selected from the group consisting of: H and ($C_1$-$C_6$)alkyl; and
n is an integer from 0 to 4.

In some embodiments, $R^1$ is —C(O)OCH$_3$. In some embodiments, $R^2$ is NH$_2$. In some embodiments, $R^3$ is selected from ($C_1$-$C_6$)alkyl and ($C_3$-$C_7$) cycloalkyl. In some embodiments, n is 0.

Non-limiting examples of an inhibitor of Formula (2) include:

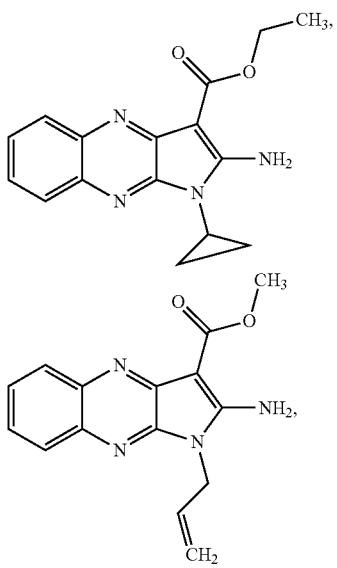

4

-continued

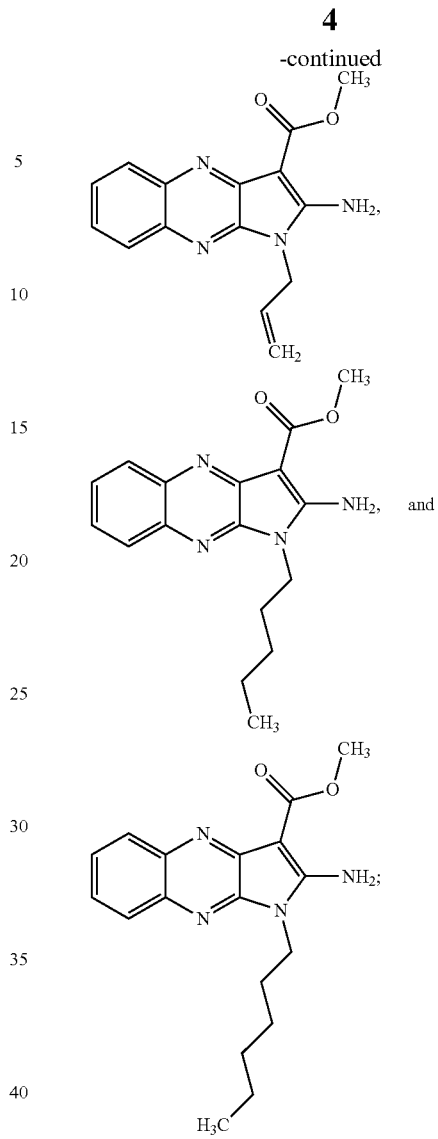

or a pharmaceutically acceptable salt form thereof.

In some embodiments, an inhibitor is provided herein is an inhibitor of Formula (3):

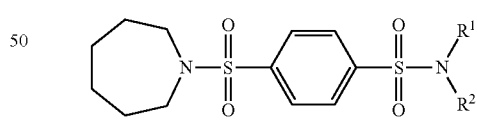

or a pharmaceutically acceptable salt form thereof,
wherein:
$R^1$ and $R^2$ are independently selected from the group consisting of: H, ($C_1$-$C_6$)alkyl, substituted or unsubstituted ($C_3$-$C_7$) cycloalkyl, substituted or unsubstituted ($C_3$-$C_7$) heterocycloalkyl, substituted or unsubstituted ($C_5$-$C_{14}$) aryl, and substituted or unsubstituted ($C_5$-$C_{14}$)heteroaryl.

In some embodiments, $R^1$ is H. In some embodiments, $R^2$ is a substituted ($C_5$-$C_{14}$)aryl.

Non-limiting examples of an inhibitor of Formula (3) include:

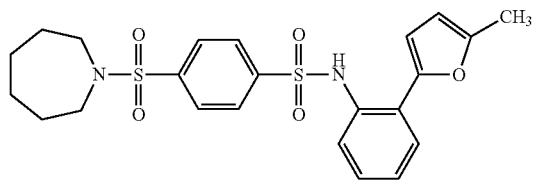

and

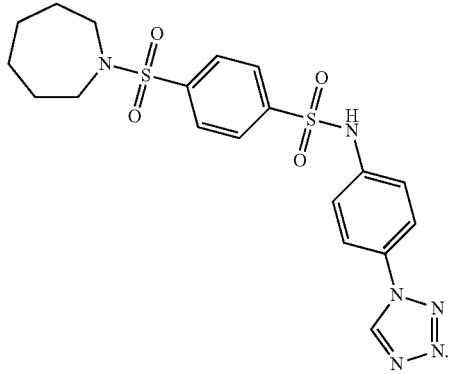

Also provided herein is an inhibitor of Formula (4):

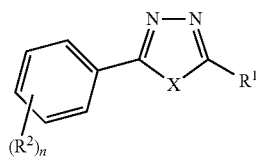

or a pharmaceutically acceptable salt form thereof, wherein:
X is selected from the group consisting of NR$^5$, O, and S;
R$^1$ is selected from the group consisting of: —NR$^3$R$^4$, —S(CH$_2$)$_m$C(O)OR$^3$, —S(CH$_2$)$_m$C(O)NR$^3$R$^4$;
each R$^2$ is independently selected from the group consisting of: H, (C$_1$-C$_6$)alkyl, halo, (C$_1$-C$_6$)haloalkyl, —CN, —NR$^3$R$^4$, —NO$_2$, —O(C$_1$-C$_6$)haloalkyl, —OR$^3$, —OC(O)R$^3$, —C(O)R$^3$, —C(O)OR$^3$, —C(O)NR$^3$R$^4$, —SR$^3$, —SO$_2$R$^3$, —SO$_2$NR$^3$R$^4$, (C$_3$-C$_7$) cycloalkyl, (C$_3$-C$_7$)heterocycloalkyl, (C$_5$-C$_{14}$)aryl, and (C$_5$-C$_{14}$)heteroaryl;
R$^3$ and R$^4$ are independently selected from the group consisting of: H, (C$_1$-C$_6$)alkyl, (C$_3$-C$_7$) cycloalkyl, (C$_3$-C$_7$) heterocycloalkyl, (C$_5$-C$_{14}$)aryl, and (C$_5$-C$_{14}$)heteroaryl;
R$^5$ is selected from the group consisting of: H and (C$_1$-C$_6$) alkyl;
m is an integer from 1 to 5; and
n is an integer from 1 to 5.

In some embodiments, an inhibitor of Formula (4) is an inhibitor of Formula (4-1):

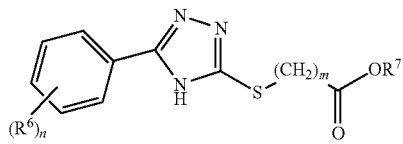

or a pharmaceutically acceptable salt form thereof, wherein:
R$^3$ and R$^4$ are independently selected from the group consisting of: H, (C$_1$-C$_6$)alkyl, (C$_3$-C$_7$) cycloalkyl, (C$_3$-C$_7$) heterocycloalkyl, (C$_5$-C$_{14}$)aryl, and (C$_5$-C$_{14}$)heteroaryl;

R$^6$ is independently selected from the group consisting of H, (C$_1$-C$_6$)alkyl, halo, (C$_1$-C$_6$)haloalkyl, —CN, —NR$^3$R$^4$, —NO$_2$, —O(C$_1$-C$_6$)haloalkyl, —OR$^3$, —OC(O)R$^3$, —C(O)R$^3$, —C(O)OR$^3$, —C(O)NR$^3$R$^4$, —SR$^3$, —SO$_2$R$^3$, —SO$_2$NR$^3$R$^4$, (C$_3$-C$_7$) cycloalkyl, (C$_3$-C$_7$)heterocycloalkyl, (C$_5$-C$_{14}$)aryl, and (C$_5$-C$_{14}$)heteroaryl;
R$^7$ is selected from the group consisting of: H and (C$_1$-C$_6$) alkyl;
m is an integer from 1 to 2; and
n is an integer from 1 to 3.

In some embodiments, R$^6$ is selected from the group consisting of: (C$_1$-C$_6$)alkyl, —OR$^3$, —O(C$_1$-C$_6$)haloalkyl, and (C$_5$-C$_{14}$)heteroaryl. In some embodiments, R$^7$ is H.

Non-limiting examples of an inhibitor of Formula (4) include:

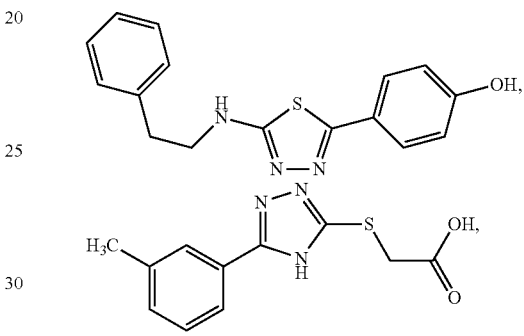

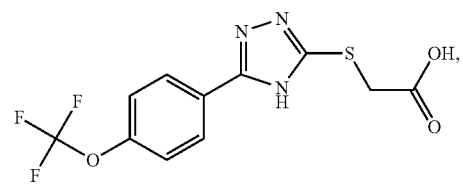

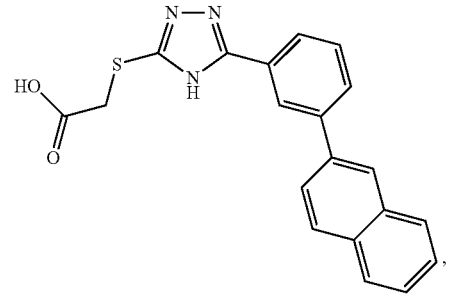

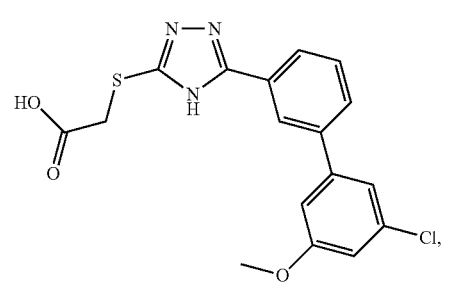

-continued
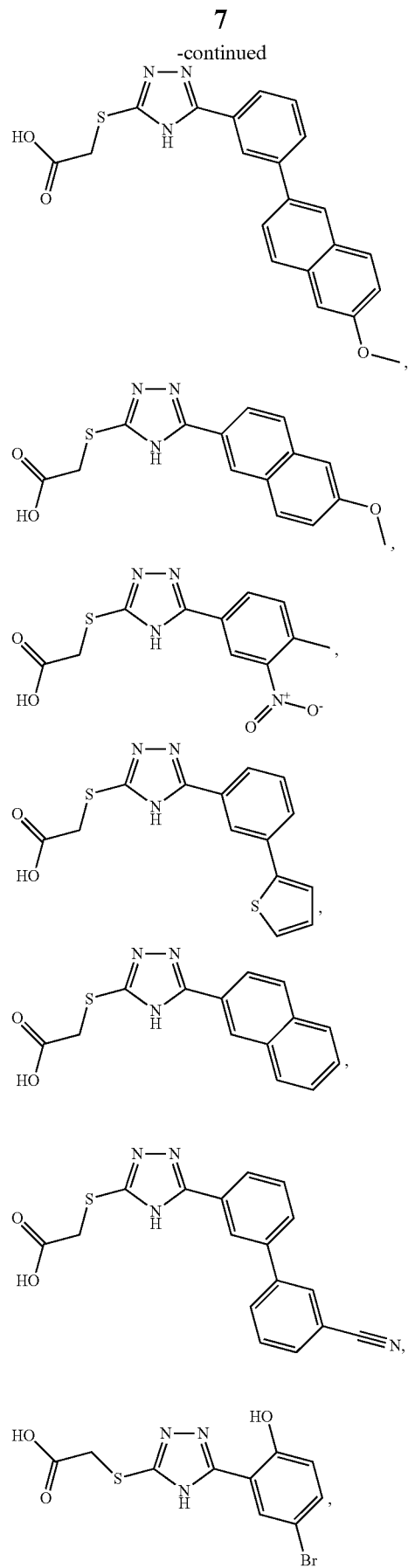
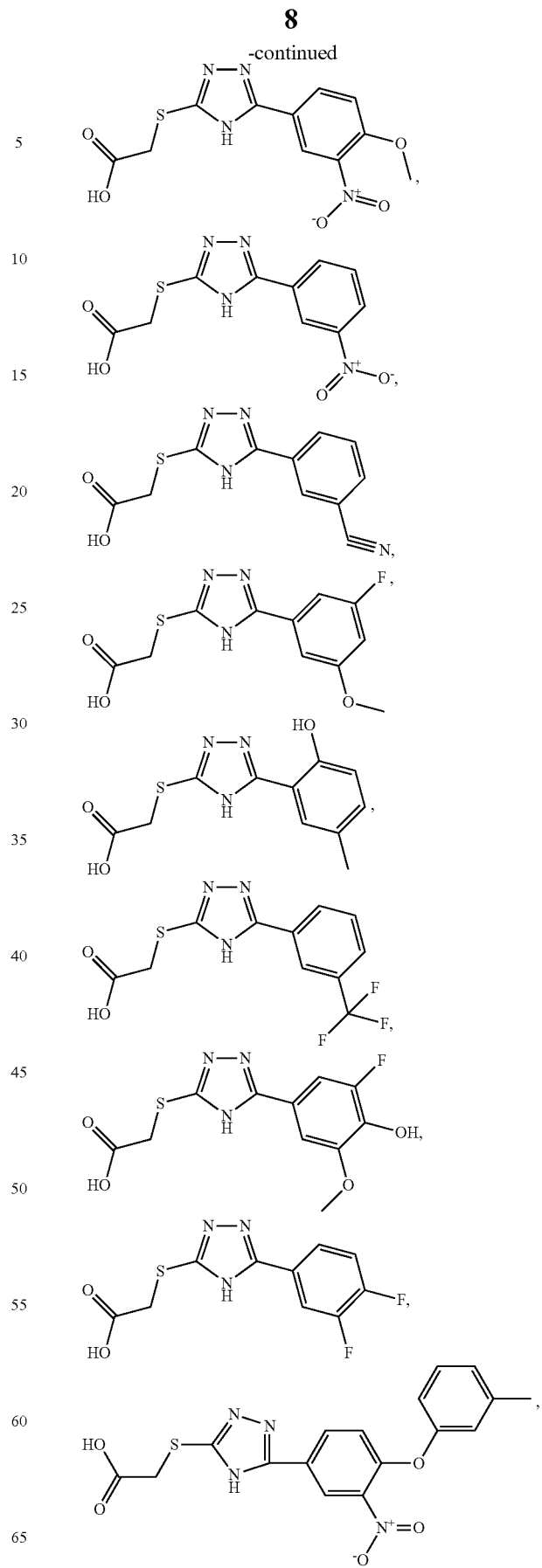

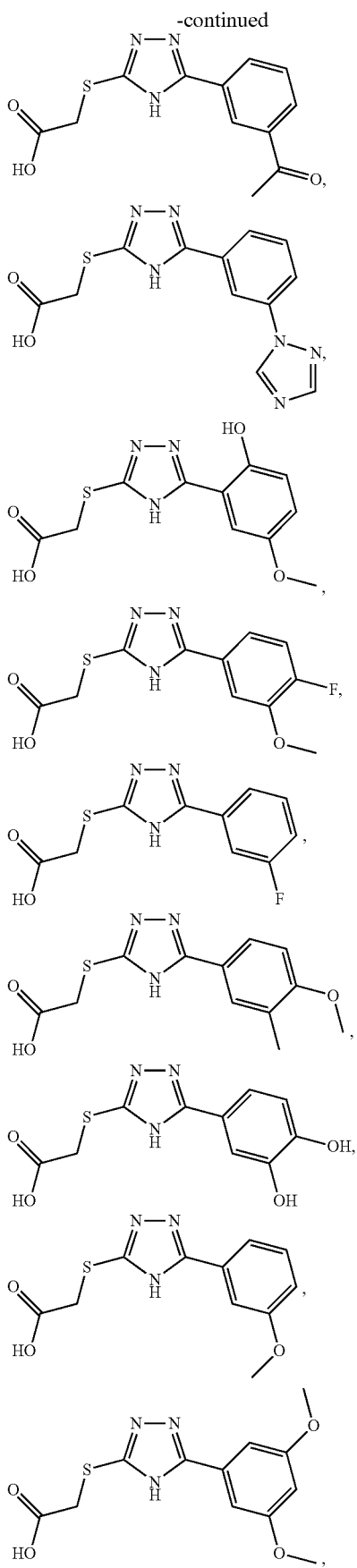

-continued
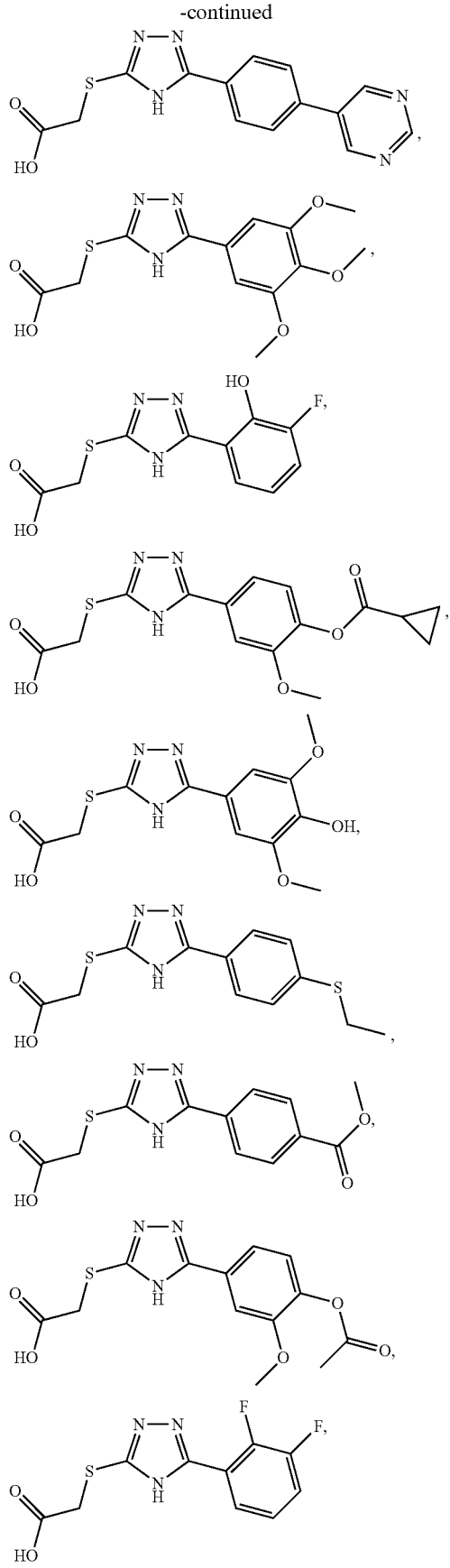
-continued
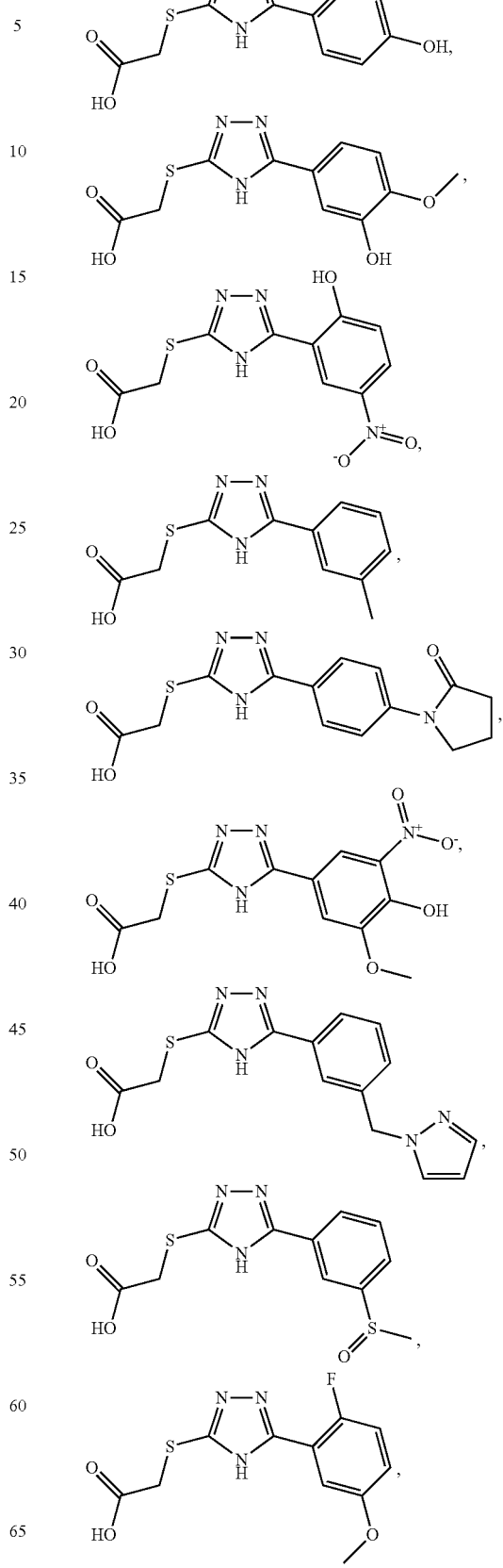

13
-continued
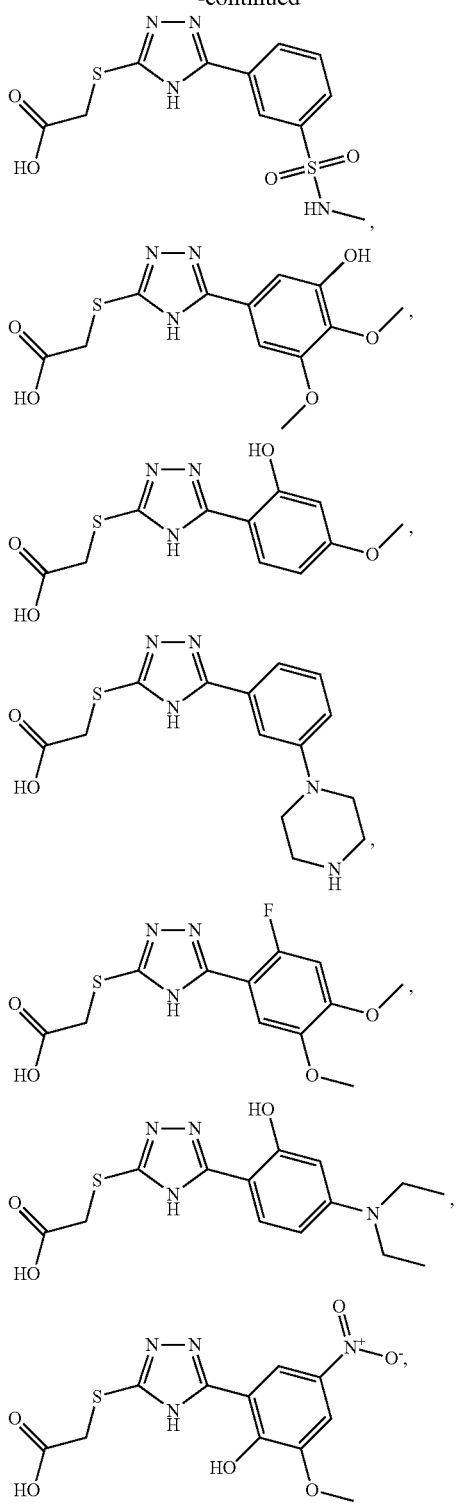
14
-continued
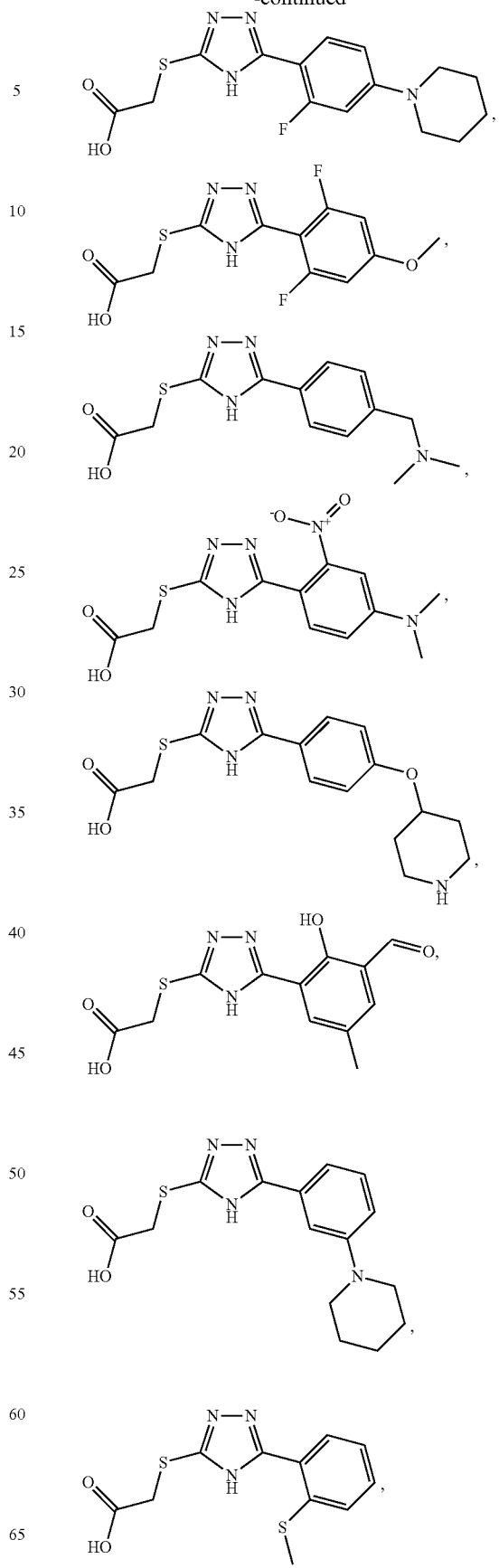

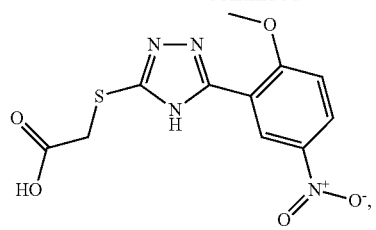
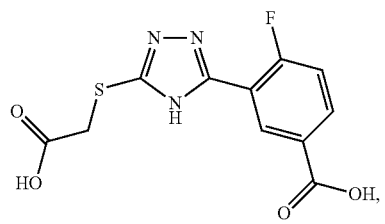
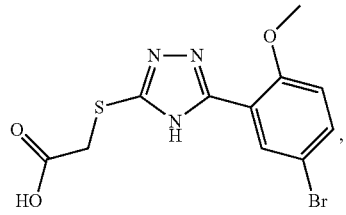
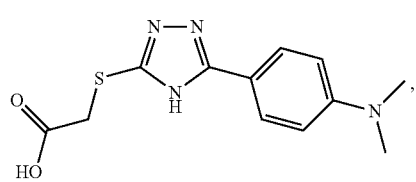
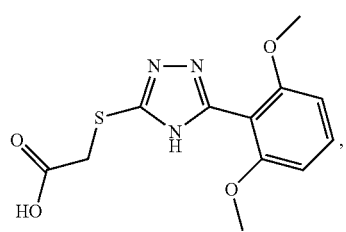
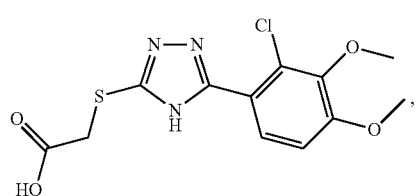
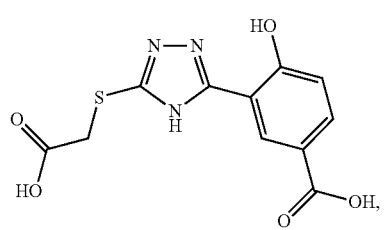
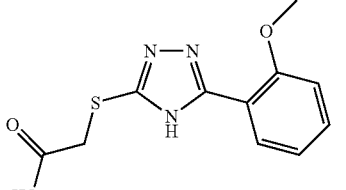
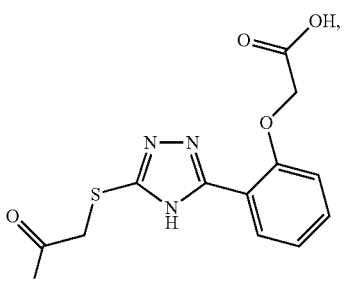
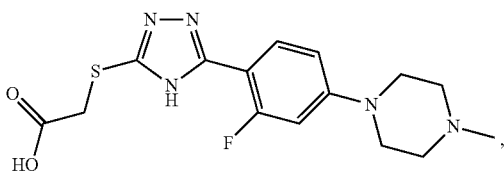
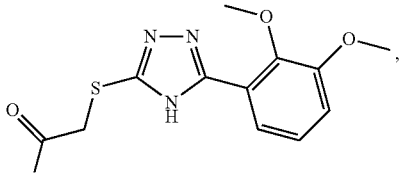
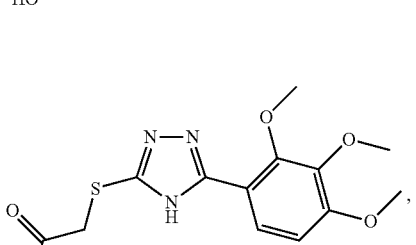
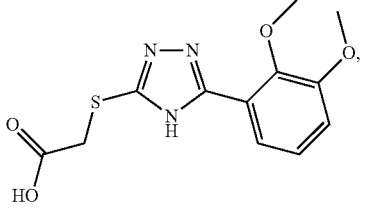

-continued
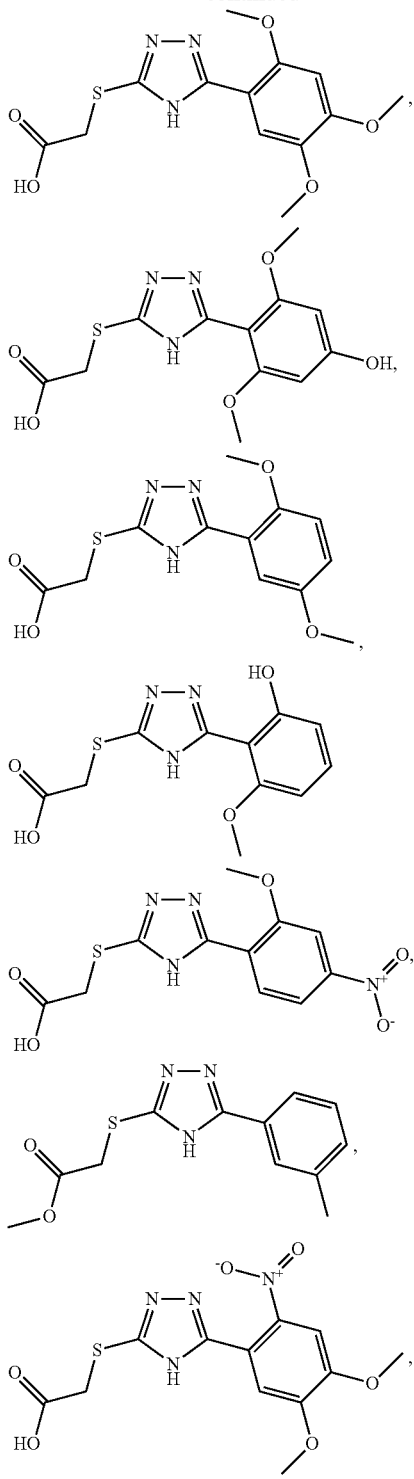
-continued
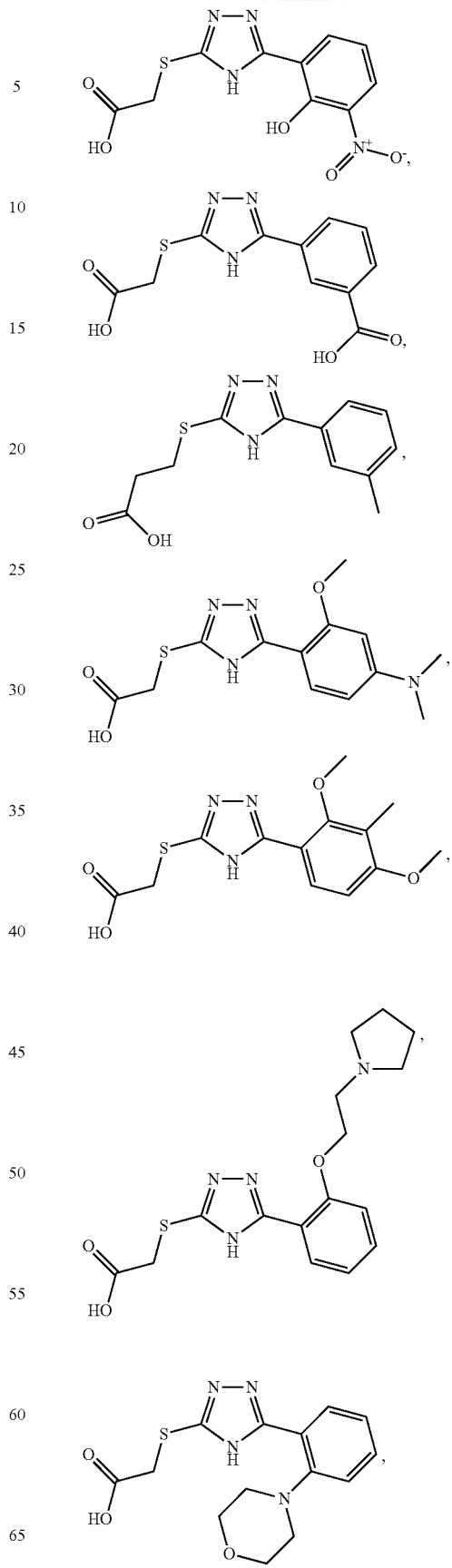

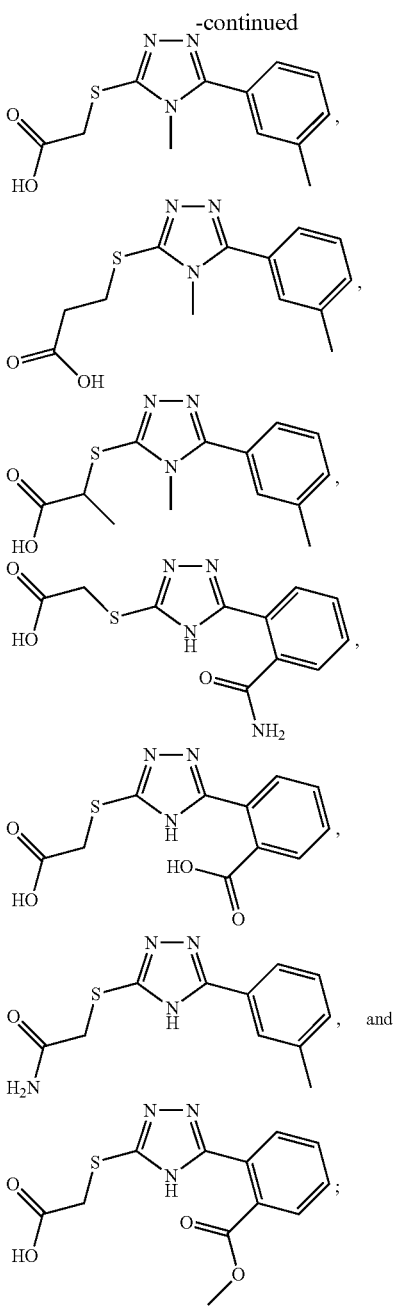

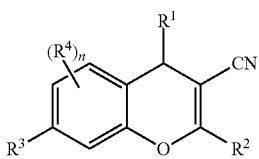

or a pharmaceutically acceptable salt form thereof.

In some embodiments, an inhibitor provided herein is an inhibitor of Formula (5):

tuted $(C_3-C_7)$heterocycloalkyl, substituted or unsubstituted $(C_5-C_{14})$aryl, and substituted or unsubstituted $(C_5-C_{14})$heteroaryl;

$R^2$ is $NR^5R^6$;

$R^3$ is $NR^5R^6$ each $R^4$ is independently selected from the group consisting of: H, $(C_1-C_6)$alkyl, substituted or unsubstituted $(C_3-C_7)$cycloalkyl, substituted or unsubstituted $(C_3-C_7)$heterocycloalkyl, substituted or unsubstituted $(C_5-C_{14})$aryl, and substituted or unsubstituted $(C_5-C_{14})$heteroaryl;

each $R^5$ and $R^6$ is independently selected from the group consisting of: H and $(C_1-C_6)$alkyl; and n is an integer from 0 to 2.

In some embodiments, $R^1$ is selected from substituted or unsubstituted $(C_5-C_{14})$aryl, and substituted or unsubstituted $(C_5-C_{14})$heteroaryl. In some embodiments, $R^2$ is $NH_2$. In some embodiments, $R^3$ is $NH_2$. In some embodiments, n is 0.

Non-limiting examples of an inhibitor of Formula (5) include:

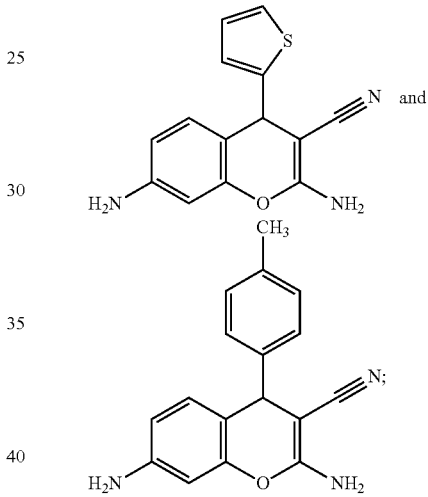

or a pharmaceutically acceptable salt form thereof.

Also provided herein is an inhibitor of Formula (6):

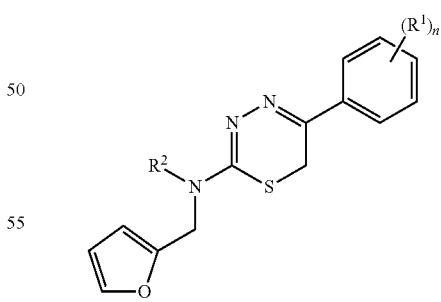

or a pharmaceutically acceptable salt form thereof, wherein:

$R^1$ is selected from the group consisting of: H, $(C_1-C_6)$alkyl, halo, —CN, —$NR^3R^4$, —$NO_2$, $(C_1-C_6)$haloalkyl, —O$(C_1-C_6)$haloalkyl, —$OR^3$, and —C(O)$R^3$, $(C_3-C_7)$cycloalkyl, $(C_3-C_7)$heterocycloalkyl, $(C_5-C_{14})$aryl, and $(C_5-C_{14})$heteroaryl;

$R^2$ is selected from H and $(C_1-C_6)$alkyl;

each R³ and R⁴ is independently selected from the group consisting of: H and $(C_1$-$C_6)$alkyl; and n is an integer from 0 to 5.

In some embodiments, R¹ is selected from H, halo, —NO₂, and $(C_5$-$C_{14})$aryl. In some embodiments, R² is H.

Non-limiting examples of an inhibitor of Formula (6) is selected from the group consisting of:

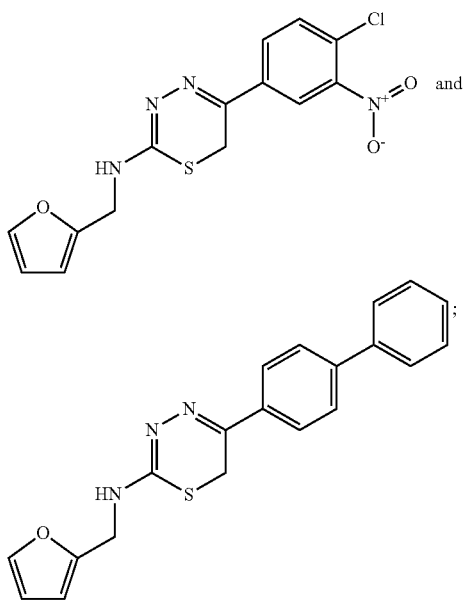

or a pharmaceutically acceptable salt form thereof.

In some embodiments, an inhibitor provided herein is an inhibitor of Formula (7):

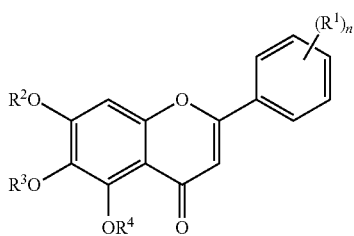

or a pharmaceutically acceptable salt form thereof, wherein:

each R¹ is independently selected from the group consisting of: H, $(C_1$-$C_6)$alkyl, halo, —CN, —NR⁵R⁶, $(C_1$-$C_6)$haloalkyl, —O$(C_1$-$C_6)$haloalkyl, —OR⁵, and —C(O)R⁵;

R², R³, and R⁴ are independently selected from H and $(C_1$-$C_6)$alkyl;

each R⁵ and R⁶ is independently selected from the group consisting of: H and $(C_1$-$C_6)$alkyl; and n is an integer from 0 to 5.

In some embodiments, R¹ is selected form H and —OR⁵. For example, R¹ can be —OH. In some embodiments, R², R³, and R⁴ are H.

Non-limiting examples of an inhibitor of Formula (7) includes:

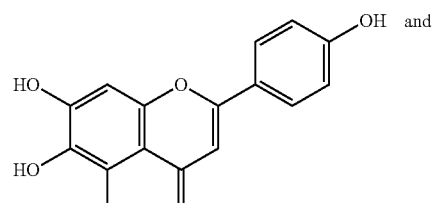

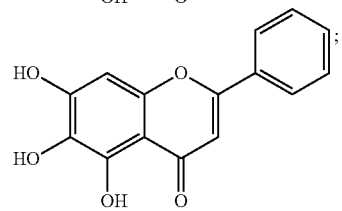

or a pharmaceutically acceptable salt form thereof.

Also provided herein is an inhibitor selected from the group consisting of:

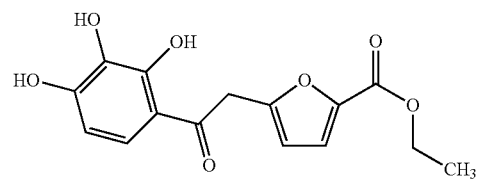

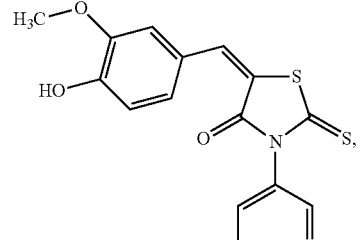

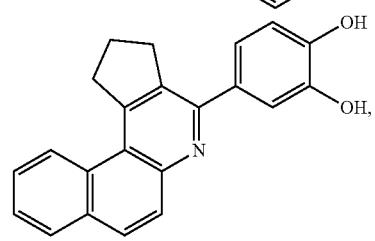

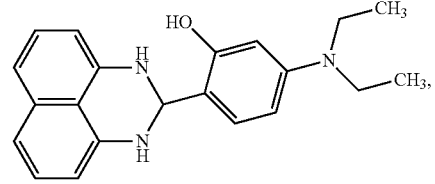

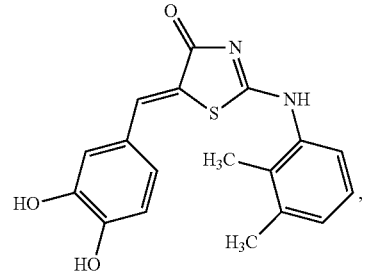

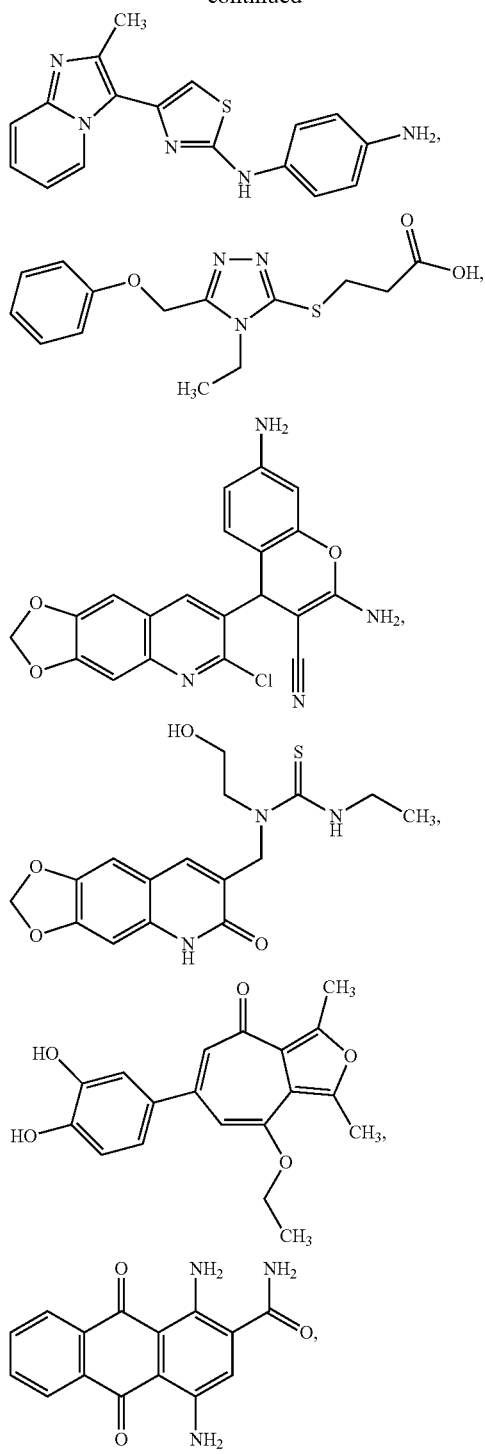
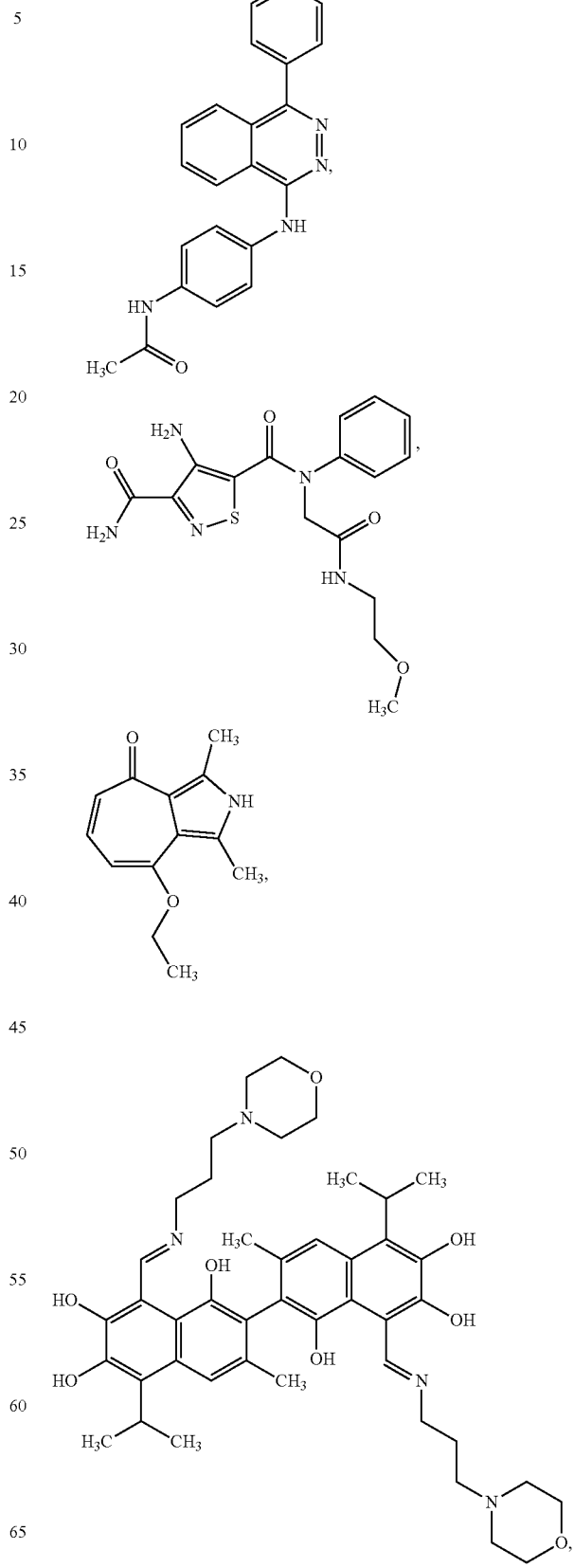

25
-continued
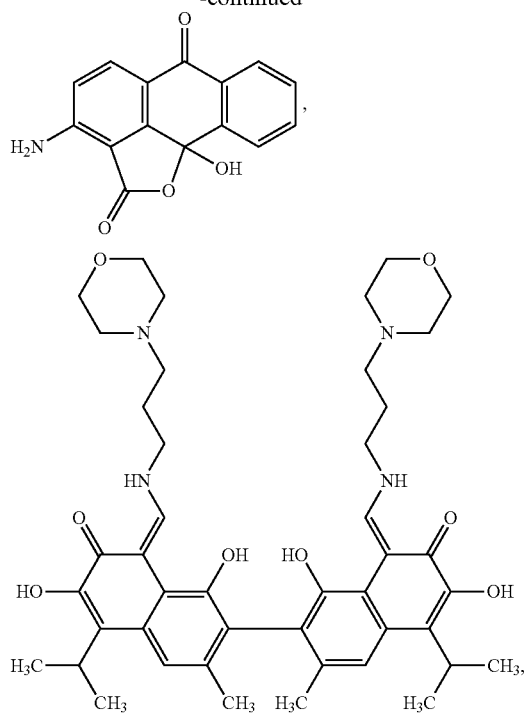
26
-continued
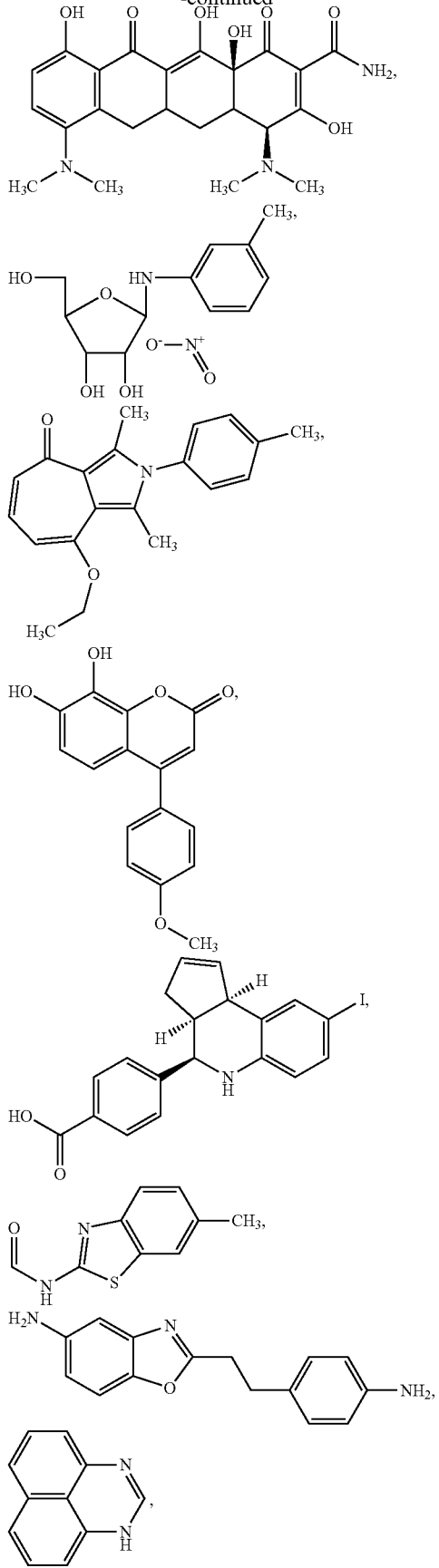

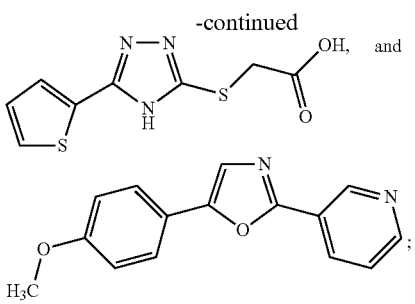

or a pharmaceutically acceptable salt form thereof.

Provided herein is a method for inhibiting a G protein coupled receptor 6 kinase polypeptide in a patient, the method comprising administering to the patient a therapeutically effective amount of an inhibitor provided herein.

Also provided herein is a method for inhibiting a G protein coupled receptor 6 kinase polypeptide in a cell, the method comprising contacting the cell with an effective amount of an inhibitor as provided herein. In some embodiments, the cell is a cancerous cell. For example, the cancerous cell can be a B cell cancerous cell.

Further provided herein is a method for treating a hematological malignancy in a patient, the method comprising administering to the patient a therapeutically effective amount of an inhibitor as provided herein. In some embodiments, the hematological malignancy is a B cell cancer. For example, the B cell cancer can be selected from the group consisting of: a small lymphocytic lymphoma (SLL), a mantle cell lymphoma, a Burkitt's lymphoma, a follicle centre cell lymphoma, a follicular lymphoma, a Burkitt-like lymphoma, a marginal zone B-cell lymphoma (MZBCL), a nodal marginal zone B cell lymphoma, an extra-nodal marginal zone B cell lymphoma, a splenic marginal zone B cell lymphoma, a lymphoplasmacytic lymphoma, and a diffuse large B cell lymphoma. In some embodiments, the B cell cancer is selected from the group consisting of: a B cell acute lymphocytic leukemia (B-ALL), a precursor B cell acute lymphocytic leukemia (B-ALL), a B cell chronic lymphocytic leukemia (B-CLL), a precursor B-lymphoblastic leukaemia, a precursor B-lymphoblastic lymphoma, a small lymphocytic lymphoma, a B cell prolymphocytic leukemia, an undifferentiated B cell lymphoma, a hairy cell leukemia, a mediastinal large B-cell lymphoma, a plasma cell myeloma, a plasmacytoma, a primary effusive lymphoma, a Burkitt's cell leukemia, and a B cell diffuse mixed lymphoma.

Provided herein is a method for treating an inflammation disease in a patient, the method comprising administering to the patient a therapeutically effective amount of an inhibitor as provided herein. In some embodiments, the inflammatory disease is selected from the group consisting of: encephalitis, inflammatory eye disease, otitis, pharyngitis, pneumonia, gastritis, enteritis, hepatitis, pancreatitis, nephritis, cystitis, urethritis, endometritis, vaginitis, arthritis, peripheral neuritis, malignant tumor, infectious diseases, autoimmune diseases, ischemic diseases, metabolic diseases, injury, scald, chemical corrosion, and neurodegenerative diseases. For example, an autoimmune diseases can be selected from the group consisting of: rheumatism, systemic lupus erythematosus, and sarcoidosis. In some embodiments, an ischemic disease is selected from the group consisting of: myocardial infarction and cerebral infarction. In some embodiments, a metabolic disease is selected from the group consisting of: diabetes and gout. In some embodiments, a neurodegenerative disease is Alzheimer's.

Also provided herein is a method of suppressing an immune response in a patient, the method comprising administering to the patient a therapeutically effective amount of an inhibitor as provided herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
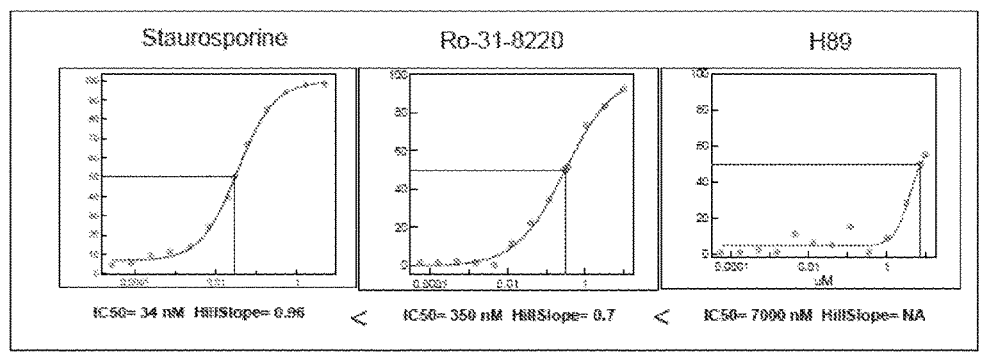
FIG. 1 is a set of concentration—response curves indicating inhibition of a GRK6 polypeptide prepared using identified inhibitors of a GRK6 polypeptide.

This document provides inhibitors of G protein couple receptor 6 kinase (GRK6) polypeptides as well as methods and materials for using such inhibitors to treat hematological malignancies, inflammation diseases, and autoimmune disorders. As described herein, an inhibitor of a GRK6 polypeptide provided herein can be used to inhibit activity of a GRK6 polypeptide. For example, the inhibitors provided in Table 1 can be used to inhibit activity of a GRK6 polypeptide. In some cases, a patient afflicted with a disease or disorder characterized by unwanted expression or activity of a GRK6 polypeptide or a polypeptide in a GRK6 signaling pathway can be treated with an inhibitor provided herein (e.g., an inhibitor set forth in Table 1). For example, an inhibitor provided herein can be used to treat hematological malignancies (e.g., B cell cancers such as lymphoma and myeloma) and inflammation diseases (e.g., autoimmune diseases and undesired immune responses).

Definitions

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

A "therapeutically effective" amount of the inhibitors described herein is typically one which is sufficient to achieve the desired effect and may vary according to the nature and severity of the disease condition, and the potency of the inhibitor. It will be appreciated that different concentrations may be employed for prophylaxis than for treatment of an active disease.

The term "contacting" means bringing at least two moieties together, whether in an in vitro system or an in vivo system.

The term "inhibition" with respect to a GRK6 polypeptide refers to inhibition of a GRK6 polypeptide and its biological activities associated with a GRK6 polypeptide pathway. Inhibition of GRK6 polypeptide can include antagonizing or inactivation. The mode of action of a GRK6 polypeptide inhibitor can be direct, e.g., through binding to a GRK6 polypeptide as a ligand. An inhibitor also can be indirect, e.g., through binding to and/or modifying another molecule that otherwise binds to and activates a GRK6 polypeptide.

As used herein, "administration" refers to delivery of an inhibitor or composition comprising an inhibitor provided herein by any external route, including, without limitation, IV, intramuscular, SC, intranasal, inhalation, transdermal, oral, buccal, rectal, sublingual, and parenteral administration.

The term "cancerous B cell" is used herein to refer to a B cell that is cancerous. By "cancerous cell" or "cancer cell" is meant a cell that shows aberrant cell growth, such as increased cell growth. A cancerous cell may be a hyperplastic cell, a cell that shows a lack of contact inhibition of growth in vitro, a tumor cell that is incapable of metastasis in vivo, or a metastatic cell that is capable of metastasis in vivo.

An inhibitor provided herein can also incorporate one or more isotopes of the atoms occurring in the inhibitor. Isotopes include, for example, those atoms having the same atomic number but different mass numbers. For example, carbon atoms can include carbon-12, carbon-13, and/or carbon-14 and hydrogen atoms can include hydrogen, deuterium, and/or tritium.

The term, "inhibitor," as used herein is meant to include all stereoisomers, geometric isomers, and tautomers of the structures depicted. Inhibitors herein identified by name or structure as one particular tautomeric form are intended to include other tautomeric forms unless otherwise specified.

In some embodiments, an inhibitor provided herein, or salt thereof, is substantially isolated. By "substantially isolated" is meant that the inhibitor is at least partially or substantially separated from the environment in which it was formed or detected. Partial separation can include, for example, a composition enriched in the inhibitor provided herein. Substantial separation can include compositions containing at least about 50%, at least about 60%, at least about 70%, at least about 80%, at least about 90%, at least about 95%, at least about 97%, or at least about 99% by weight of the inhibitors provided herein, or salt thereof. Methods for isolating inhibitors and their salts are routine in the art.

The phrase "pharmaceutically acceptable" is used herein to refer to those inhibitors, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "alkyl" includes a substituted or unsubstituted straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_{1-6}$ for straight chain; $C_{3-6}$ for branched chain). The term $C_{1-6}$ includes alkyl groups containing 1 to 6 carbon atoms.

The term "alkenyl" includes a substituted or unsubstituted aliphatic groups that may or may not be substituted, as described above for alkyls, containing at least one double bond and at least two carbon atoms. For example, the term "alkenyl" includes straight-chain alkenyl groups (e.g., ethylenyl, propenyl, butenyl, pentenyl, hexenyl, heptenyl, octenyl, nonenyl, and decenyl) and branched-chain alkenyl groups. In certain embodiments, a straight chain or branched chain alkenyl group has six or fewer carbon atoms in its backbone (e.g., $C_{2-6}$ for straight chain; $C_{3-6}$ for branched chain). The term $C_{2-6}$ includes alkenyl groups containing 2 to 6 carbon atoms.

The term "alkynyl" includes a substituted or unsubstituted unsaturated aliphatic group analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has six or fewer carbon atoms in its backbone (e.g., $C_{2-6}$ for straight chain; $C_{3-6}$ for branched chain). The term $C_{2-6}$ includes alkynyl groups containing 2 to 6 carbon atoms.

The term "cycloalkyl" includes a substituted or unsubstituted cyclic aliphatic group which may be saturated or unsaturated. For example, cycloalkyl groups include cyclopropyl, cyclopentyl, cyclohexyl, cycloheptyl, and cyclooctyl. In some embodiments, cycloalkyls can have from 3-8 carbon atoms in their ring structure, for example, they can have 3, 4, 5, or 6 carbons in the ring structure.

In general, the term "aryl" includes substituted or unsubstituted groups, including 5- and 6-membered single-ring aromatic groups, such as benzene and phenyl.

Furthermore, the term "aryl" includes multicyclic aryl groups, e.g., tricyclic, bicyclic, such as naphthalene and anthracene.

The term "heteroaryl" includes substituted or unsubstituted groups, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes substituted or unsubstituted groups, including but not limited to, 3- to 10-membered single or multiple rings having one to five heteroatoms, for example, piperazine, pyrrolidine, piperidine, or homopiperazine.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring. Non-limiting examples of substitutents include: $(C_1-C_6)$alkyl, halo, $(C_1-C_6)$haloalkyl, —CN, —NR$^8$R$^9$, —NO$_2$, —O($C_1-C_6$)haloalkyl, —OR$^8$, —OC(O)R$^8$, —C(O)R$^8$, —C(O)OR$^8$, —C(O)NR$^8$R$^9$, —SR$^8$, —S(O)R$^8$, —SO$_2$R$^8$, —SO$_2$NR$^8$R$^9$, $(C_3-C_7)$ cycloalkyl, $(C_3-C_7)$heterocycloalkyl, $(C_5-C_{14})$aryl, and $(C_5-C_{14})$heteroaryl, wherein R$^8$ and R$^9$ are independently selected from H and $(C_1-C_6)$alkyl.

Inhibitors

This document provides inhibitors of GRK6 polypeptides as well as methods and materials for using such inhibitors to treat hematological malignancies, inflammation diseases, and autoimmune disorders.

A. Inhibitors of Formula (1)

In some cases, the inhibitors provided herein can be an inhibitor having the formula set forth in Formula (1):

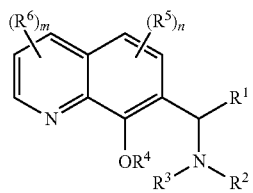

or a pharmaceutically acceptable salt form thereof,
wherein:
R$^1$ is selected from the group consisting of: $(C_3-C_7)$ cycloalkyl, $(C_3-C_7)$heterocycloalkyl, $(C_5-C_{14})$aryl, and $(C_5-C_{14})$heteroaryl;
R$^2$ and R$^3$ are independently selected from the group consisting of: H, $(C_1-C_6)$alkyl, substituted or unsubstituted $(C_3-C_7)$ cycloalkyl, substituted or unsubstituted $(C_3-C_7)$ heterocycloalkyl, substituted or unsubstituted $(C_5-C_{14})$ aryl, and substituted or unsubstituted $(C_5-C_{14})$heteroaryl;
R$^4$ is selected from H and $(C_1-C_6)$alkyl;
each R$^5$ and R$^6$ is independently selected from the group consisting of: H, $(C_1-C_6)$alkyl, halo, —$(C_1-C_6)$haloalkyl, —CN, —NR$^7$R$^8$, —O($C_1-C_6$)haloalkyl, —OR$^7$, and —C(O)R$^7$;
each R$^7$ and R$^8$ is independently selected from the group consisting of: H and $(C_1-C_6)$alkyl;

m is an integer from 0 to 3; and
n is an integer from 0 to 2.

In some embodiments, R$^1$ is a $(C_5-C_{14})$heteroaryl. For example, R$^1$ can be a pyridinyl moiety. In some embodiments, R$^2$ is selected from substituted or unsubstituted $(C_5-C_{14})$aryl and substituted or unsubstituted $(C_5-C_{14})$heteroaryl. For example, R$^2$ can be a pyridinyl or a methylisoxazolyl moiety or a substituted $(C_5-C_{14})$aryl such as an ethoxybenzyl moiety. In some embodiments, R$^3$ is H. In some embodiments, R$^4$ is H. In some embodiments, m and n are 0.

Non-limiting examples of an inhibitor of Formula (1) include:

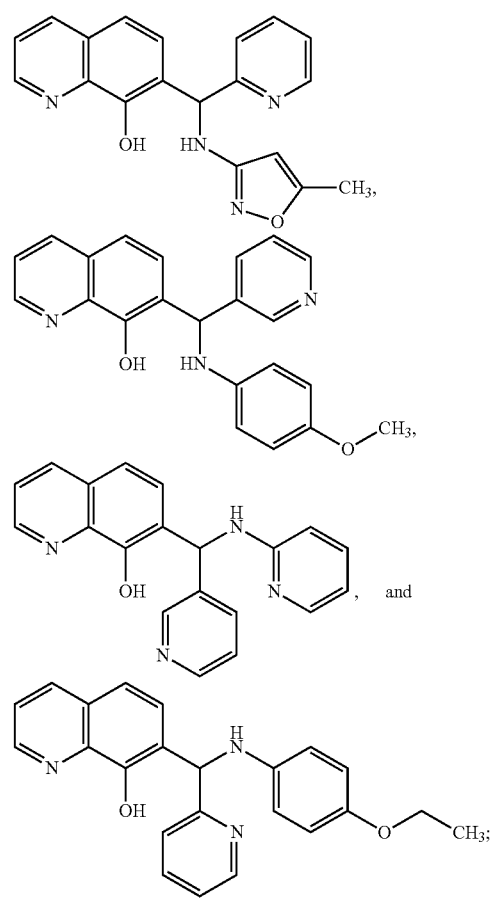

or a pharmaceutically acceptable salt form thereof.

B. Inhibitors of Formula (2)

In some cases, the inhibitors provided herein can be an inhibitor having the formula set forth in Formula (2):

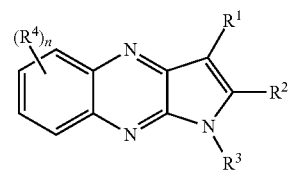

or a pharmaceutically acceptable salt form thereof,
wherein:
R$^1$ is selected from the group consisting of: —C(O)O($C_1$-$C_6$)alkyl and —CN;

$R^2$ is $NR^5R^6$;

$R^3$ is selected from the group consisting of: $(C_1\text{-}C_6)$alkyl, $(C_2\text{-}C_6)$alkenyl, $(C_2\text{-}C_6)$alkynyl, $(C_3\text{-}C_7)$ cycloalkyl, and $(C_3\text{-}C_7)$heterocycloalkyl;

$R^4$ is selected from the group consisting of: H, $(C_1\text{-}C_6)$alkyl, halo, —CN, —$NR^5R^6$, $(C_1\text{-}C_6)$haloalkyl, —$O(C_1\text{-}C_6)$ haloalkyl, —$OR^5$, and —$C(O)R^5$;

each $R^5$ and $R^6$ is independently selected from the group consisting of: H and $(C_1\text{-}C_6)$alkyl; and n is an integer from 0 to 4.

In some embodiments, $R^1$ is selected from —$C(O)OCH_3$ and —$C(O)OCH_2CH_3$. In some embodiments, $R^2$ is $NH_2$. In some embodiments, $R^3$ is selected from $(C_1\text{-}C_6)$alkyl and $(C_3\text{-}C_7)$ cycloalkyl. For example, $R^3$ can be cyclopropyl. In some embodiments, n is 0.

Non-limiting examples of an inhibitor of Formula (2) include:

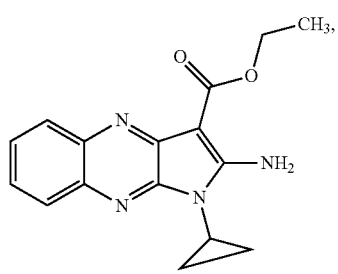

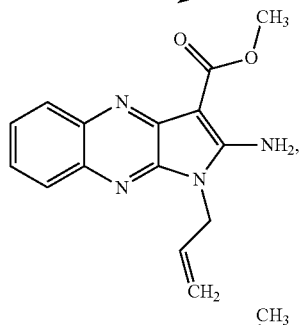

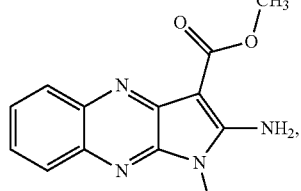

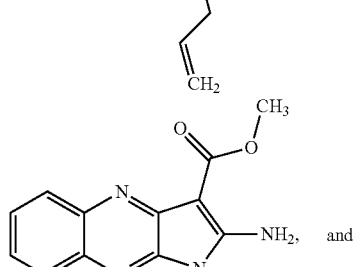

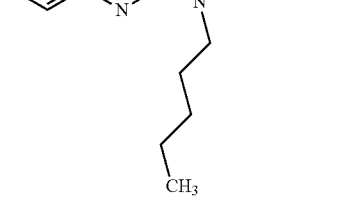

-continued

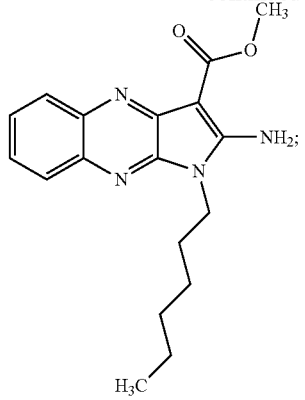

or a pharmaceutically acceptable salt form thereof.

C. Inhibitors of Formula (3)

In some cases, the inhibitors provided herein can be an inhibitor having the formula set forth in Formula (3):

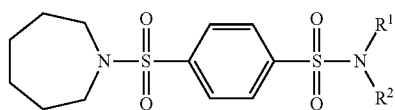

or a pharmaceutically acceptable salt form thereof,
wherein:

$R^1$ and $R^2$ are independently selected from the group consisting of: H, $(C_1\text{-}C_6)$alkyl, substituted or unsubstituted $(C_3\text{-}C_7)$ cycloalkyl, substituted or unsubstituted $(C_3\text{-}C_7)$ heterocycloalkyl, substituted or unsubstituted $(C_5\text{-}C_{14})$ aryl, and substituted or unsubstituted $(C_5\text{-}C_{14})$heteroaryl.

In some embodiments, $R^1$ is H. In some embodiments, $R^2$ is a substituted $(C_5\text{-}C_{14})$aryl. For example, $R^2$ is a substituted $C_6$ aryl moiety such as methyl(phenylfuranyl) and phenyl(tetrazolyl).

Non-limiting examples of an inhibitor of Formula (3) include:

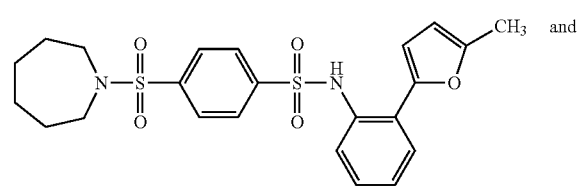

and

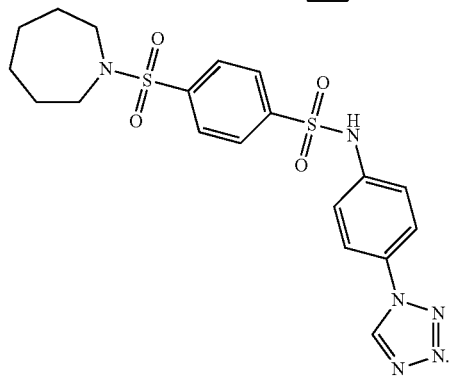

D. Inhibitor of Formula (4)

In some cases, the inhibitors provided herein can be an inhibitor having the formula set forth in Formula (4):

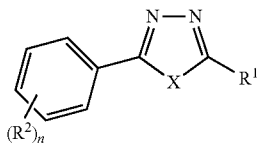

or a pharmaceutically acceptable salt form thereof, wherein:

X is selected from the group consisting of $NR^5$, O, and S;
$R^1$ is selected from the group consisting of: $-NR^3R^4$, $-S(CH_2)_mC(O)OR^3$, $-S(CH_2)_mC(O)NR^3R^4$;
each $R^2$ is independently selected from the group consisting of: H, $(C_1-C_6)$alkyl, halo, $(C_1-C_{16})$haloalkyl, $-CN$, $-NR^3R^4$, $-NO_2$, $-O(C_1-C_6)$haloalkyl, $-OR^3$, $-OC(O)R^3$, $-C(O)R^3$, $-C(O)OR^3$, $-C(O)NR^3R^4$, $-SR^3$, $-S(O)R^3$, $-SO_2R^3$, $-SO_2NR^3R^4$, $(C_3-C_7)$ cycloalkyl, $(C_3-C_7)$ heterocycloalkyl, $(C_5-C_{14})$aryl, and $(C_5-C_{14})$heteroaryl;
each $R^3$ and $R^4$ are independently selected from the group consisting of: H, $(C_1-C_6)$alkyl, $(C_3-C_7)$ cycloalkyl, $(C_3-C_7)$ heterocycloalkyl, $(C_5-C_{14})$aryl, and $(C_5-C_{14})$heteroaryl;
$R^5$ is selected from the group consisting of: H and $(C_1-C_6)$ alkyl;
m is an integer from 1 to 5; and
n is an integer from 1 to 5.

In some embodiments, X is NH.

In some embodiments, $R^1$ is $-S(CH_2)_mC(O)OR^3$. In certain of such embodiments,
m is 1 or 2. In some embodiments, $R^1$ is $-S(CH_2)C(O)OH$.

In some embodiments, $R^2$ is selected from the group consisting of: $(C_1-C_6)$alkyl, halo, $(C_1-C_6)$haloalkyl, $-CN$, $-NO_2$, $-OR^3$, $-OC(O)R^3$, $-OC(O)R^3$, $-C(O)R^3$, $-C(O)OR^3$, $-SR^3$, $-SO_2R^3$, $-SO_2NR^3R^4$, $(C_5-C_{14})$aryl, and $(C_5-C_{14})$heteroaryl. For example, $R^2$ can be selected from the group consisting of: $(C_1-C_6)$alkyl, halo, $(C_1-C_6)$ haloalkyl, $-CN$, $-NO_2$, $-OR^3$, $-C(O)R^3$, $(C_5-C_{14})$aryl, and $(C_5-C_{14})$heteroaryl. In certain of these embodiments, n is an integer from 1 to 3 (e.g., 1, 2 or 3). In some cases, n is 1. In certain of these embodiments, each $R^3$ is independently selected from the group consisting of: H, $(C_1-C_6)$alkyl, $(C_3-C_7)$ cycloalkyl, and $(C_5-C_{14})$aryl. For example, $R^3$ can be methyl, cyclopropyl, or a substituted or unsubstituted phenyl group. In some of these embodiments, $R^4$ is H.

In some embodiments, each $R^3$ is independently selected from the group consisting of: H, $(C_1-C_6)$alkyl, $(C_3-C_7)$ cycloalkyl, and $(C_5-C_{14})$aryl. For example, each $R^3$ can be independently H or $(C_1-C_6)$alkyl. In some embodiments, $R^3$ is methyl. In some embodiments, $R^3$ is H. In some embodiments, each $R^4$ is independently H or $(C_1-C_6)$alkyl.

In some embodiments, n is an integer from 1 to 3. In some embodiments, n is 1 or 2. In some embodiments, m is 1 or 2.

In some embodiments, X is NH; $R^1$ is $-S(CH_2)_mC(O)OR^3$; $R^2$ is selected from the group consisting of: $(C_1-C_6)$ alkyl, halo, $(C_1-C_6)$haloalkyl, $-CN$, $-NO_2$, $-OR^3$, $-OC(O)R^3$, $-OC(O)R^3$, $-C(O)R^3$, $-C(O)OR^3$, $-SR^3$, $-SO_2R^3$, $-SO_2NR^3R^4$, $(C_5-C_{14})$aryl, and $(C_5-C_{14})$heteroaryl; each $R^3$ is independently selected from the group consisting of: H, $(C_1-C_6)$alkyl, $(C_3-C_7)$ cycloalkyl, and $(C_5-C_{14})$aryl; each $R^4$ is independently H or $(C_1-C_6)$alkyl; n is an integer from 1 to 3; and m is 1 or 2.

In some embodiments, X is NH; $R^1$ is $-S(CH_2)C(O)OH$; $R^2$ is selected from the group consisting of: $(C_1-C_6)$alkyl, halo, $(C_1-C_6)$haloalkyl, $-CN$, $-NO_2$, $-OR^3$, $-C(O)R^3$, $(C_5-C_{14})$aryl, and $(C_5-C_{14})$heteroaryl; each $R^3$ is independently selected from the group consisting of: H, $(C_1-C_6)$ alkyl, $(C_3-C_7)$ cycloalkyl, and $(C_5-C_{14})$aryl; and each $R^4$ is independently H or $(C_1-C_6)$alkyl; n is an integer from 1 to 3; and m is 1 or 2.

An inhibitor of Formula (4) can include inhibitors of Formula (4-1):

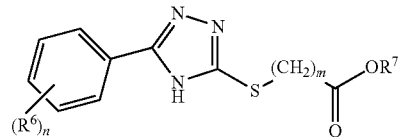

or a pharmaceutically acceptable salt form thereof, wherein:

$R^3$ and $R^4$ are independently selected from the group consisting of: H, $(C_1-C_6)$alkyl, $(C_3-C_7)$ cycloalkyl, $(C_3-C_7)$ heterocycloalkyl, $(C_5-C_{14})$aryl, and $(C_5-C_{14})$heteroaryl;
$R^6$ is independently selected from the group consisting of H, $(C_1-C_6)$alkyl, halo, $(C_1-C_6)$haloalkyl, $-CN$, $-NR^3R^4$, $-NO_2$, $-O(C_1-C_6)$haloalkyl, $-OR^3$, $-OC(O)R^3$, $-C(O)R^3$, $-C(O)OR^3$, $-C(O)NR^3R^4$, $-SR^3$, $-SO_2R^3$, $-SO_2NR^3R^4$, $(C_3-C_7)$ cycloalkyl, $(C_3-C_7)$heterocycloalkyl, $(C_5-C_{14})$aryl, and $(C_5-C_{14})$heteroaryl;
$R^7$ is selected from the group consisting of: H and $(C_1-C_6)$ alkyl;
m is an integer from 1 to 2; and
n is an integer from 1 to 3.

In some embodiments, $R^6$ is selected from the group consisting of: $(C_1-C_6)$alkyl, $-O(C_1-C_6)$haloalkyl, $-OR^3$, and $(C_5-C_{14})$heteroaryl. For example, $R^6$ can be $-CH_3$, $-OH$, and $-OCF_3$. In some embodiments, $R^7$ is H.

In some embodiments, $R^6$ is selected from the group consisting of: $(C_1-C_6)$alkyl, halo, $(C_1-C_6)$haloalkyl, $-CN$, $-NO_2$, $-OR^3$, $-OC(O)R^3$, $-OC(O)R^3$, $-C(O)R^3$, $-C(O)OR^3$, $-SR^3$, $-SO_2R^3$, $-SO_2NR^3R^4$, $(C_5-C_{14})$aryl, and $(C_5-C_{14})$heteroaryl. For example, $R^2$ can be selected from the group consisting of: $(C_1-C_6)$alkyl, halo, $(C_1-C_6)$ haloalkyl, $-CN$, $-NO_2$, $-OR^3$, $-C(O)R^3$, $(C_5-C_{14})$aryl, and $(C_5-C_{14})$heteroaryl. In certain of these embodiments, n is an integer from 1 to 2 (e.g., n is 1 or 2). In some cases, n is 1. In certain of these embodiments, each $R^3$ is independently selected from the group consisting of: H, $(C_1-C_6)$ alkyl, $(C_3-C_7)$ cycloalkyl, and $(C_5-C_{14})$aryl. For example, $R^3$ can be methyl, cyclopropyl, or a substituted or unsubstituted phenyl group. In some of these embodiments, $R^4$ is H.

In some embodiments, each $R^3$ is independently selected from the group consisting of: H, $(C_1-C_6)$alkyl, $(C_3-C_7)$ cycloalkyl, and $(C_5-C_{14})$aryl. For example, each $R^3$ can be independently H or $(C_1-C_6)$alkyl. In some embodiments, $R^3$ is methyl. In some embodiments, $R^3$ is H. In some embodiments, each $R^4$ is independently H or $(C_1-C_6)$alkyl.

In some embodiments, n is 1 or 2.

In some embodiments, $R^6$ is selected from the group consisting of: $(C_1-C_6)$alkyl, halo, $(C_1-C_6)$haloalkyl, $-CN$, $-NO_2$, $-OR^3$, $-OC(O)R^3$, $-OC(O)R^3$, $-C(O)R^3$, $-C(O)OR^3$, $-SR^3$, $-SO_2R^3$, $-SO_2NR^3R^4$, $(C_5-C_{14})$aryl, and $(C_5-C_{14})$heteroaryl; each $R^3$ is independently selected from the group consisting of: H, $(C_1-C_6)$alkyl, $(C_3-C_7)$ cycloalkyl, and $(C_5-C_{14})$aryl; each $R^4$ is independently H or $(C_1-C_6)$alkyl; n is an integer from 1 to 3; and m is 1 or 2.

Non-limiting examples of a Formula (4) include:
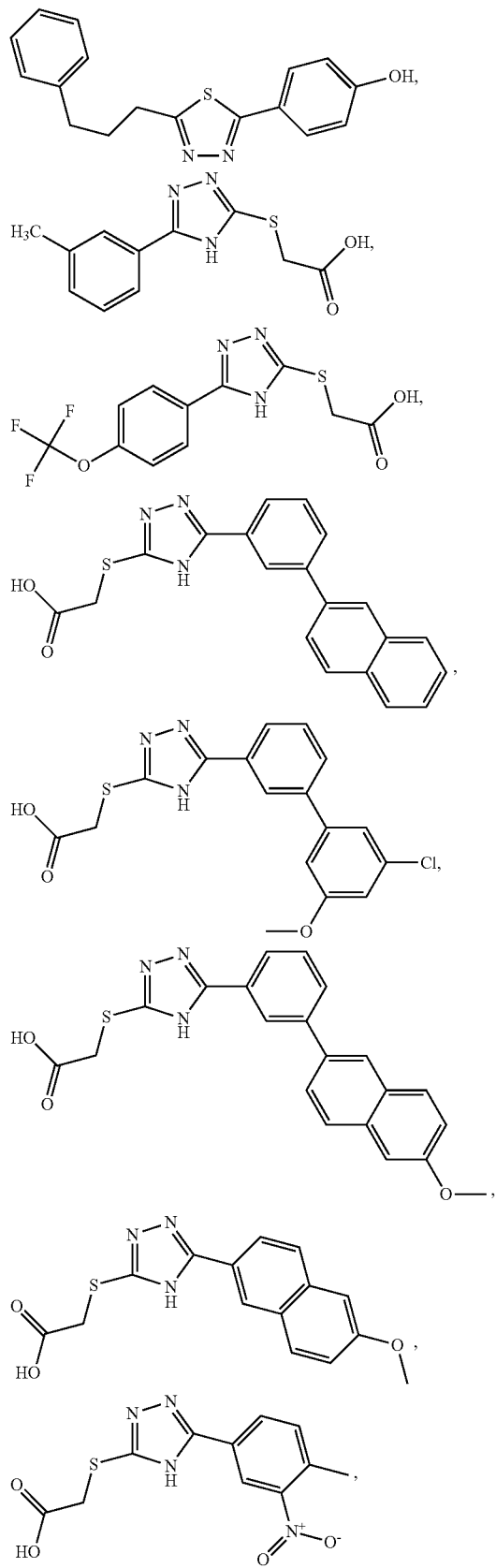
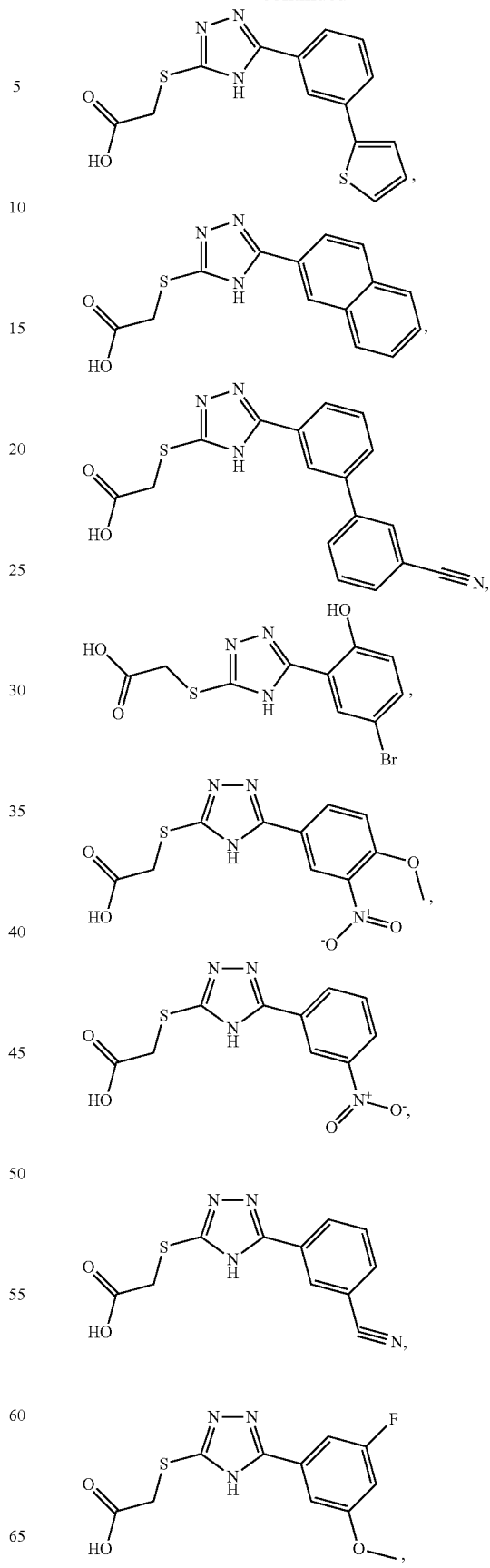

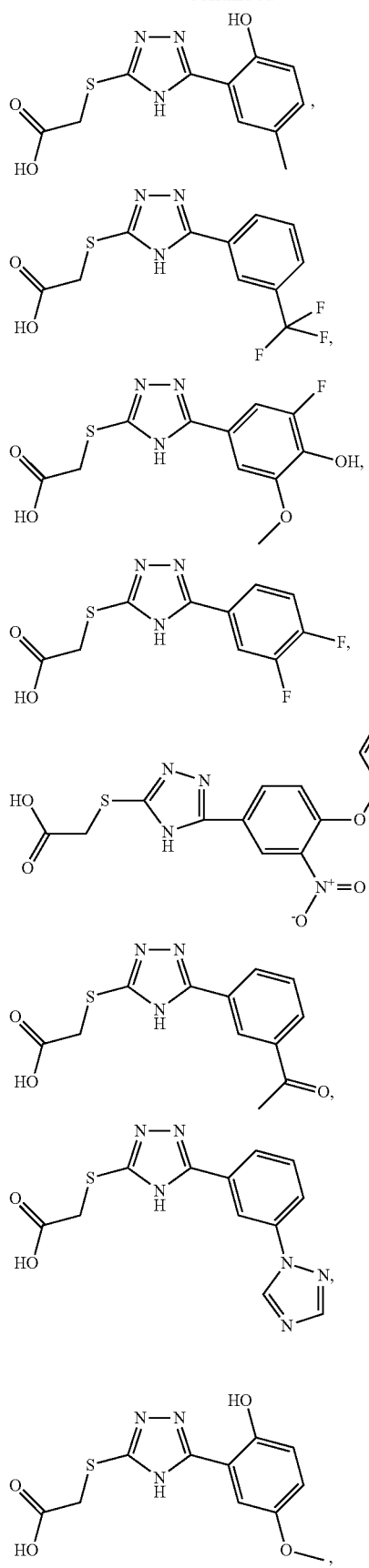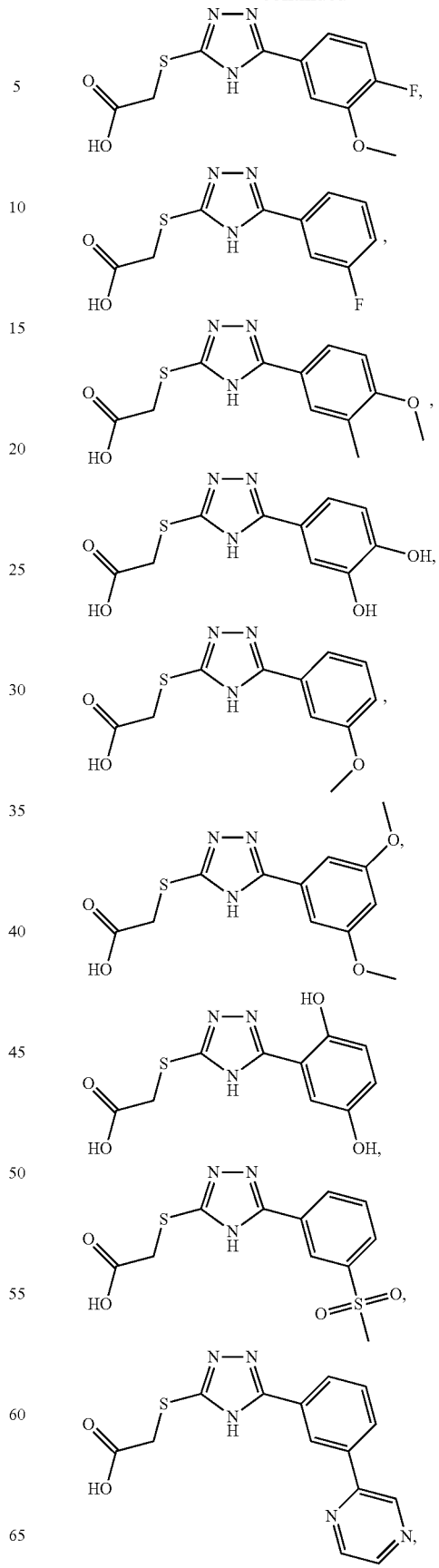

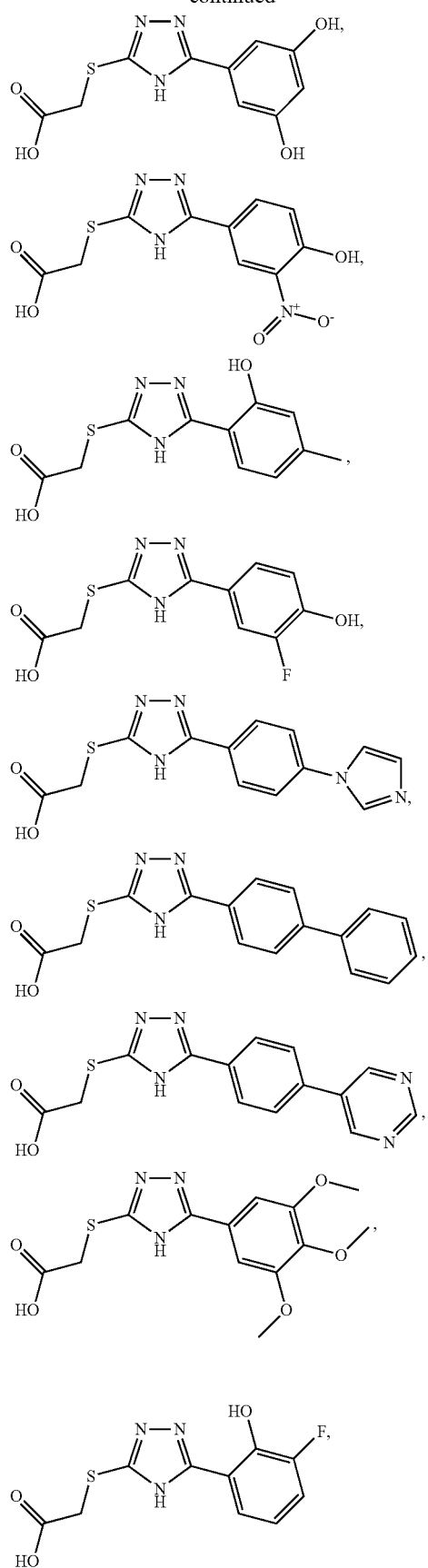
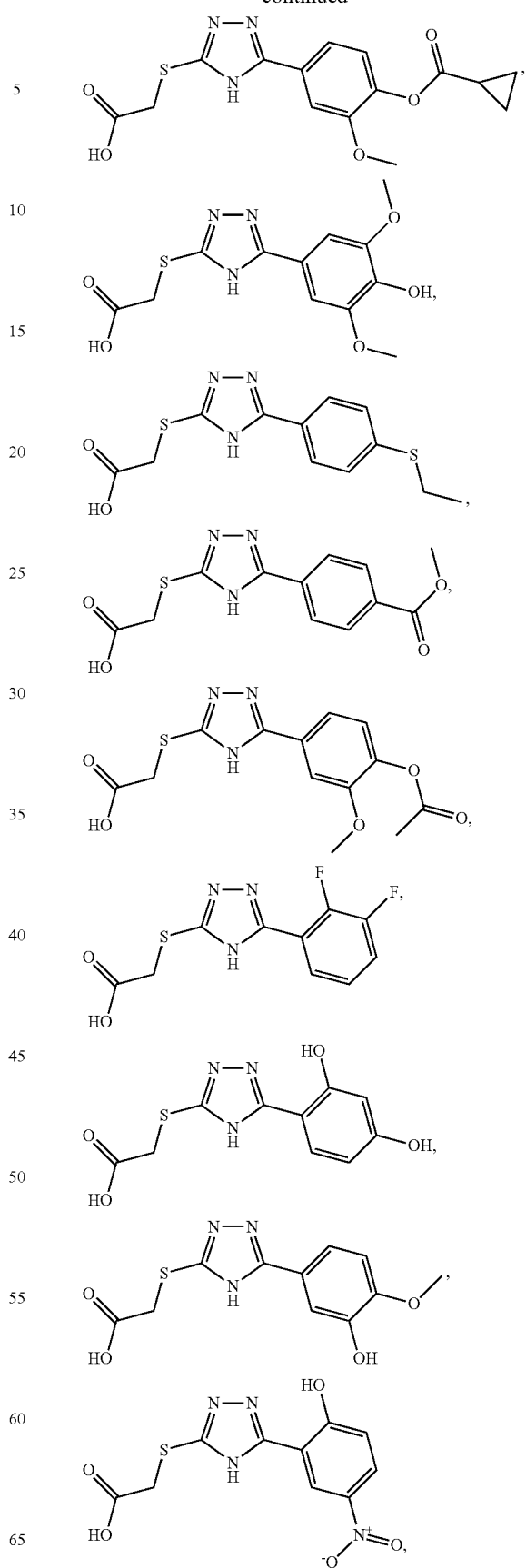

-continued
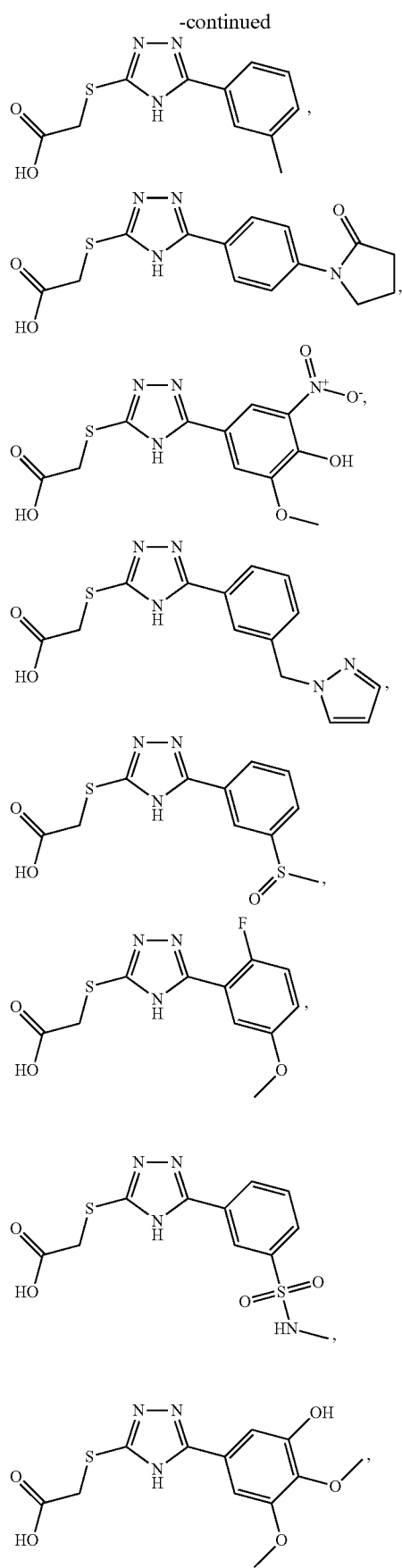
-continued
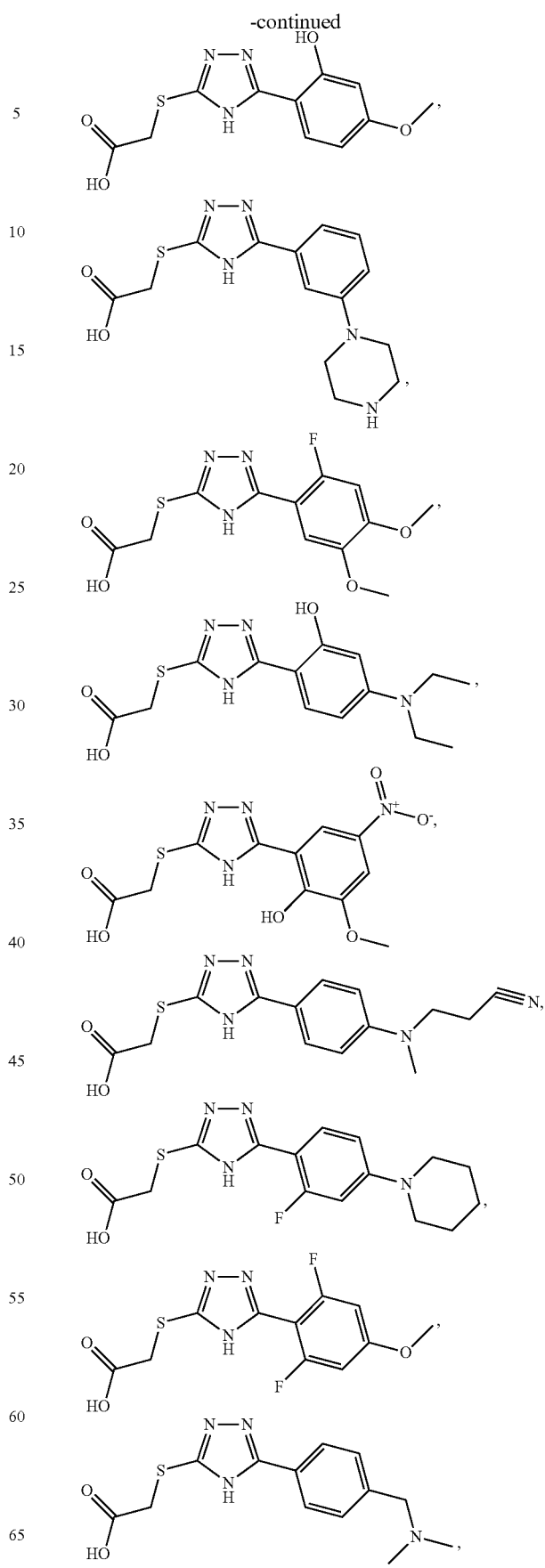

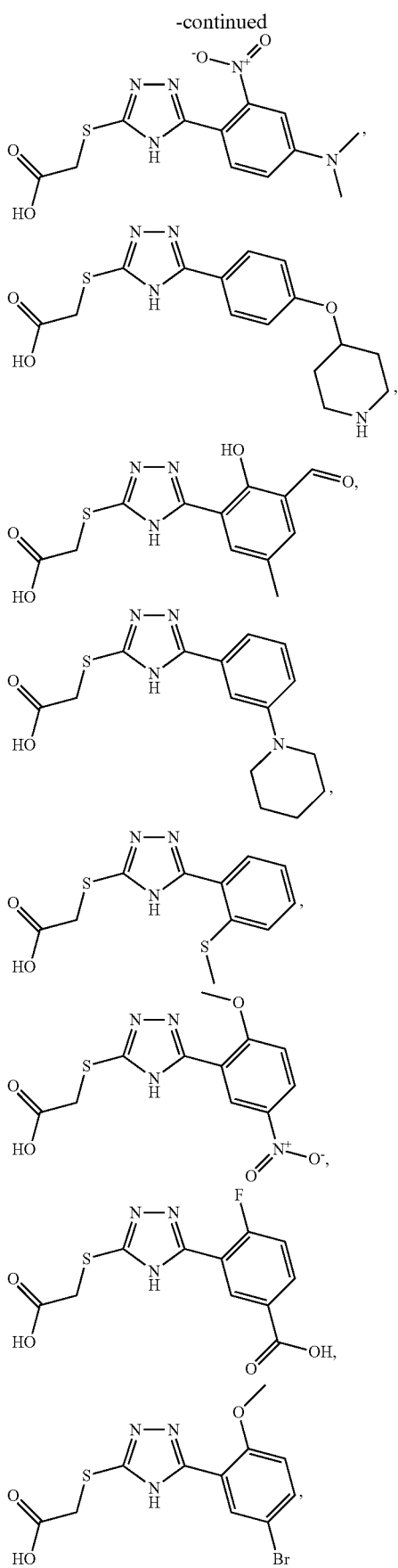
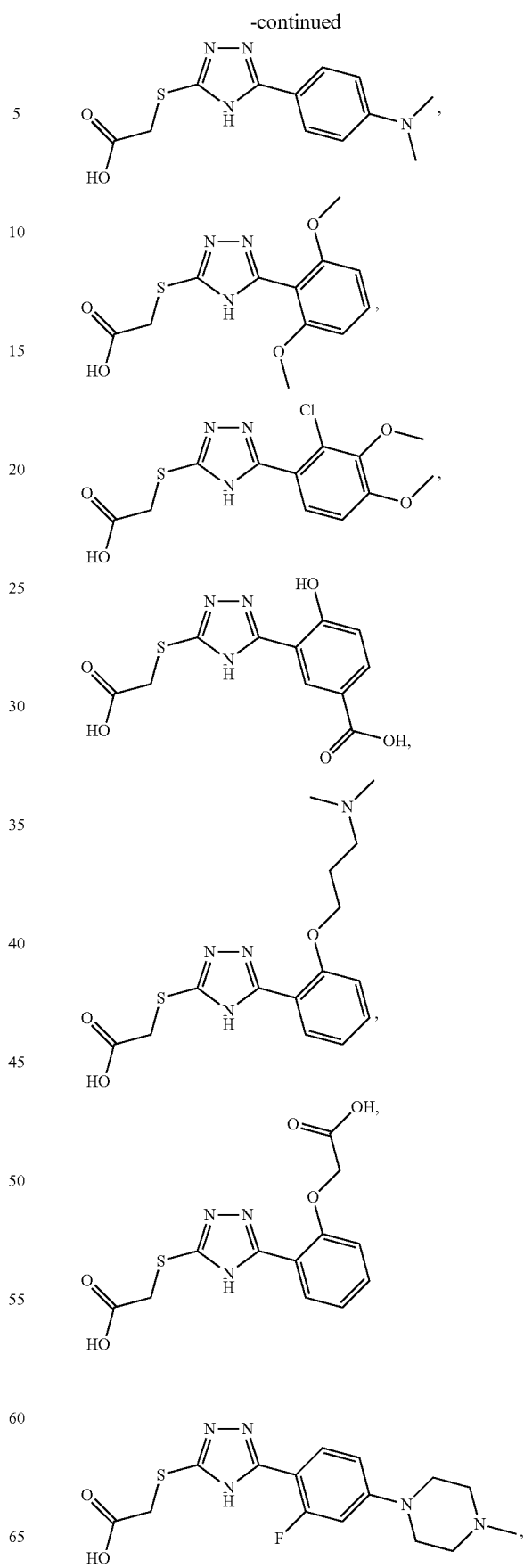

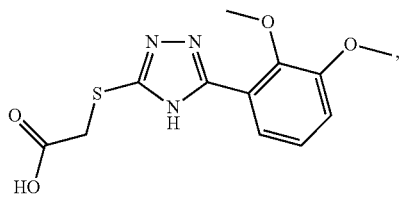
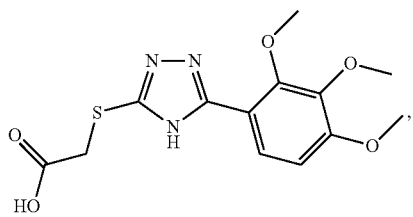
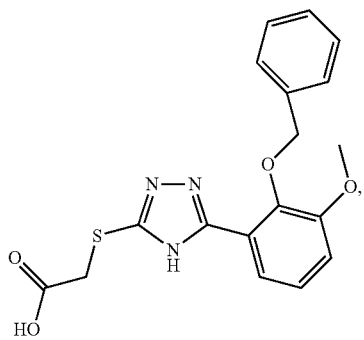
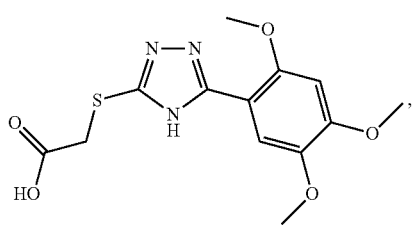
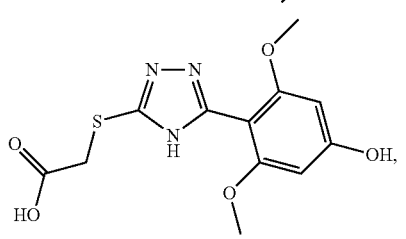
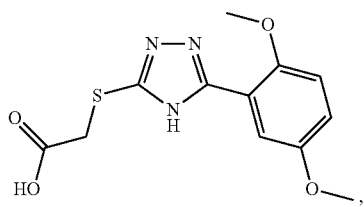
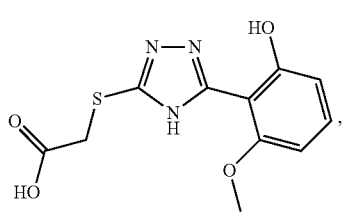
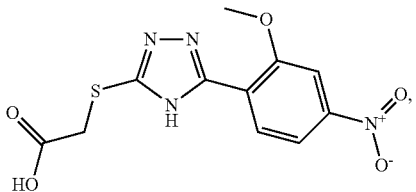
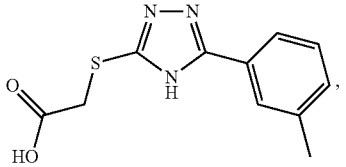
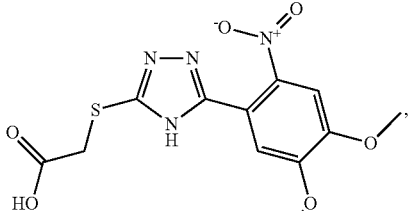
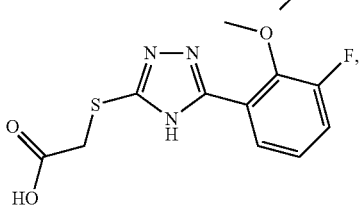
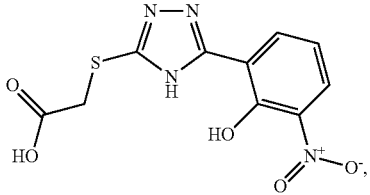
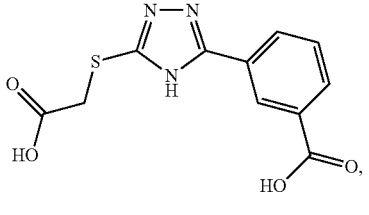
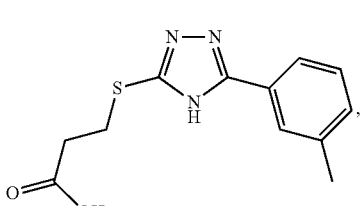
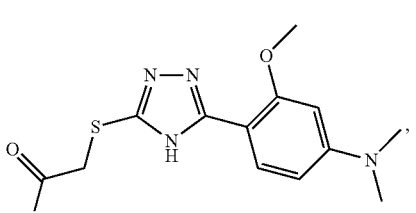

-continued

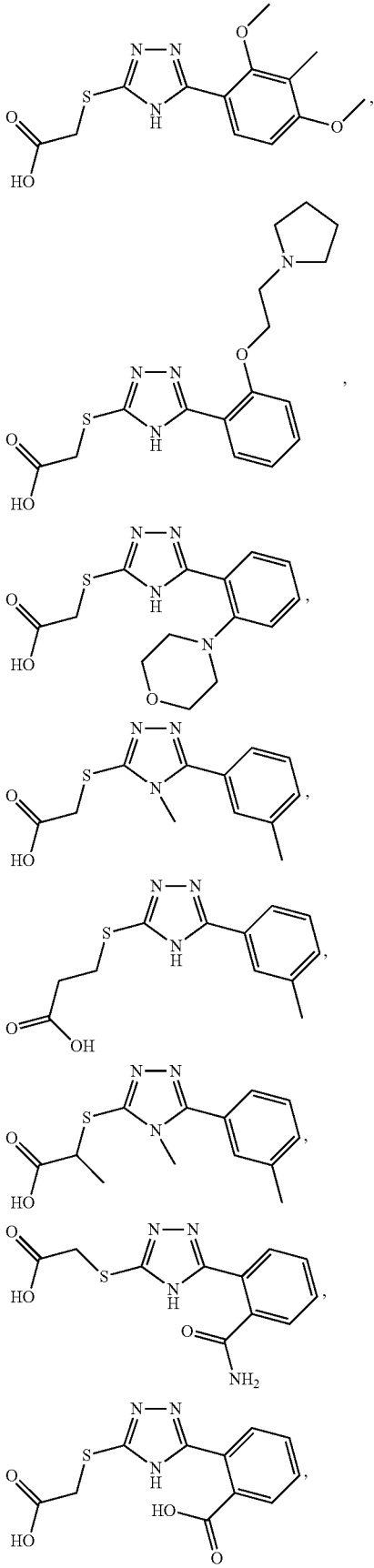

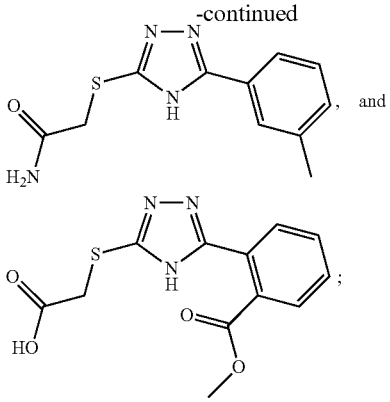

or a pharmaceutically acceptable salt form thereof.

E. Inhibitors of Formula (5)

In some cases, the inhibitors provided herein can be an inhibitor having the formula set forth in Formula (5):

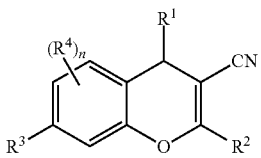

or a pharmaceutically acceptable salt form thereof, wherein:

$R^1$ is selected from the group consisting of: substituted or unsubstituted $(C_3-C_7)$ cycloalkyl, substituted or unsubstituted $(C_3-C_7)$heterocycloalkyl, substituted or unsubstituted $(C_5-C_{14})$aryl, and substituted or unsubstituted $(C_5-C_{14})$heteroaryl;

$R^2$ is $NR^5R^6$;

$R^3$ is $NR^5R^6$ each $R^4$ is independently selected from the group consisting of: H, $(C_1-C_6)$alkyl, substituted or unsubstituted $(C_3-C_7)$ cycloalkyl, substituted or unsubstituted $(C_3-C_7)$heterocycloalkyl, substituted or unsubstituted $(C_5-C_{14})$aryl, and substituted or unsubstituted $(C_5-C_{14})$heteroaryl;

each $R^5$ and $R^6$ is independently selected from the group consisting of: H and $(C_1-C_6)$alkyl; and n is an integer from 0 to 2.

In some embodiments, $R^1$ is selected from substituted or unsubstituted $(C_5-C_{14})$aryl, and substituted or unsubstituted $(C_5-C_{14})$heteroaryl. For example, $R^1$ can be a tolyl or thiophenyl moiety. In some embodiments, $R^2$ is $NH_2$. In some embodiments, $R^3$ is $NH_2$. In some embodiments, n is 0.

Non-limiting examples of an inhibitor of Formula (5) include:

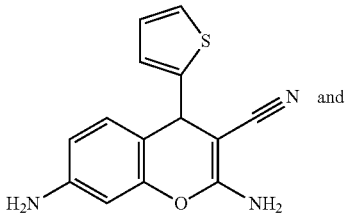

or a pharmaceutically acceptable salt form thereof.

F. Inhibitors of Formula (6)

In some cases, the inhibitors provided herein can be an inhibitor having the formula set forth in Formula (6):

or a pharmaceutically acceptable salt form thereof, wherein:

$R^1$ is selected from the group consisting of: H, $(C_1-C_6)$alkyl, halo, —CN, —$NR^3R^4$, —$NO_2$, $(C_1-C_6)$haloalkyl, —$O(C_1-C_6)$haloalkyl, —$OR^3$, and —$C(O)R^3$, $(C_3-C_7)$cycloalkyl, $(C_3-C_7)$heterocycloalkyl, $(C_5-C_{14})$aryl, and $(C_5-C_{14})$heteroaryl;

$R^2$ is selected from H and $(C_1-C_6)$alkyl;

each $R^3$ and $R^4$ is independently selected from the group consisting of: H and $(C_1-C_6)$alkyl; and n is an integer from 0 to 5.

In some embodiments, $R^1$ is selected from H, halo (e.g., Cl⁻), —$NO_2$, and $(C_5-C_{14})$aryl. For example, $R^1$ can be phenyl. In some embodiments, $R^2$ is H.

Non-limiting examples of an inhibitor of Formula (6) include:

or a pharmaceutically acceptable salt form thereof.

G. Inhibitors of Formula (7)

In some cases, the inhibitors provided herein can be an inhibitor having the formula set forth in Formula (7):

or a pharmaceutically acceptable salt form thereof, wherein:

each $R^1$ is independently selected from the group consisting of: H, $(C_1-C_6)$alkyl, halo, —CN, —$NR^5R^6$, $(C_1-C_6)$haloalkyl, —$O(C_1-C_6)$haloalkyl, —$OR^5$, and —$C(O)R^5$;

$R^2$, $R^3$, and $R^4$ are independently selected from H and $(C_1-C_6)$alkyl;

each $R^5$ and $R^6$ is independently selected from the group consisting of: H and $(C_1-C_6)$alkyl; and n is an integer from 0 to 5.

In some embodiments, $R^1$ is selected form H and —$OR^5$. For example, $R^1$ can be —OH. In some embodiments, $R^2$, $R^3$, and $R^4$ are H.

Non-limiting examples of an inhibitor of Formula (7) include:

or a pharmaceutically acceptable salt form thereof.

H. Additional Inhibitors
In some cases, the inhibitors provided herein can be an inhibitor selected from the group consisting of:
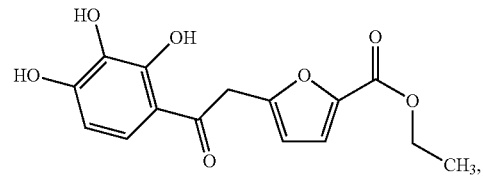
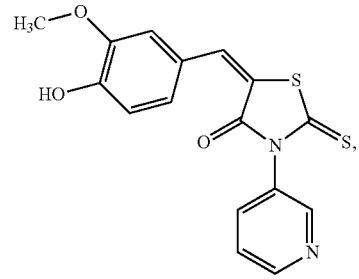
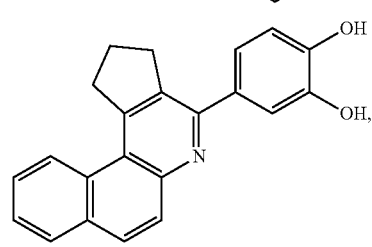
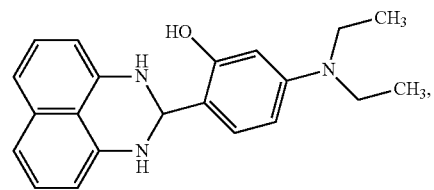 [SMILES: CCN(CC)c1ccc(C2Nc3cccc4cccc(c34)N2)c(O)c1]
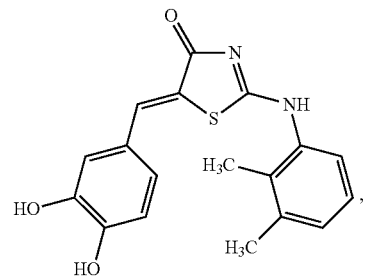
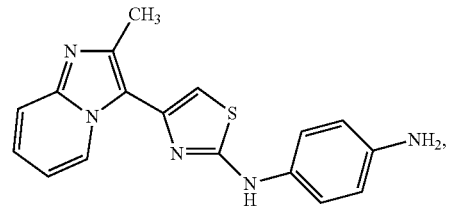
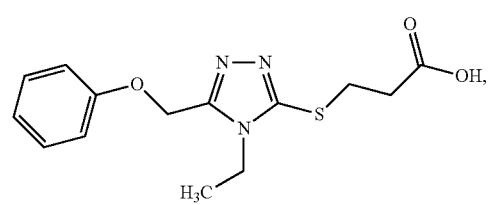 [SMILES: CCn1c(COc2ccccc2)nnc1SCCC(=O)O]
-continued
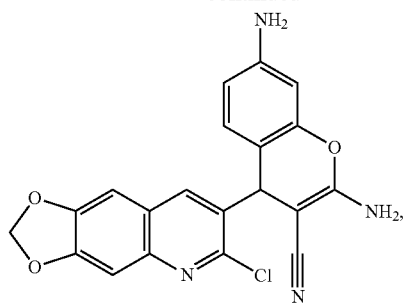
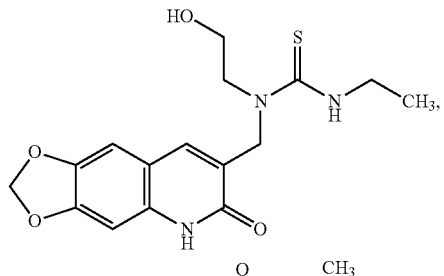
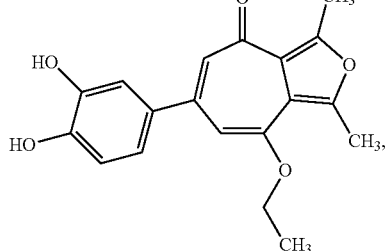
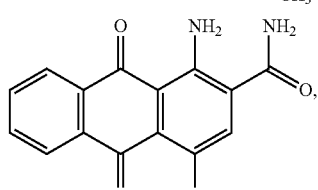
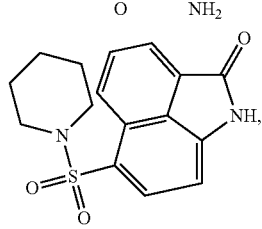
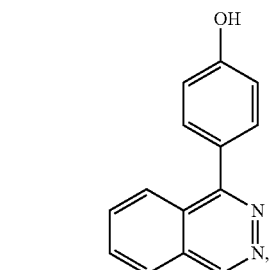
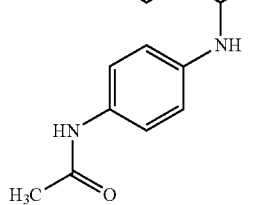

55
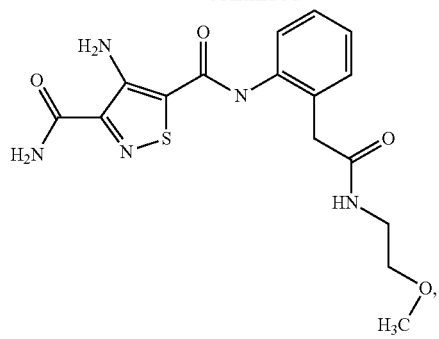
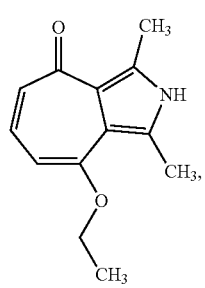
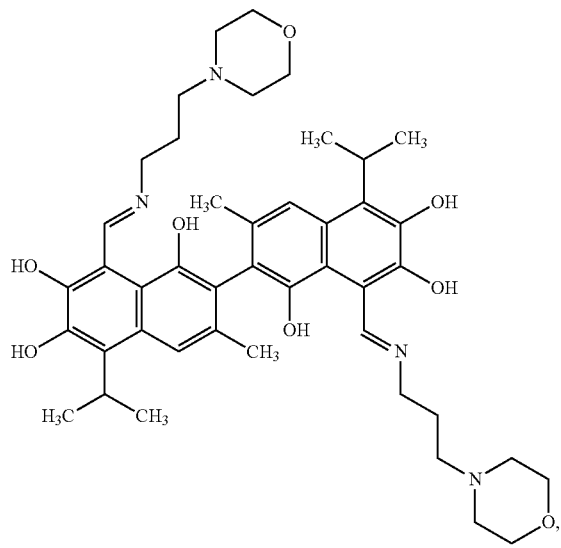
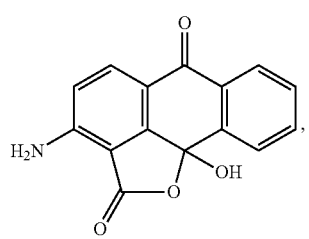
56
-continued
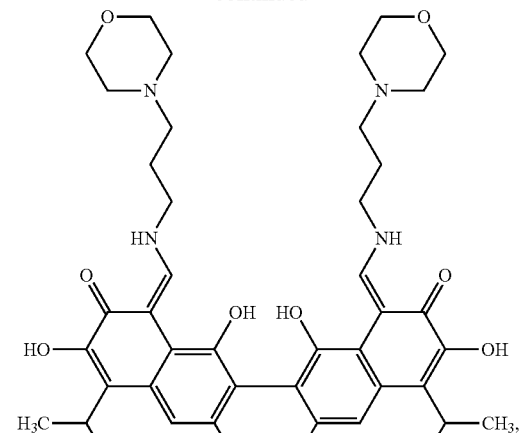
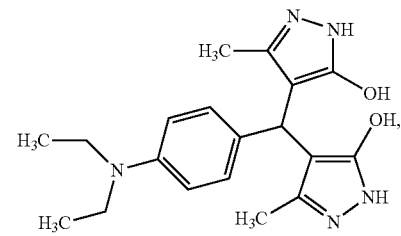
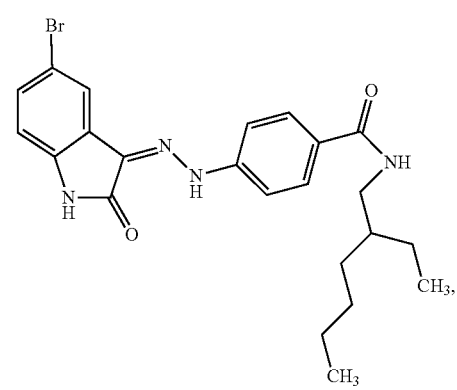
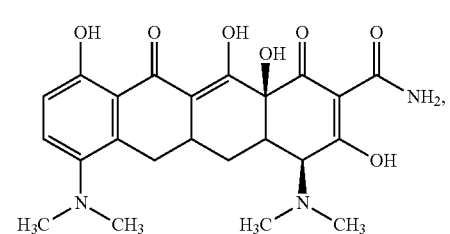

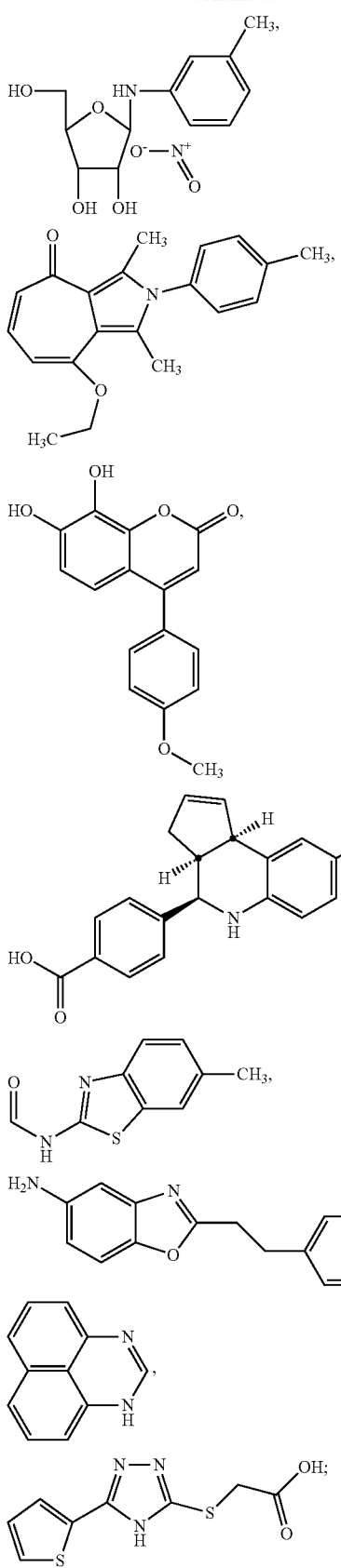

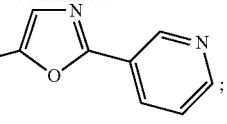

or a pharmaceutically acceptable salt form thereof.

An inhibitor provided herein, including a pharmaceutically acceptable salt thereof, can be purchased commercially or prepared using known organic synthesis techniques.

For example, a compound of formula (4) can be prepared as shown in Scheme 1:

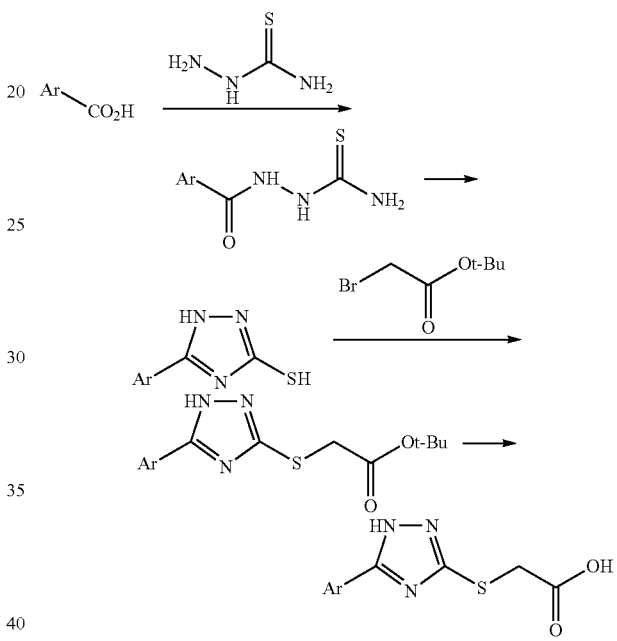

A reaction for preparing an inhibitor provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of an inhibitor can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1$^{st}$ Ed., Oxford University Press, 2000; and *March's Advanced Organic chemistry: Reactions, Mechanisms, and Structure*, 5$^{th}$ Ed., Wiley-Interscience Publication, 2001 (each of which is incorporated herein by reference in their entirety).

Pharmaceutically Acceptable Salts and Compositions

This document also provides pharmaceutically acceptable salts of the inhibitors provided herein. Examples of pharmaceutically acceptable salts of the inhibitors provided herein include acid addition salts and base salts of the inhibitors.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate, and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, and zinc salts.

Hemisalts of acids and bases may also be formed, for example, hemisulphate and hemicalcium salts.

An inhibitor provided herein intended for pharmaceutical use may be administered as a crystalline or amorphous product. In some cases, such a product may be obtained, for example, as a solid plug, powder, or film by methods such as precipitation, crystallization, freeze drying, spray drying, or evaporative drying. Microwave or radio frequency drying may be used for this purpose.

An inhibitor may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated is the installation of an inhibitor in the body of the patient in a controlled formulation, with systemic or local release of an inhibitor to occur at a later time. For example, an inhibitor can be localized in a depot for controlled release to the circulation, or for release to a local site. Advantageously, an inhibitor can be administered in the form of a pharmaceutical composition.

An inhibitor may be administered alone or in combination with one or more other inhibitors provided herein or in combination with one or more other drugs (or as any combination thereof). Generally, an inhibitor will be administered as a formulation in association with one or more pharmaceutically acceptable excipients. The term "excipient" is used herein to describe any ingredient other than an inhibitor(s) provided herein. The choice of excipient will to a large extent depend on factors such as the particular mode of administration, the effect of the excipient on solubility and stability, and the nature of the dosage form.

Non-limiting examples of pharmaceutical excipients suitable for administration of the inhibitors provided herein include any such carriers known to those skilled in the art to be suitable for the particular mode of administration. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of an inhibitor provided herein. In some embodiments, the excipient is a physiologically acceptable saline solution.

A pharmaceutical composition can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal ointments, creams, gels, and patch preparations and dry powder inhalers (see, e.g., *Ansel Introduction to Pharmaceutical Dosage Forms, Fourth Edition* 1985, 126).

The concentration of an inhibitor in a pharmaceutical composition will depend on absorption, inactivation, and excretion rates of the inhibitor, the physicochemical characteristics of the inhibitor, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the inhibitors. The pharmaceutically therapeutically active inhibitors are, in one embodiment, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the therapeutically active inhibitor sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an inhibitor as provided herein and optional pharmaceutical adjuvants in a carrier, such as, for example, water, saline, aqueous dextrose, glycerol, glycols, ethanol, and the like, to thereby form a solution or suspension. If desired, a pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing an inhibitor provided herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Pharmaceutical compositions suitable for the delivery of inhibitor provided herein and methods for their preparation will be readily apparent to those skilled in the art. Such compositions and methods for their preparation may be found, for example, in *Remington's Pharmaceutical Sciences*, 19th Edition (Mack Publishing Company, 1995).

Methods of Use

This document also provides methods and materials for using inhibitors of G protein couple receptor 6 kinase (GRK6) polypeptides. In some cases, an inhibitor provided herein may be used to treat any disease or disorder which involves the inhibition of a GRK6 polypeptide or a GRK6 polypeptide pathway. For example, a GRK6 polypeptide can be inhibited in a patient by administering a therapeutically effective amount of an inhibitor provided herein. In addition, a GRK6 polypeptide can be inhibited in a cell by contacting the cell with an effective amount of an inhibitor provided herein.

An inhibitor provided herein can have an $IC_{50}$ value in a GRK6 polypeptide inhibition assay ranging from about 0.1 µM to greater than about 20 µM. For example, provided herein are inhibitors having $IC_{50}$ values ranging from 0.1 to 5 µM (I), $IC_{50}$ values ranging from 5.1 to 10 µM (II), $IC_{50}$ values ranging from 10.1 to 20 µM (III), and $IC_{50}$ values >20 µM (IV). Values for selected compounds are shown in Table 1 below and in FIG. 3.

TABLE 1

| Structure | $IC_{50}$ |
|---|---|
| 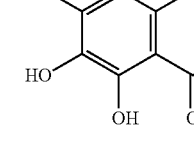 | II |

TABLE 1-continued

| Structure | $IC_{50}$ |
|---|---|
| 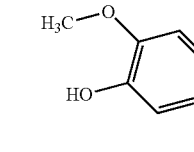 | II |
|  | IV |
| 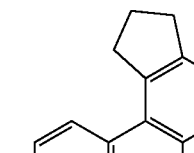 | IV |
| 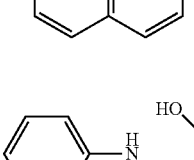 | II |
| 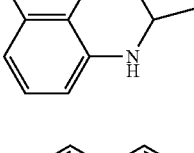 | II |
| | II |

TABLE 1-continued

| Structure | IC₅₀ |
|---|---|
| (structure) | III |
| (structure) | II |
| (structure) | I |
| (structure) | IV |
| (structure) | IV |
| (structure) | II |
| (structure) | IV |
| (structure) | IV |
| (structure) | IV |
| (structure) | I |
| (structure) | III |
| (structure) | III |

TABLE 1-continued
| Structure | IC$_{50}$ |
|---|---|
| 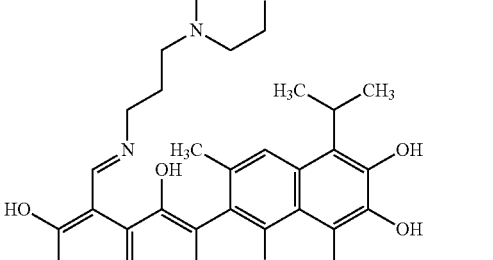 | IV |
| 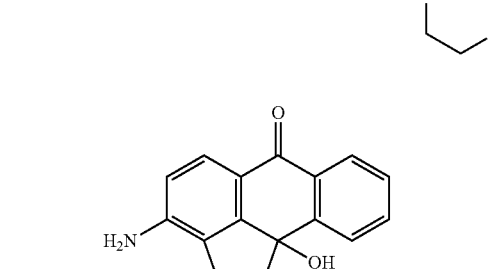 | IV |
| 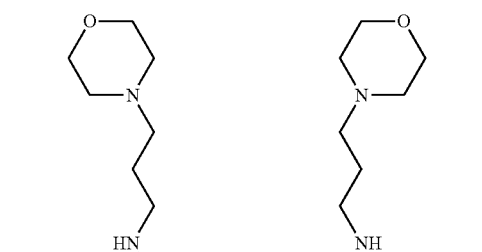 | IV |
| 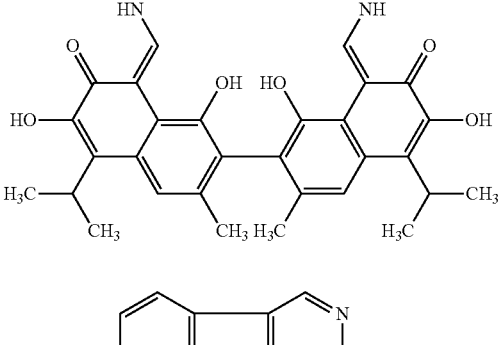 | IV |
| 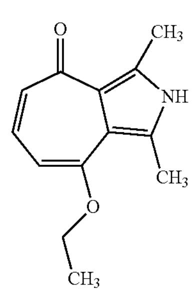 [SMILES: CCOc1cccc(=O)c2c(C)[nH]c(C)c12] | I |
TABLE 1-continued
| Structure | IC$_{50}$ |
|---|---|
| | III |
| 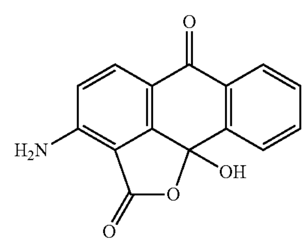 [SMILES: Nc1ccc2c3c1C(=O)OC3(O)c1ccccc1C2=O] | IV |
| | III |
| | III |

TABLE 1-continued

| Structure | IC$_{50}$ |
|---|---|
| (structure) | II |
| (structure) | I |
| (structure) | IV |
| (structure) | I |
| (structure) | II |
| (structure) | III |
| (structure) | I |
| (structure) | II |
| (structure) | I |
| (structure) | I |

TABLE 1-continued
| Structure | IC$_{50}$ |
|---|---|
| 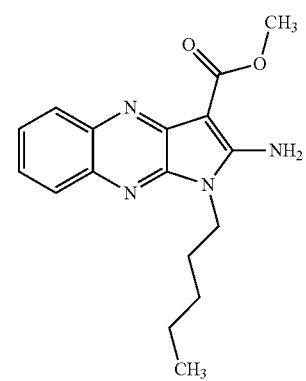 [SMILES: CCCCCn1c(N)c(C(=O)OC)c2nc3ccccc3nc21] | I |
| 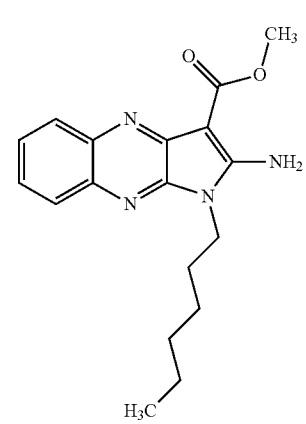 [SMILES: CCCCCCn1c(N)c(C(=O)OC)c2nc3ccccc3nc21] | I |
| 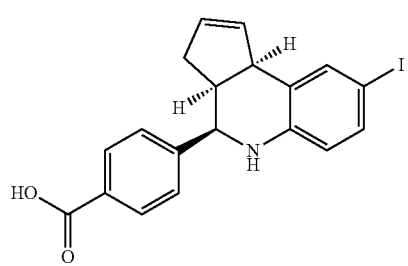 [SMILES: O=C(O)c1ccc([C@@H]2Nc3ccc(I)cc3[C@@H]3C=CC[C@@H]32)cc1] | II |
| 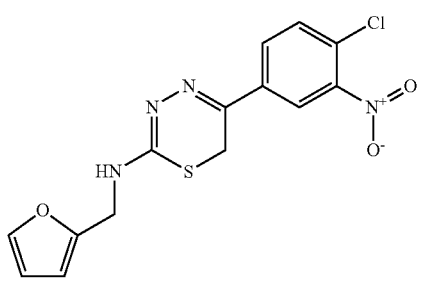 [SMILES: O=[N+]([O-])c1cc(C2=NN=C(NCc3ccco3)SC2)ccc1Cl] | II |
| 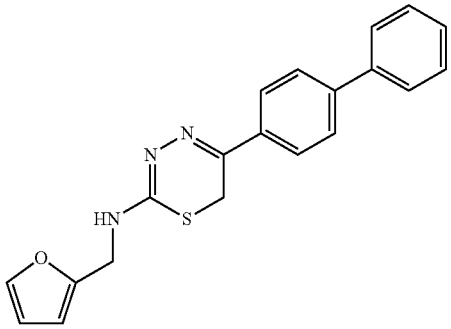 [SMILES: c1ccc(-c2ccc(C3=NN=C(NCc4ccco4)SC3)cc2)cc1] | III |
| 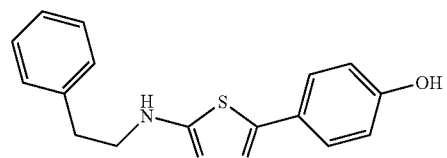 | IV |
| 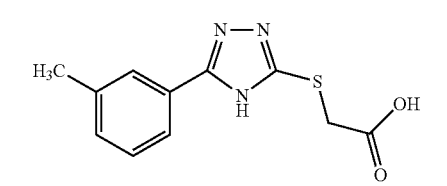 [SMILES: Cc1cccc(-c2nnc(SCC(=O)O)[nH]2)c1] | I |
| 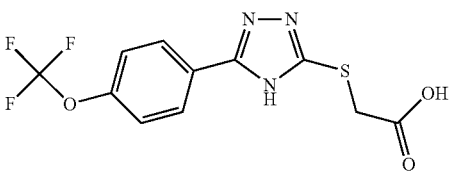 [SMILES: O=C(O)CSc1nnc(-c2ccc(OC(F)(F)F)cc2)[nH]1] | II |
| 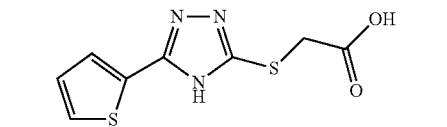 [SMILES: O=C(O)CSc1nnc(-c2cccs2)[nH]1] | I |
| 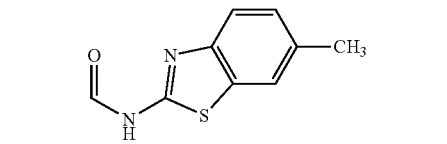 | IV |
| 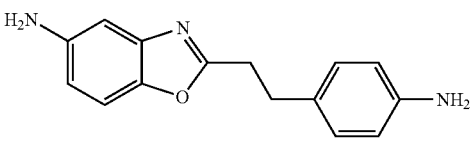 [SMILES: Nc1ccc(CCc2nc3cc(N)ccc3o2)cc1] | III |
| 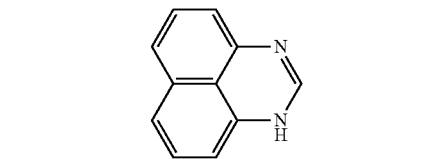 [SMILES: C1=Nc2cccc3cccc(c23)N1] | III |

TABLE 1-continued

| Structure | IC$_{50}$ |
|---|---|
| 5-(4-methoxyphenyl)-2-(pyridin-3-yl)oxazole (IV) | |

Diseases and disorders which involve overexpression or over-activation of a GRK6 polypeptide can include, for example, hematological malignancies, inflammation diseases, and autoimmune disorders.

Hematological malignancies that may be treated by the inhibitors, compositions and methods described herein include, but are not limited to, cancers of the bone marrow, blood, and lymph nodes. For example, hematological malignancies can include, for example, malignant lymphoma (reticulum cell sarcoma), multiple myeloma, acute myeloid leukemia, chronic myeloid leukemia, acute lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), harry cell leukemia, and Waldenstrom's macroglobulinemia.

Hematological malignancies may be solid tumors that may or may not be metastatic. Cancers may also occur, as in leukemia, as a diffuse tissue. Thus, the term "tumor cell", as provided herein, includes a cell afflicted by any one of the above identified disorders.

In some embodiments, the hematological malignancy is a B cell cancer. For example, the B cell cancer is a B cell Non-Hodgkin Lymphoma. B cell Non-Hodgkin's Lymphomas can include mediastinal large B-cell lymphoma, lymphoblastic B cell lymphoma, Waldenstrom's macroglobulinaemia, and follicular lymphoma. Thus, in some embodiments, the B cell Non-Hodgkin's Lymphoma is small lymphocytic lymphoma (SLL), a mantle cell lymphoma, a Burkitt's lymphoma, a follicle centre cell lymphoma, a follicular lymphoma, a Burkitt-like lymphoma, a marginal zone B-cell lymphoma (MZBCL), a nodal marginal zone B cell lymphoma, an extra-nodal marginal zone B cell lymphoma, a splenic marginal zone B cell lymphoma, a lymphoplasmacytic lymphoma, or a diffuse large B cell lymphoma. In some embodiments, the B cell cancer is myeloma.

In some embodiments, the B cell cancer is a B cell acute lymphocytic leukemia (B-ALL), a precursor B cell acute lymphocytic leukemia (B-ALL), a B cell chronic lymphocytic leukemia (B-CLL), a precursor B-lymphoblastic leukaemia, a precursor B-lymphoblastic lymphoma, a small lymphocytic lymphoma, a B cell prolymphocytic leukemia, an undifferentiated B cell lymphoma, a hairy cell leukemia, a mediastinal large B-cell lymphoma, a plasma cell myeloma, a plasmacytoma, a primary effusive lymphoma, a Burkitt's cell leukemia, or a B cell diffuse mixed lymphoma.

An inhibitor provided herein can also be administered in combination with existing methods of treating hematological malignancies, for example by chemotherapy, irradiation, or surgery. Thus, there is further provided a method of treating hematological malignancies comprising administering an effective amount of an inhibitor described herein, or a pharmaceutically acceptable salt form thereof, to a patient, wherein a therapeutically effective amount of one or more additional cancer chemotherapeutic agents are administered to the patient.

The inhibitors provided herein are also useful in treating an inflammatory disease in a patient. Examples of inflammatory diseases treated by an inhibitor provided herein include, but are not limited to, general inflammatory diseases such as encephalitis, inflammatory eye disease, otitis, pharyngitis, pneumonia, gastritis, enteritis, hepatitis, pancreatitis, nephritis, cystitis, urethritis, endometritis, vaginitis, arthritis, and peripheral neuritis, and further include inflammatory diseases that secondarily cause inflammation, such as malignant tumor, infectious diseases, allergic diseases, autoimmune diseases (such as rheumatism, systemic lupus erythematosus, and sarcoidosis), ischemic diseases (such as myocardial infarction and cerebral infarction), metabolic diseases (such as diabetes and gout), injury, scald, chemical corrosion, and neurodegenerative diseases (such as Alzheimer's disease).

For example, an inhibitor provided herein can be used to treat an autoimmune disease or disorder. The term "autoimmune" refers to the process by which immune system components such as antibodies or lymphocytes attack or harm molecules, cells, or tissues of the organism producing them. The term "autoimmune disorders" refers to diseases where damage, such as tissue damage, or pathogenesis is, at least partially, a result of an autoimmune process.

In some embodiments, suppression of the immune response is useful in the treatment of patients suffering from autoimmune diseases as well as adverse immune reactions associated with organ transplantations.

Autoimmune diseases include allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, psoriasis, rheumatoid arthritis, sarcoidosis, scleroderma, and systemic lupus erythematosus.

Inhibitors provided herein are effective to inhibit a GRK6 polypeptide in a cell, for example, in a cancer cell (e.g., in a cell from a hematological malignancy). Therefore there is also provided a method of inhibiting a GRK6 polypeptide in a cell comprising contacting the cell with an effective amount of an inhibitor provided herein, or a pharmaceutically acceptable salt form thereof. The method may be performed by contacting the cell with an inhibitor as described herein, or a pharmaceutically acceptable salt form thereof, in vitro, thereby inhibiting a GRK6 polypeptide in vitro. Uses of such an in vitro method of inhibiting a GRK6 polypeptide include, but are not limited to use in a screening assay (for example, wherein an inhibitor described herein is used as a positive control or standard compared to compounds of unknown activity or potency in inhibiting a GRK6polypeptide).

EXAMPLES

General Assay Conditions

The following assay conditions were deemed to be optimal and were used in subsequent experiments and screening.

Buffer: 50 mM TRIS-HCl, pH 7.5, 5 mM MgCl$_2$, 2 mM DTT, 0.01% Triton X-100 10 µM Na$_3$VO$_4$, 10 µM b-GP, 1% DMSO Enzyme: 20 nM GRK6, recombinant full-length GST-tagged human protein
ATP: 12 µM (Km)
Peptide substrate (Peptide 216): 1 µM
Incubation time: 7 hrs A new assay for screening inhibitors of GRK6 was developed. Similar screens have been developed for other targets. See, for example, "Fragment-based screening of enzyme drug targets: Microfluidic mobility shift assay improves confidence in candidate selection." Caliper Life Sciences White Paper (2010); and Pollack, S. J. et al. J. Comput. Aided Mol. Des. (2011) 25:677-687.

Example 1—Assay Validation

A. Pharmacology $IC_{50}$ values of three model inhibitors were determined at ATP Km. The model compounds were chosen based on availability of literature data and included Staurosporine, Ro-31-8220 and H89. The compounds were tested in 12-pt dose response format using 3× serial dilutions. All determinations were performed in duplicates. To obtain the $IC_{50}$ values and the Hill coefficient, the 4-parameter logistic equation was fitted to the data by non-linear regression using XLFit software. The $IC_{50}$ values obtained (FIG. 1) were in good agreement with published data.

B. Suitability of High Throughput Screening (HTS)

HTS validation experiments were carried out in order to determine: Z'-factor of the assay; HTS plate uniformity; Plate-to-plate variability; Day-to-day variability; and Reagent stability.

Figure 2:
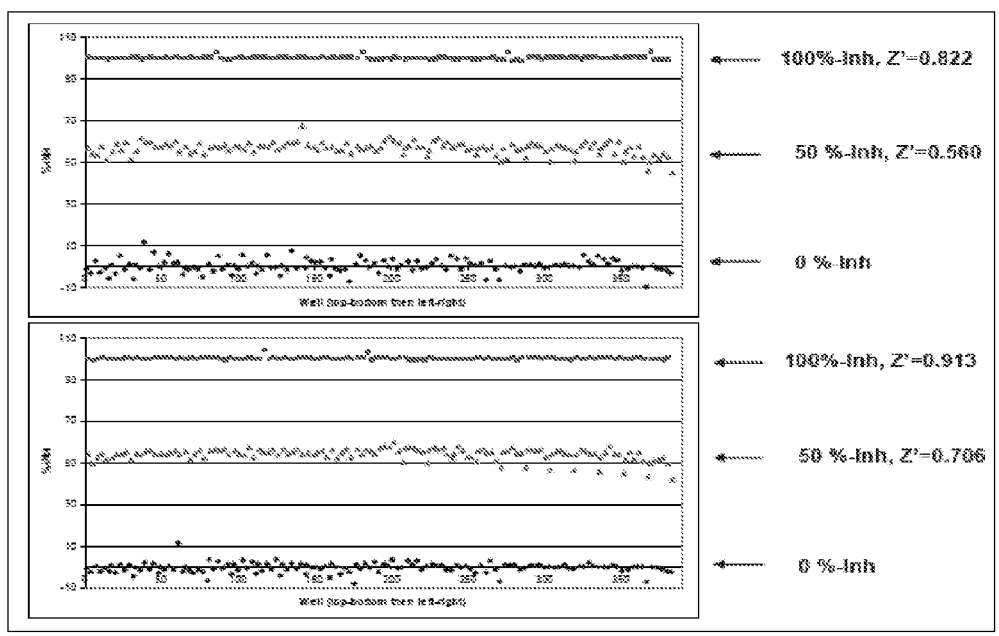
FIG. 2 illustrates examples of validation plate results showing good plate uniformity and no clear signs of significant systematic errors or across-plate trends. Specifically shown are the percent inhibition values for the three experimental conditions plotted against well number, where the wells are ordered by row first, then by column. Data on two plates collected on two different days are shown.

Three model 384-well assay plates were assembled with interleaved samples containing either DMSO only (0% inhibition), model inhibitor (staurosporine) at 1×$IC_{50}$ concentration (~50% inhibition) or 20 mM EDTA (~100% inhibition). The plates were assembled using the sample handling approach which fully imitates the HTS. Percent conversion of the substrate peptide was determined in each well. The data were used to calculate average, STDEV and CV for each experimental condition on each plate and to obtain Z' factors corresponding to 50% inhibition and to 100% inhibition. To assess plate uniformity, the percent inhibition was plotted against well number, where the wells are ordered either by row first, then by column, or by column first, then by row. The resulting scatter plots were assessed for any signs of drift or edge effects (FIG. 2). To assess plate-to-plate variability the average percent inhibition at 1×$IC_{50}$ concentration was compared between each plate. To assess day-to-day variability and reagent stability, the experiment was repeated on three different days.

The overall assay Z' (across all validation plates) were excellent: Median Z'=0.907 for 100%-Inhibition condition; and Median Z'=0.595 for 50%-Inhibition condition.

As shown on FIG. 2, plate uniformity was good, there were no clear signs of significant systematic errors or across-plate trends. Similarly, no significant differences were observed between validation plates run on the same day or on any of the three validation test days indicating that reagent stability was also satisfactory.

In conclusion, the validation data obtained showed excellent assay performance and demonstrated that the LabChip-based GRK6 assay developed was suitable for HTS.

Example 2—Fragment Screen

Using the GRK6 assay described above, a 3,000 compound fragment library was screened in order to: assess druggability of GRK6 as a target; and identify potential small molecular scaffolds that are capable of inhibiting GRK6.

Each fragment compound was tested at two nominal concentrations (50 µM and 100 µM) located on two independent assay plates. Reference inhibitor Staurosporine was tested on each HTS plate in 8 pt dose response format.

The quality of data from each plate was assessed by determining: Z' (100% inhibition vs 0% inhibition), and $IC_{50}$ value of the reference compound. Both robustness (Z') and reproducibility of the fragment screen were excellent: Z' values were >0.8 for all plates and the $IC_{50}$ value of the reference inhibitor varied very little from plate-to-plate.

The 2-point fragment screen identified 161 hits at 100 µM, and 97 hits at 50 µM test concentration using a 20% inhibition hit threshold. The 97 hits observed at 50 µM were all members of the 161 hits at 100 µM with the exception of four compounds.

The 91 fragments that showed consistent inhibition at the 2 test concentrations were tested in the GRK6 assay using 8-pt concentration-response format with top concentration of 200 µM. The concentration-response curves obtained were assessed for potency ($IC_{50}$) and for Hill Slope values.

Upon completion of the Fragment screening, a follow up concentration-response study was performed in order to: confirm primary fragment hits, determine ligand efficiency of the active fragments; and perform SAR of the active fragments.

The 91 fragments that showed consistent inhibition at the two test concentrations were tested in the GRK6 assay using 8-pt concentration-response format with top concentration of 200 µM. The concentration-response curves obtained were assessed for potency ($IC_{50}$) and for Hill Slope values.

In summary, 46 "well-behaved" inhibitory fragment hits were identified for GRK6 in the fragment screen. These results demonstrated the druggability of the GRK6 kinase target and provided a rational basis for the selection of compounds to be screened in the subsequent HTS.

Example 3—HTS for GRK6 Inhibitors

A 30,000 compound GRK6-kinase focused library was assembled and was screened in HTS mode. The compounds were tested at a nominal concentration of 10 µM in single determinations. The overall result statistics of the HTS are shown below. QC data of the screen indicates excellent assay performance as in the fragment screen.

Total number of HTS compounds screened: 30,098
Plate Z'-statistics (n=86): min Z'=0.66, max Z'=0.92, median Z'=0.8
Compound statistics:
Average %-Inhibition: 2.78%
STDEV: 7.82%
3-sigma inhibition threshold: 24%
Number of inhibitor hits above 3σ: 438
Number of inhibitor hits above 6σ: 193

The HTS resulted in the identification of 438 active compounds (hits) using the statistical hit threshold of three sigma (or 20% inhibition if it was lower). Hits were clustered into chemotypes based on structure similarity and prioritized based on chemical tractability and drug-likeness. Since the subsequent $IC_{50}$ studies were limited to 50 compounds, a subset of the hits were selected for follow up. The selection was performed in a way to provide the best possible coverage and representation of the hit series and singletons.

Example 4—IC$_{50}$ Determination of Selected Hits

Fifty-one selected HTS hits were confirmed and further characterized by determining IC$_{50}$ values in the GRK6 assay. More specifically, the following activities were performed: 8-point concentration-response determinations in singlicate wells (top concentration=60 µM, 3-fold dilution steps); Repeat tests for QC failed or inconclusive compounds; and Repeat tests (titrate down) for compounds with >50% inhibition at all tested concentration.

Figure 3:
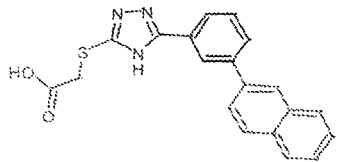
FIG. 3 provides a table of $IC_{50}$ values for selected compounds of Formula (4).
Figure 3:
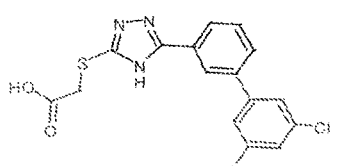
Figure 3:
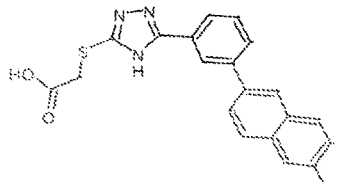
Figure 3:
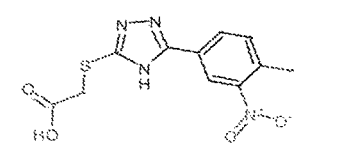
Figure 3:
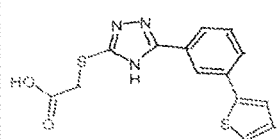
Figure 3:
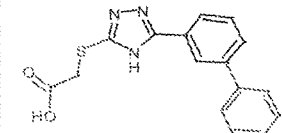
Figure 3:
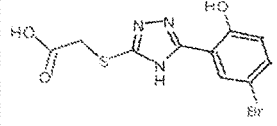
Figure 3:
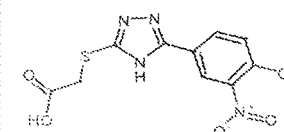
Figure 3:
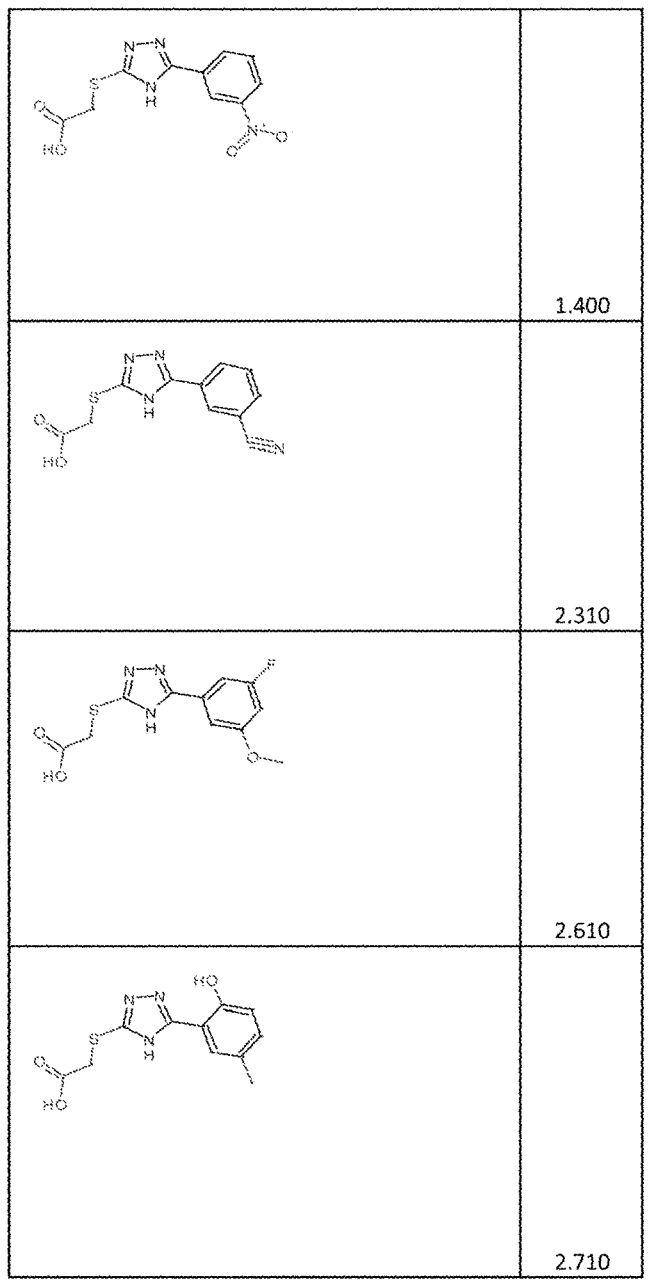
Figure 3:
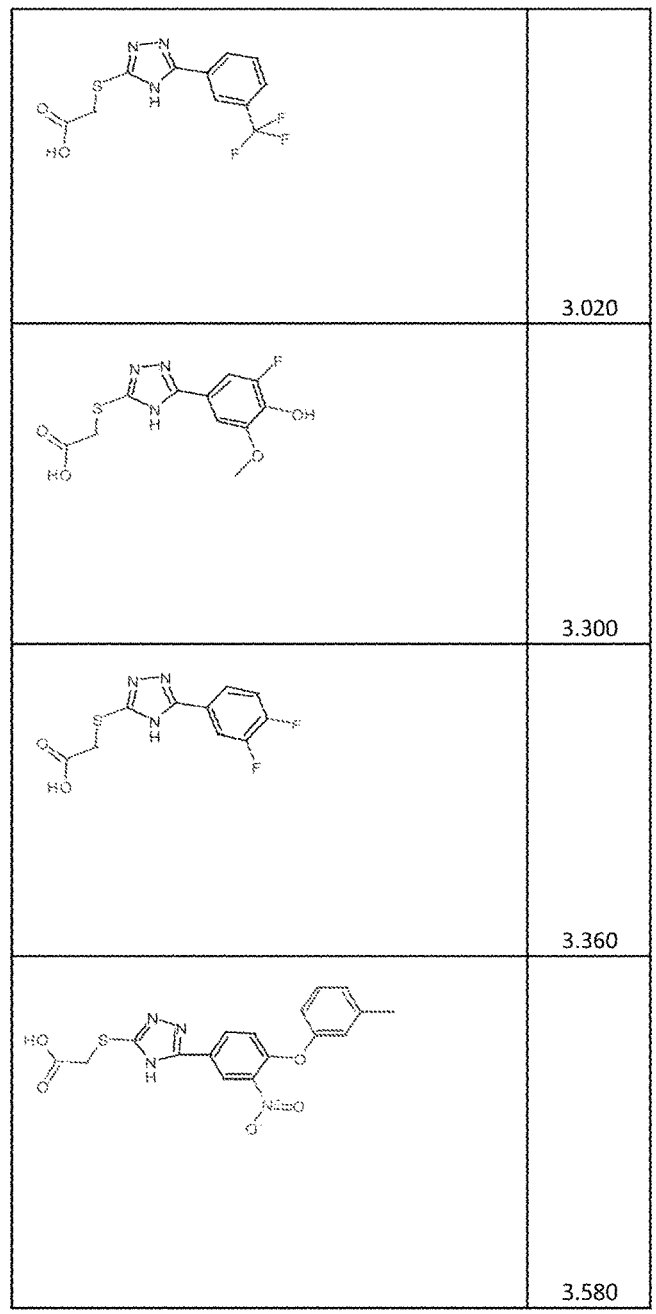
Figure 3:
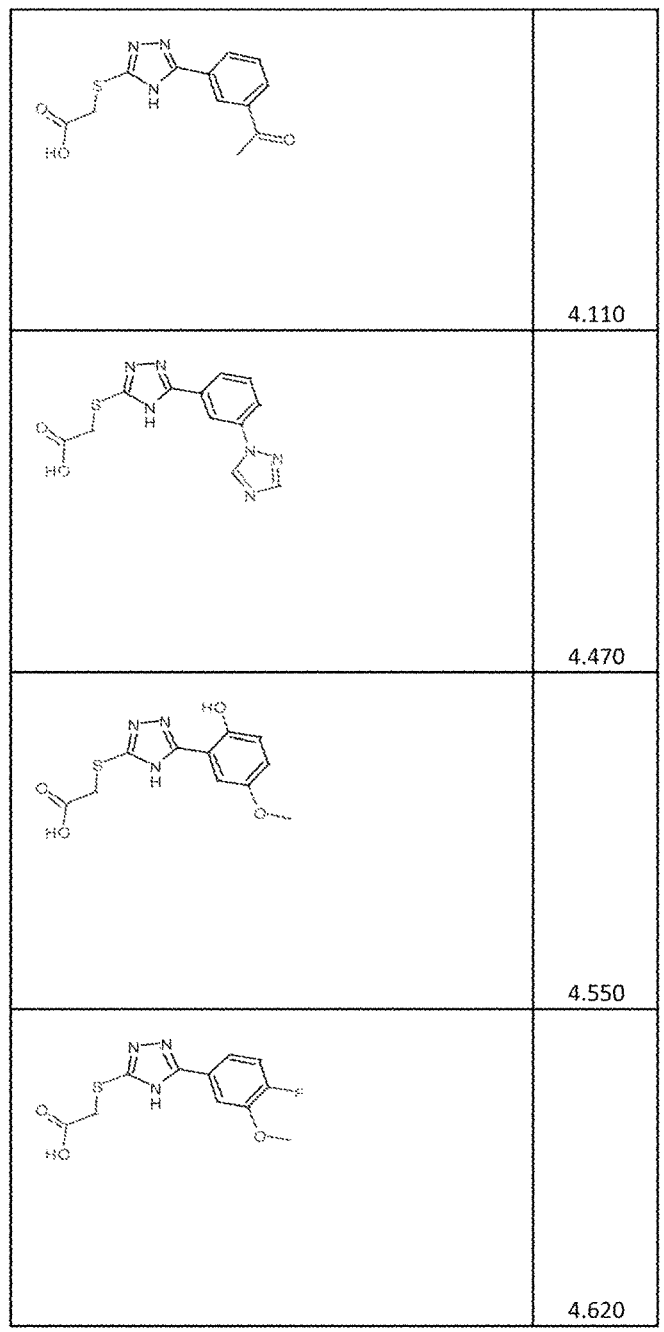
Figure 3:
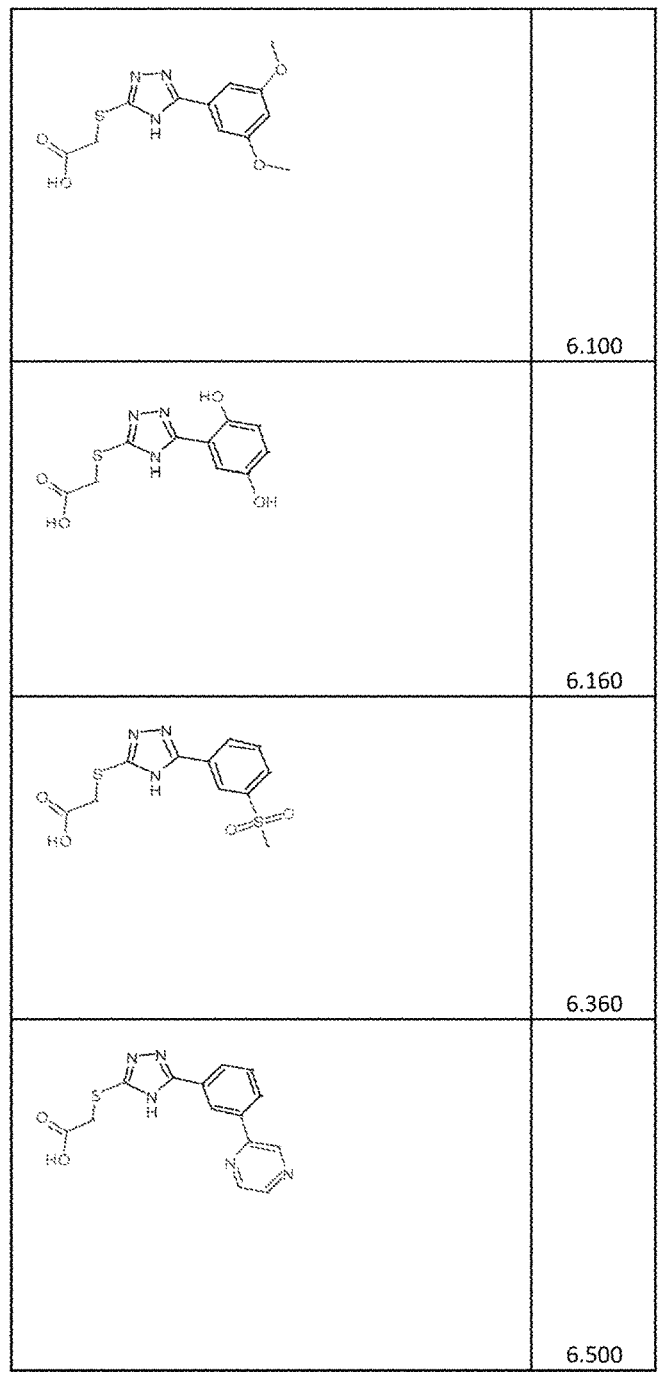
Figure 3:
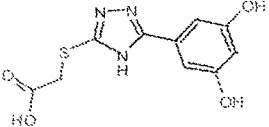
Figure 3:
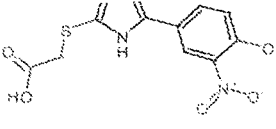
Figure 3:
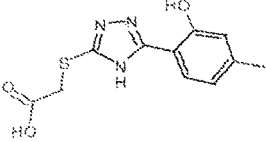
Figure 3:
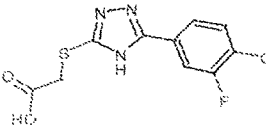
Figure 3:
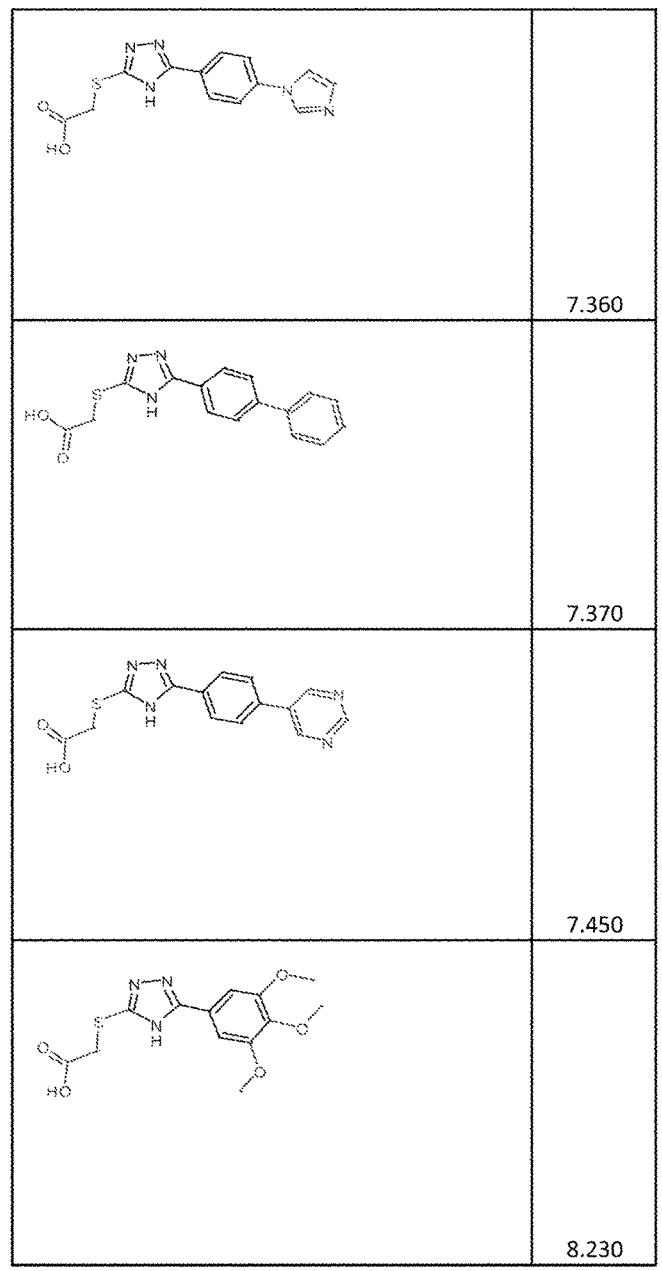
Figure 3:
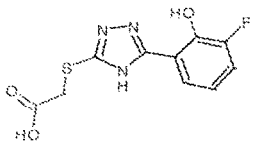
Figure 3:
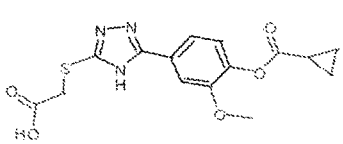
Figure 3:
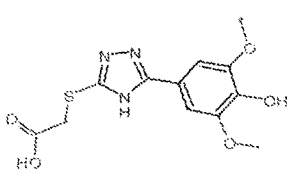
Figure 3:
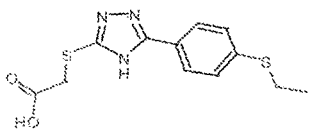
Figure 3:
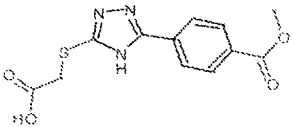
Figure 3:
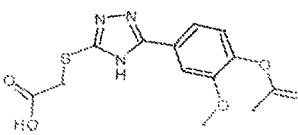
Figure 3:
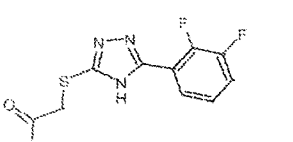
Figure 3:
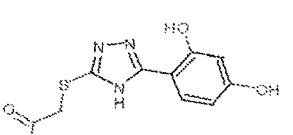
Figure 3:
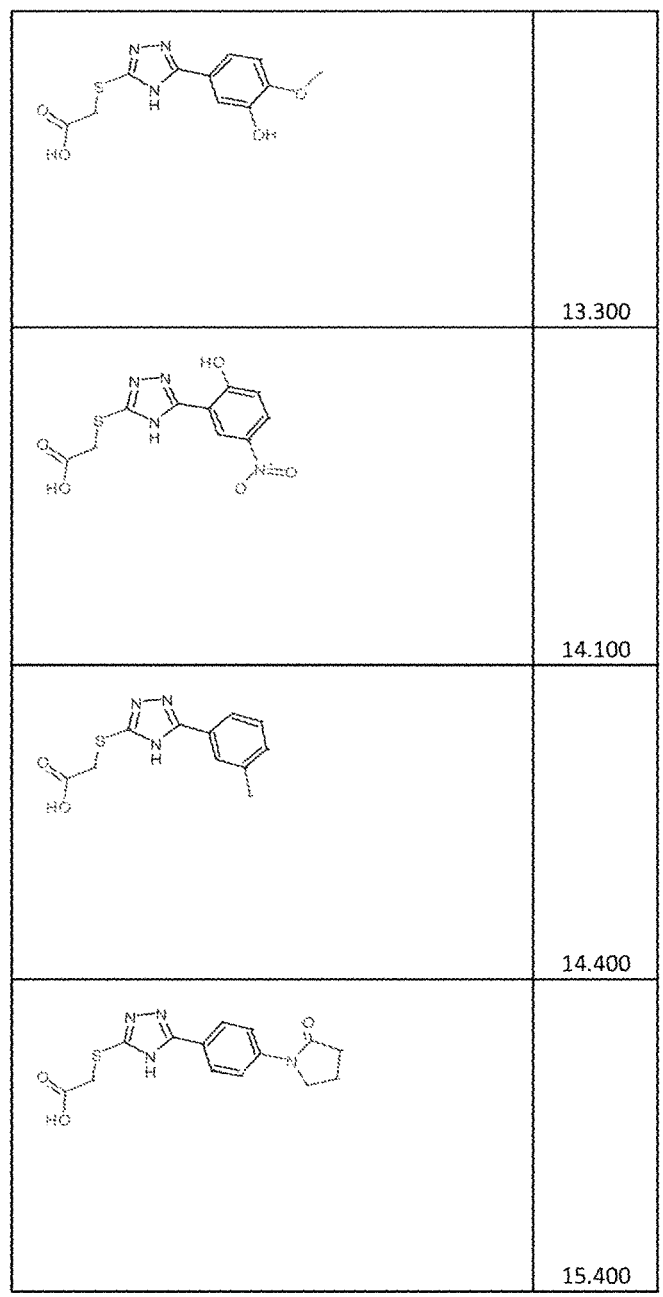
Figure 3:
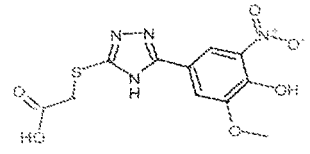
Figure 3:
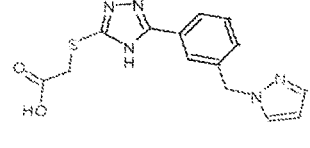
Figure 3:
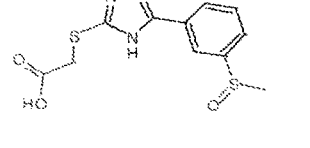
Figure 3:
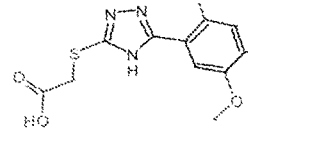
Figure 3:
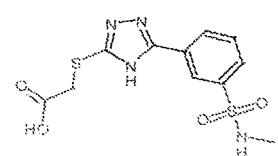
Figure 3:
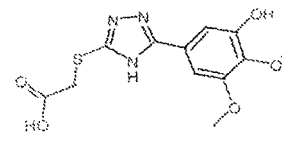
Figure 3:
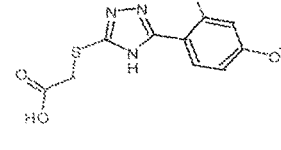
Figure 3:
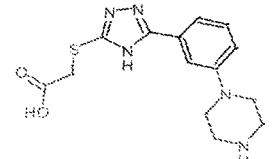
Figure 3:
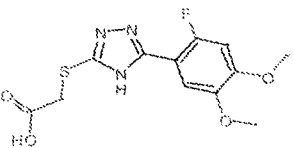
Figure 3:
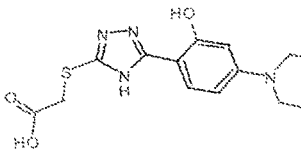
Figure 3:
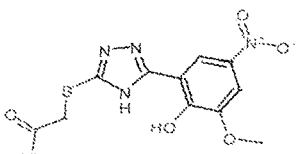
Figure 3:
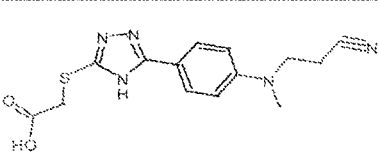
Figure 3:
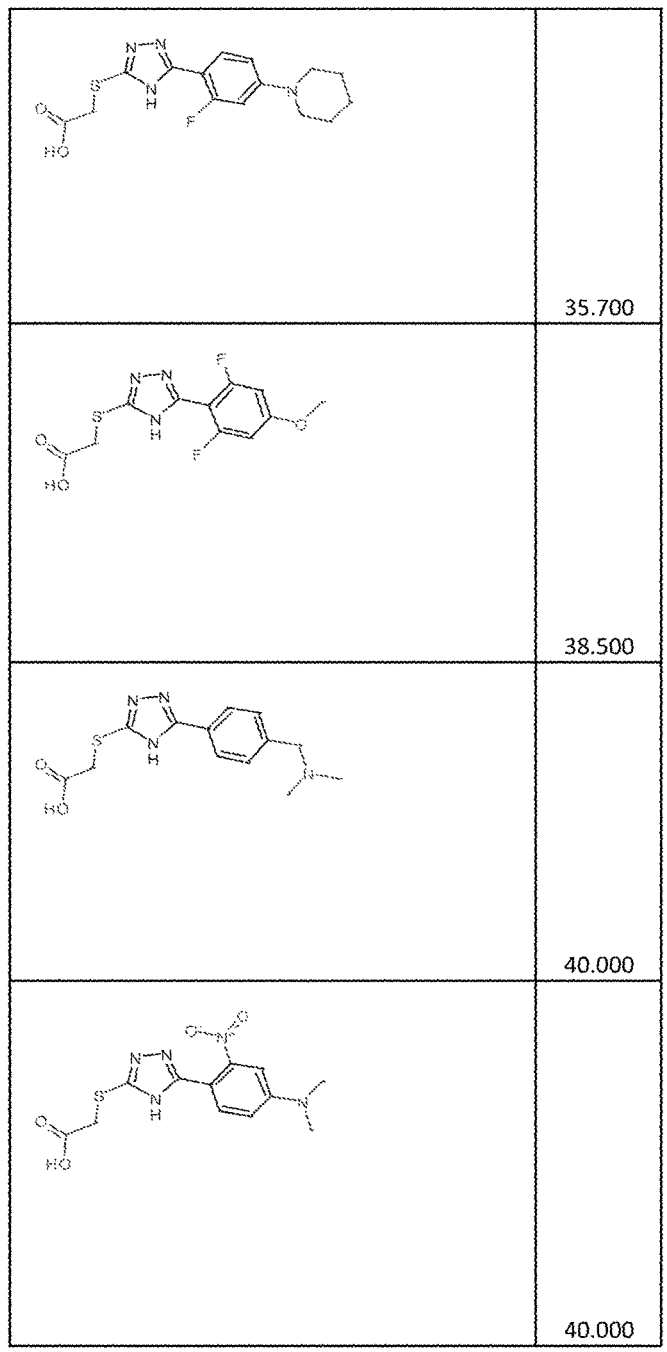
Figure 3:
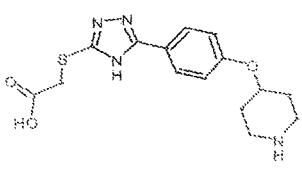
Figure 3:
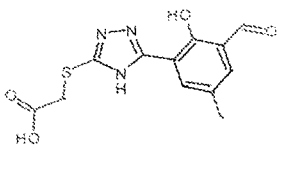
Figure 3:
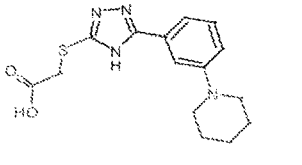
Figure 3:
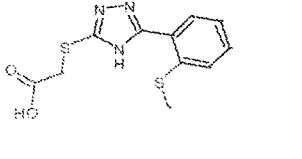
Figure 3:
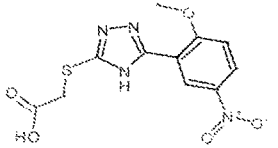
Figure 3:
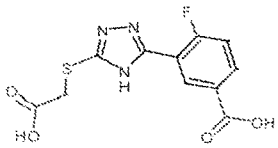
Figure 3:
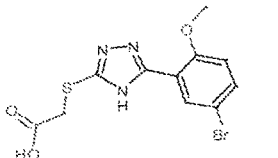
Figure 3:
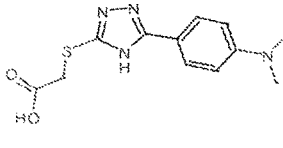
Figure 3:
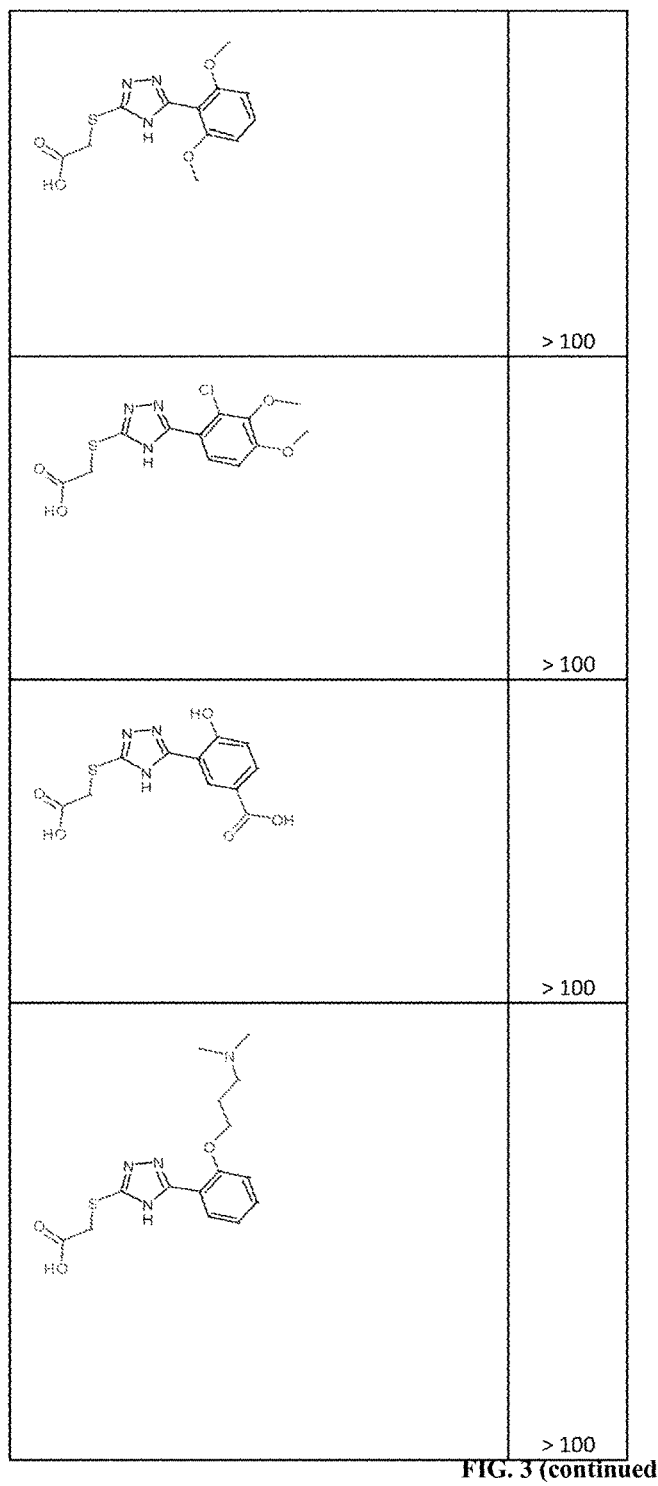
Figure 3:
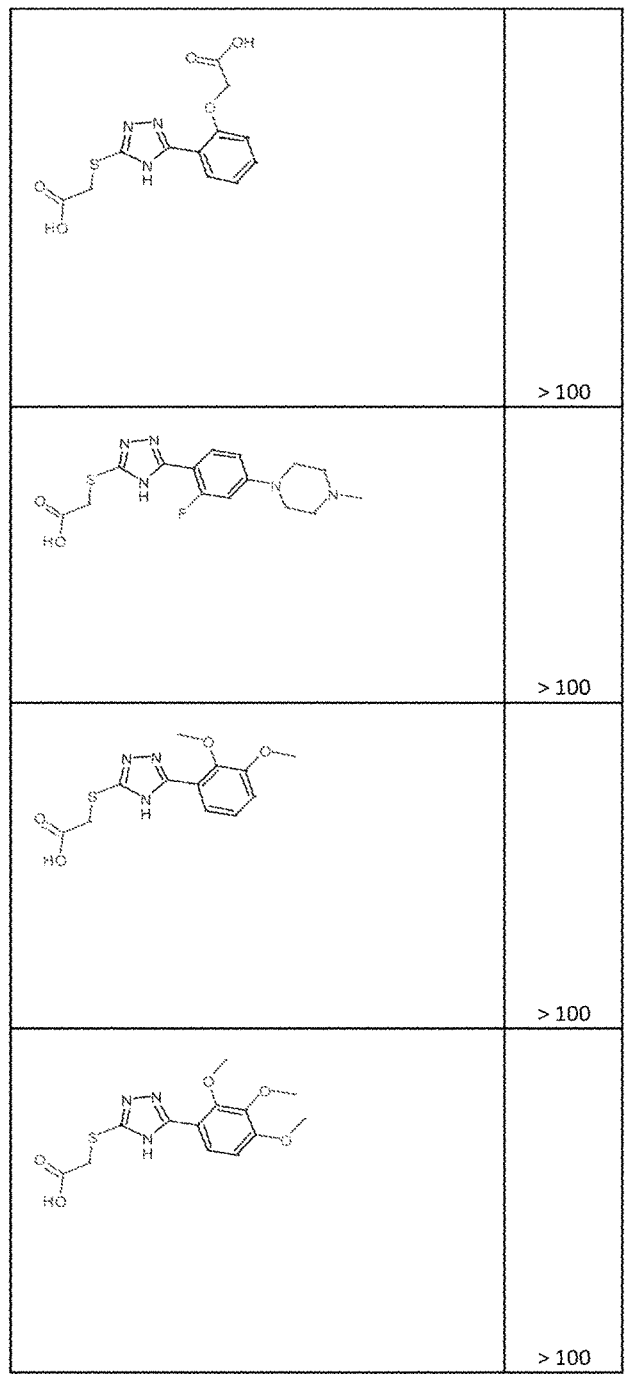
Figure 3:
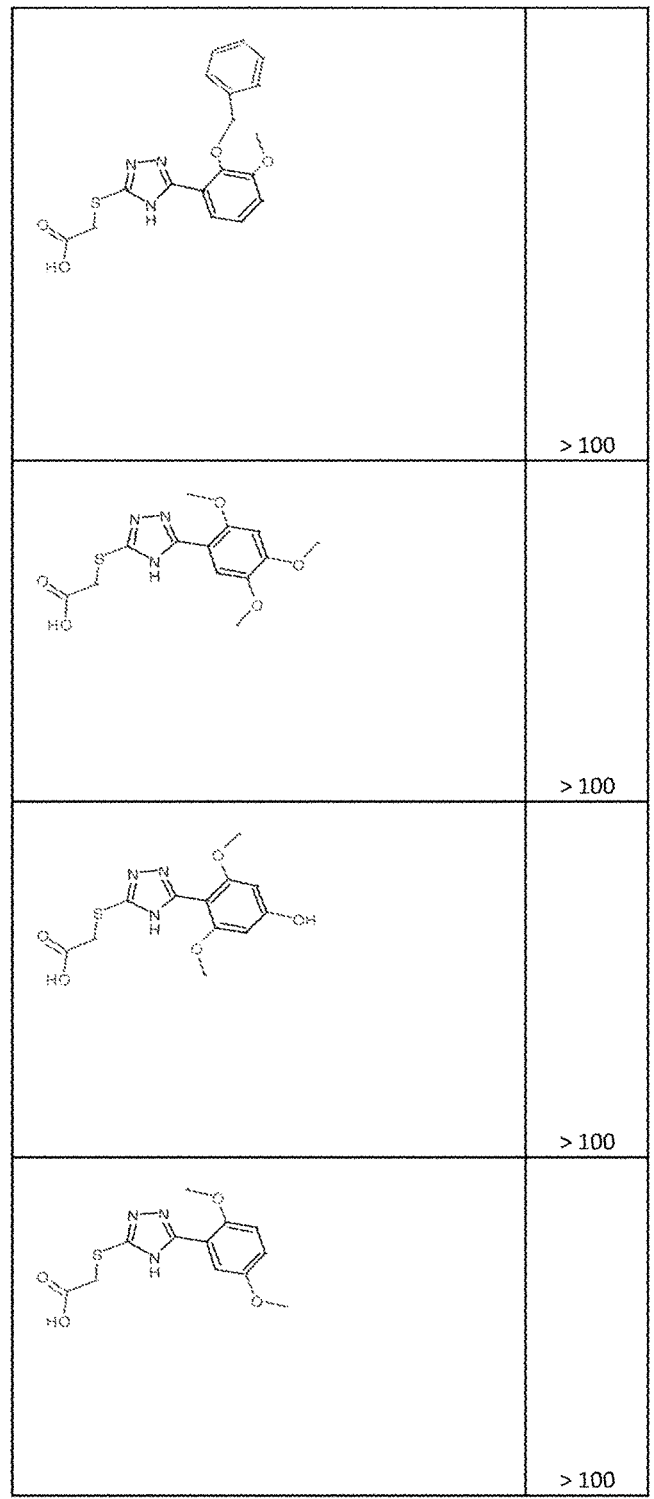
Figure 3:
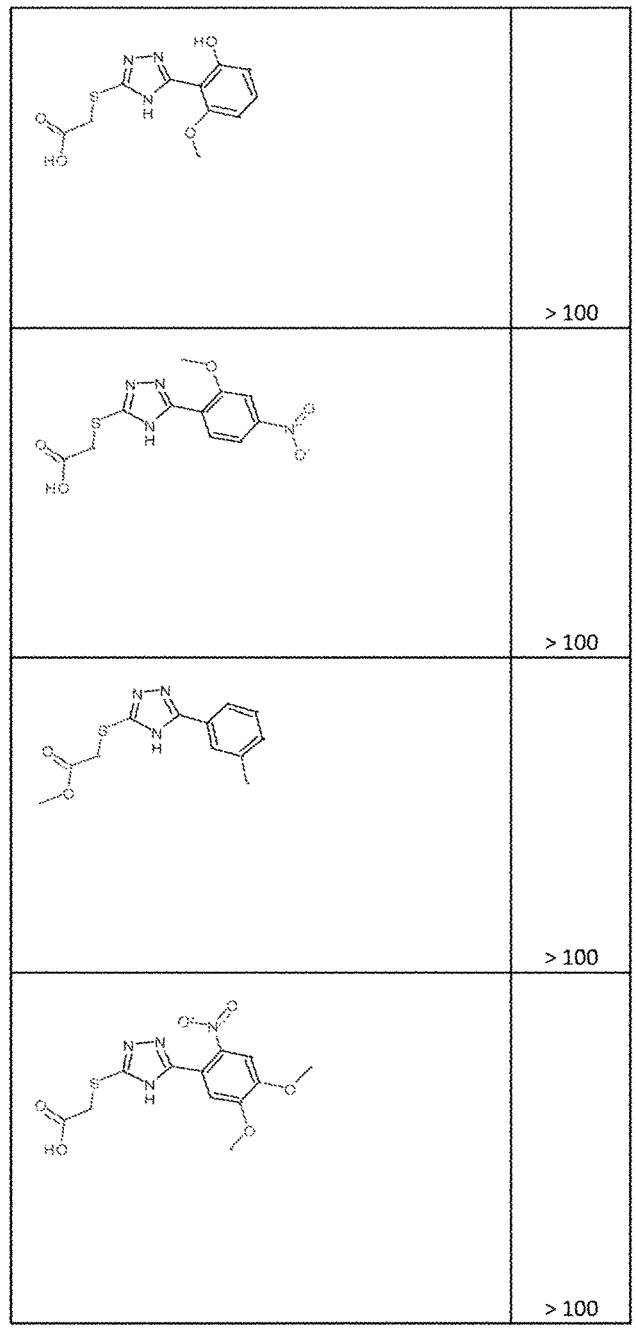
Figure 3:
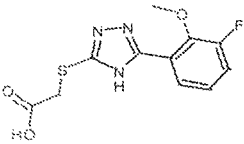
Figure 3:
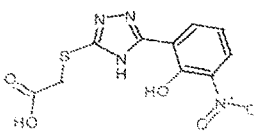
Figure 3:
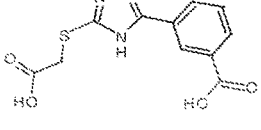
Figure 3:
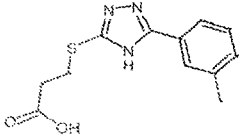
Figure 3:
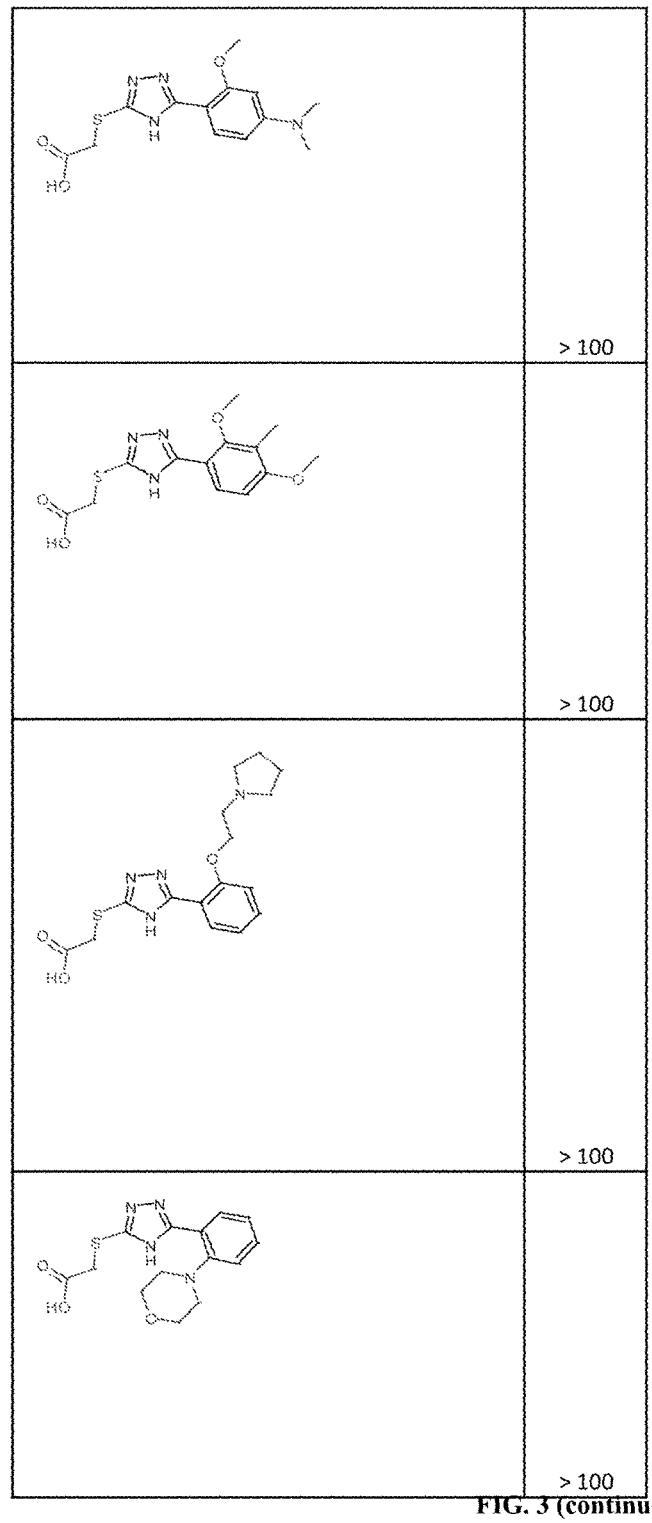
Figure 3:
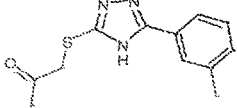
Figure 3:
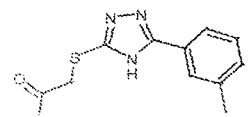
Figure 3:
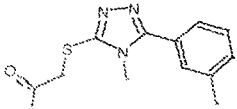
Figure 3:
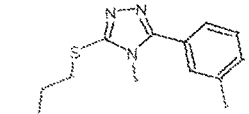
Figure 3:
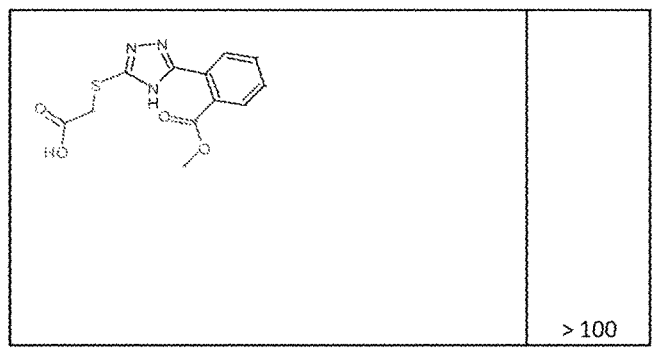

Results of the testing are shown in Table 2 and in FIG. 3.

TABLE 2

| Structure | IC$_{50}$ µM |
|---|---|
| (structure) | 7.05 |
| (structure) | 6.61 |
| (structure) | 40.62 |
| (structure) | 28.42 |
| (structure) | 8.44 |

TABLE 2-continued

| Structure | IC$_{50}$ µM |
|---|---|
| (structure) | 6.45 |
| (structure) | 7.11 |
| (structure) | 10.26 |
| (structure) | 6.75 |
| (structure) | 4.48 |
| (structure) | >60 |

TABLE 2-continued

| Structure | IC$_{50}$ μM |
|---|---|
| (phenoxymethyl-ethyl-triazole-S-CH2CH2-COOH) | >60 |
| (7-amino-4-(6-chloro-[1,3]dioxolo[4,5-g]quinolin-7-yl)-2-amino-3-cyano-4H-chromene) | 6.48 |
| (azepane-SO2-phenyl-SO2NH-phenyl-(5-methylfuran-2-yl)) | >60 |
| (azepane-SO2-phenyl-SO2NH-phenyl-tetrazole) | >60 |
| (HO-CH2CH2-N(C=S)-NH-Et with methylenedioxyquinolinone-CH2) | >60 |

TABLE 2-continued

| Structure | IC$_{50}$ μM |
|---|---|
| (dihydroxyphenyl-cycloheptafuranone with OEt and CH3 groups) | 4.41 |
| (2-thienyl-4H-chromene-3-carbonitrile-2,7-diamine) | 11.77 |
| (1,4-diamino-anthraquinone-2-carboxamide) | 12.65 |
| (piperidine-SO2-acenaphthylenone) | >60 |
| (4-(p-tolyl)-4H-chromene-3-carbonitrile-2,7-diamine) | 25.96 |

TABLE 2-continued

| Structure | IC$_{50}$ μM |
|---|---|
| (4-hydroxyphenyl phthalazine with acetamidoanilino structure) | >60 |
| (4-amino isothiazole carboxamide with phenyl and methoxyethyl amide) | >60 |
| (1,3-dimethyl-4-ethoxy cyclohepta[c]pyrrol-8(2H)-one) | 2.55 |
| (bis-morpholinopropyl iminomethyl binaphthalene with isopropyl and methyl groups) | 10.12 |

TABLE 2-continued

| Structure | IC$_{50}$ μM |
|---|---|
| (amino hydroxy lactone fused anthracenone) | 47 |
| (bis-morpholinopropylamino methylene binaphthoquinone with isopropyl and methyl groups) | 16.89 |
| (amino cyano diethylaminoethyl pyrido-indole) | 18.75 |
| (bis(5-hydroxy-3-methyl-1H-pyrazol-4-yl)methyl-(4-diethylaminophenyl)) | 9.93 |
| (ethyl 2-amino-1-cyclopropyl-pyrrolo[2,3-b]quinoxaline-3-carboxylate) | 2.83 |

TABLE 2-continued

| Structure | IC$_{50}$ μM |
|---|---|
| (5-bromo-indolin-2-one hydrazone linked to N-(2-ethylhexyl)benzamide) | >60 |
| (tetracycline-like structure with two dimethylamino groups, hydroxyls, and carboxamide) | 1.37 |
| (5,6,7-trihydroxy-2-phenyl-4H-chromen-4-one / baicalein) | 8.7 |
| (ribofuranosyl-amino-methyl-nitro-benzene derivative) | 11.95 |
| (cycloheptapyrrolone with 1,3-dimethyl, N-p-tolyl, and ethoxy substituents) | 3.4 |

TABLE 2-continued

| Structure | IC$_{50}$ μM |
|---|---|
| (7,8-dihydroxy-4-(4-methoxyphenyl)-2H-chromen-2-one) | 7.16 |
| (methyl 2-amino-1-allyl-1H-pyrrolo[2,3-b]quinoxaline-3-carboxylate) | 0.973 |
| (2-amino-1-butyl-1H-pyrrolo[2,3-b]quinoxaline-3-carbonitrile) | 1.56 |
| (methyl 2-amino-1-pentyl-1H-pyrrolo[2,3-b]quinoxaline-3-carboxylate) | 1.03 |

TABLE 2-continued
| Structure | IC$_{50}$ µM |
|---|---|
| (structure) | 1.44 |
| (structure) | 5.92 |
| (structure) | 4.6 |
| (structure) | >60 |
| (structure) | 17.81 |
| (structure) | 12.54 |
| (structure) | >60 |
Example 5—Preparation of 2-(5-(3-bromophenyl)-1H-1,2,4-triazol-3-yl)thio)acetic acid
Step 1: 5-(3-bromophenyl)-1H-1,2,4-triazole-3-thiol
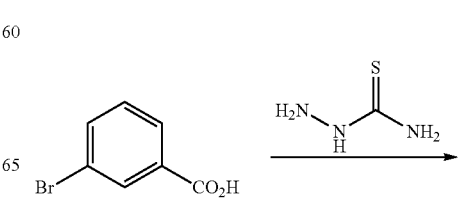

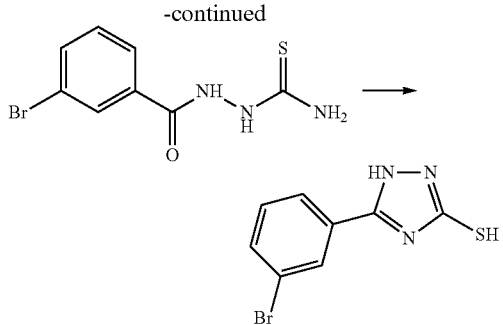

3-bromobenzoic acid (562 mg, 2.80 mmol) was converted into the corresponding acid chloride by dissolving in dichloromethane (6 ml) and treating with oxalyl chloride (0.28 ml, 3.26 mmol) and 10 μl of anhydrous dimethyl formamide. Upon cessation of the bubbling, the solution was briefly warmed at 35° C. and evaporated to dryness. The residue was dissolved in anhydrous pyridine (3 ml) and a solution of thiosemicarbazide (255 mg, 2.8 mmole) in pyridine (7 ml) was added at 0° C. and allowed to warm to room temperature and stirred overnight.

The mixture was heated for 4 h at 70° C., cooled, and evaporated to dryness. Sodium hydroxide solution (1M, 8 ml) was added and the mixture was stirred at 40° C. overnight at which time another 2 ml sodium hydroxide solution was added and heating continued at 70° C. for another 2.5 h. The solution was cooled, filtered and washed with water. After acidification with HCl (1M), the pure product precipitated, 448 mg (63% yield).

Step 2: Preparation of 2-((5-(3-bromophenyl)-1H-1,2,4-triazol-3-yl)thio)acetic acid

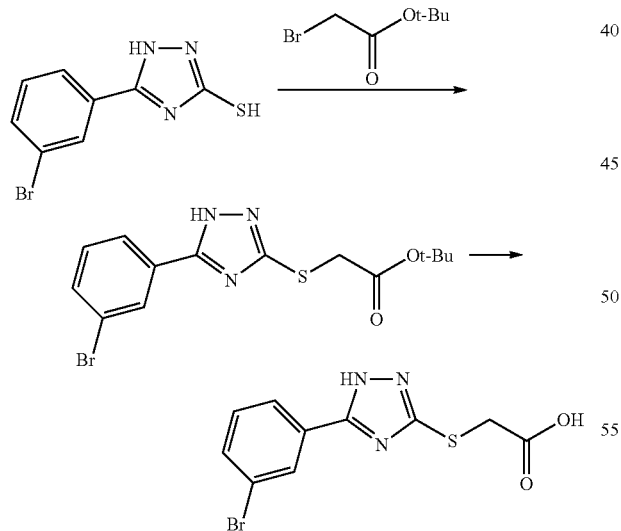

5-(3-bromophenyl)-1H-1,2,4-triazole-3-thiol (300 mg, 1.17 mmol) was dissolved in acetone (12 ml) and treated with t-butylbromoacetate (192 μl, 1.3 mmol). The mixture was heated at 40-50° C. for 90 m for a total of 4 h 20 m. The reaction mixture was cooled in ice and filtered. Evaporation to dryness gave a ca. 2:1 mixture of acid and ester which were separated by partitioning between ethyl acetate and sodium bicarbonate solution. Acidification of the aqueous layer afforded the pure acid in 67% yield.

Example 6—Preparation of 2-((5-(3'-chloro-5'-methoxy-[1,1'-biphenyl]-3-yl)-1H-1,2,4-triazol-3-yl)thio)acetic acid General Synthetic Scheme for Arylation:

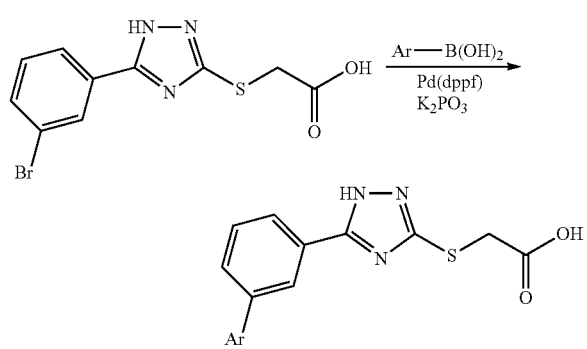

2-((5-(3-bromophenyl)-1H-1,2,4-triazol-3-yl)thio)acetic acid (20 mg, 0.063 mmol) was dissolve in anhydrous acetonitrile (1 ml) in a vial and (3-chloro-5-methoxyphenyl) boronic acid (28 mg), Pd(dppf)Cl$_2$ ([1,1'-Bis(diphenylphosphino)-ferrocene]dichloropalladium(II)), (5 mg) and K$_2$PO$_3$ solution (2M, 500 μl) were added. The vial was sealed and heated for 10 m in a microwave reactor at 150° C. The pure product was isolated by automated LC/MS purification upon evaporation to dryness.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting a G protein coupled receptor 6 kinase polypeptide in a patient, the method comprising administering to the patient a therapeutically effective amount of an inhibitor having Formula (4):

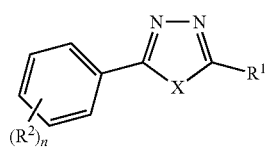

or a pharmaceutically acceptable salt form thereof, the inhibitor has an IC$_{50}$ of <100 μM in a G protein coupled receptor 6 kinase polypeptide inhibition assay,
wherein:
X is selected from the group consisting of NR$^5$ and O;
R$^1$ is selected from the group consisting of: NR$^3$R$^4$ and —S(CH$_2$)$_m$C(O)OH;
each R$^2$ is independently selected from the group consisting of: H, halo, (C$_1$-C$_6$)haloalkyl, —CN, —NR$^3$R$^4$, —O(C$_1$-C$_6$)haloalkyl, —OR$^3$, —OC(O)R$^3$, —C(O)R$^3$, —C(O)OR³, —C(O)NR³R⁴, —SR³, —SO₂R³, —SO₂NR³R⁴, (C₃-C₇) cycloalkyl, (C₃-C₇)heterocycloalkyl, (C₅-C₁₄)aryl, and unsubstituted (C₅-C₁₄)heteroaryl;

wherein the (C₅-C₁₄)aryl is optionally substituted with (C₁-C₆)alkyl, halo, (C₁₋₆)haloalkyl, —CN, —NR⁸R⁹, —NO₂, —O(C₁-C₆)haloalkyl, —OC(O)R⁸, —C(O)R⁸, —C(O)OR⁸, —C(O)NR⁸R⁹, —S(O)R⁸, —SO₂R⁸, —SO₂NR⁸R⁹, (C₃-C₇)cycloalkyl, (C₃-C₇)heterocycloalkyl, (C₅-C₁₄)aryl, (C₁-C₆) alkyl, wherein R⁸ and R⁹ are independently selected from H and or (C₅-C₁₄)heteroaryl;

R³ and R⁴ are independently selected from the group consisting of: H, or (C₁-C₆)alkyl (C₃-C₇) cycloalkyl, (C₃-C₇)heterocycloalkyl, (C₅-C₁₄)aryl, and (C₅-C₁₄) heteroaryl;

R⁵ is H;

m is an integer from 1 to 2; and n is an integer from 1 to 5.

2. The method of claim 1, wherein R² is selected from the group consisting of: (C₁-C₆)haloalkyl, —CN, —OR³, —OC(O)R³, C(O)R³, —C(O)OR³, —SR³, —SO₂R³, —SO₂NR³R⁴, (C₅-C₁₄)aryl, and unsubstituted (C₅-C₁₄)heteroaryl.

3. The method of claim 1, wherein X is NH.

4. The method of claim 1, wherein n is 1.

5. The method of claim 1, wherein R¹ is —S(CH₂)ₘC(O)OH.

6. The method of claim 1, wherein the inhibitor of Formula (4) is an inhibitor having Formula (4-1):

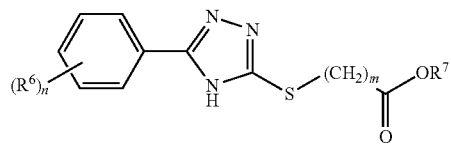

or a pharmaceutically acceptable salt form thereof, wherein:

R³ and R⁴ are independently selected from the group consisting of: H, (C₃-C₇) cycloalkyl, (C₃-C₇)heterocycloalkyl, (C₅-C₁₄)aryl, and (C₅-C₁₄)heteroaryl;

R⁶ is independently selected from the group consisting of H, C₁-C₆)haloalkyl, —CN, —NR³R⁴, —O(C₁-C₆)haloalkyl, —OR³, —OC(O)R³, —C(O)R³, —C(O)OR³, —C(O)NR³R⁴, —SR³, —SO₂R³, —SO₂NR³R⁴, (C₃-C₇) cycloalkyl, (C₃-C₇)heterocycloalkyl, (C₅-C₁₄)aryl, and unsubstituted (C₅-C₁₄)heteroaryl;

wherein the (C₅-C₁₄)aryl is optionally substituted with (C₁-C₆)alkyl, halo, (C₁₋₆)haloalkyl, —CN, —NR⁸R⁹, —NO₂, —O(C₁-C₆)haloalkyl, —OC(O)R⁸, —C(O)R⁸, —C(O)OR⁸, —C(O)NR⁸R⁹, —SR⁸, —S(O)R⁸, —SO₂R⁸, —SO₂NR⁸R⁹, (C₃-C₇)cycloalkyl, (C₃-C₇)heterocycloalkyl, (C₅-C₁₄)aryl, or (C₅-C₁₄)heteroaryl, wherein R⁸ and R⁹ are independently selected from H or (C₁-C₆)alkyl R⁷ is H;

m is an integer from 1 to 2; and n is an integer from 1 to 3.

7. The method of claim 6, wherein R⁶ is selected from the group consisting of: —OR³, —O(C₁-C₆)haloalkyl, and unsubstituted (C₅-C₁₄)heteroaryl.

8. The method of claim 1, wherein the inhibitor having Formula (4) is selected from the group consisting of:

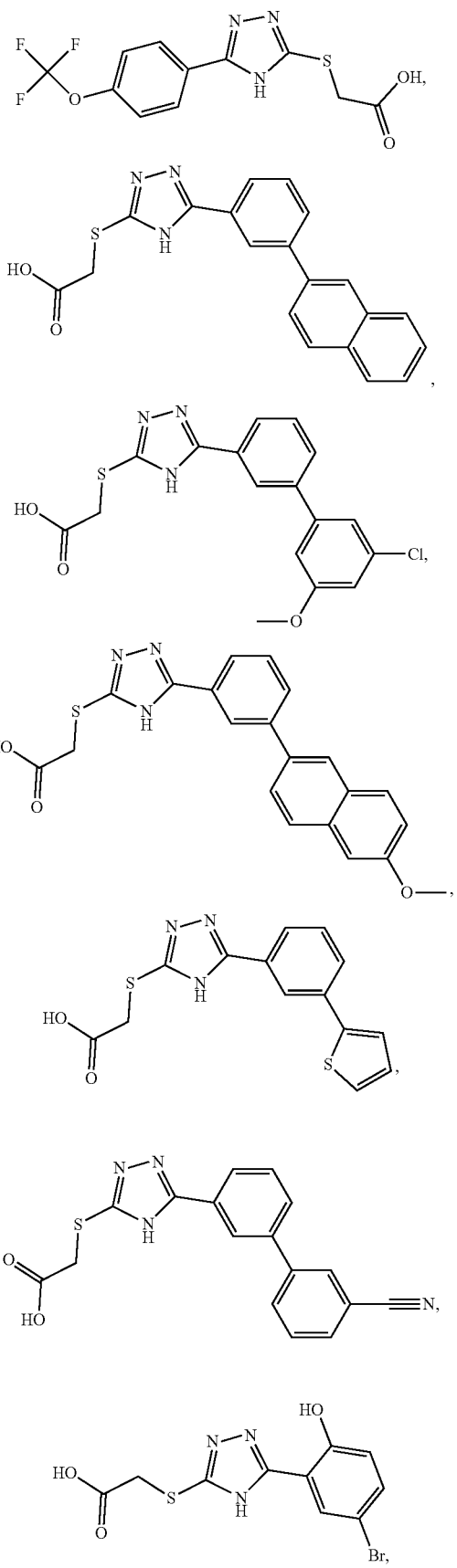

-continued
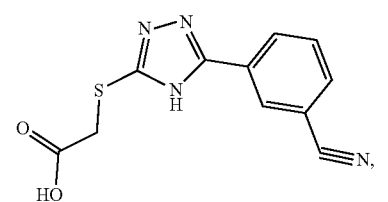
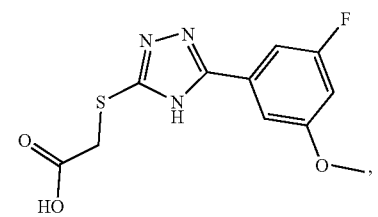
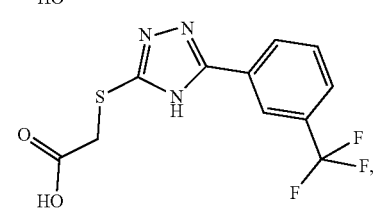
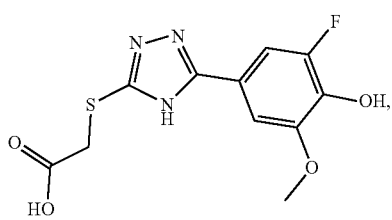
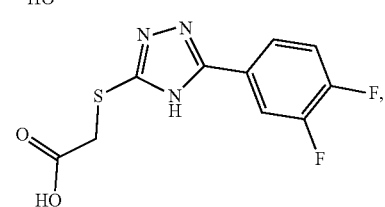
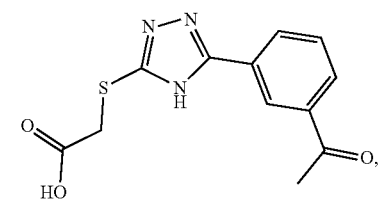
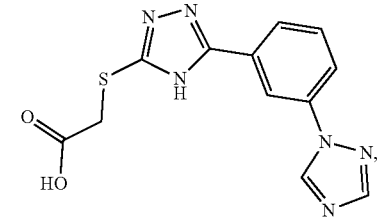
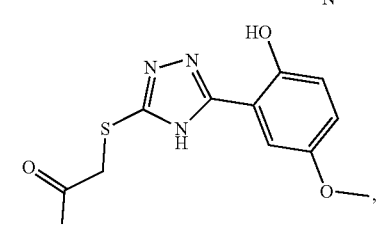
-continued
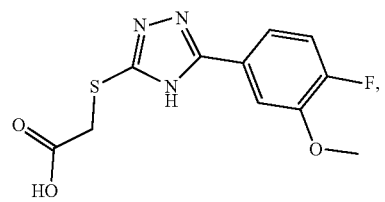
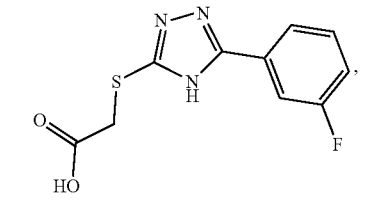
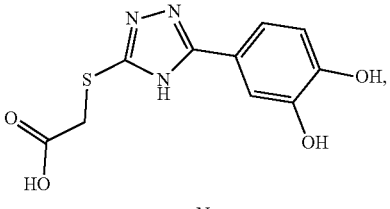
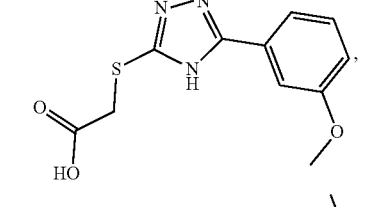
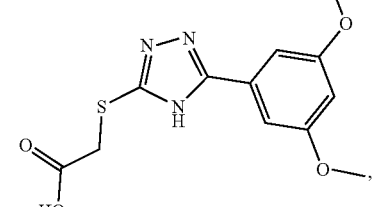
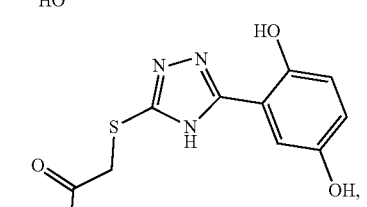
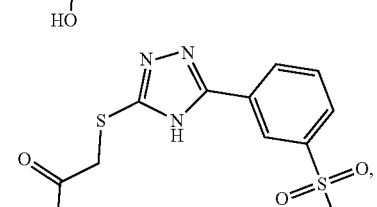
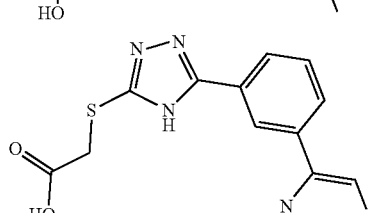

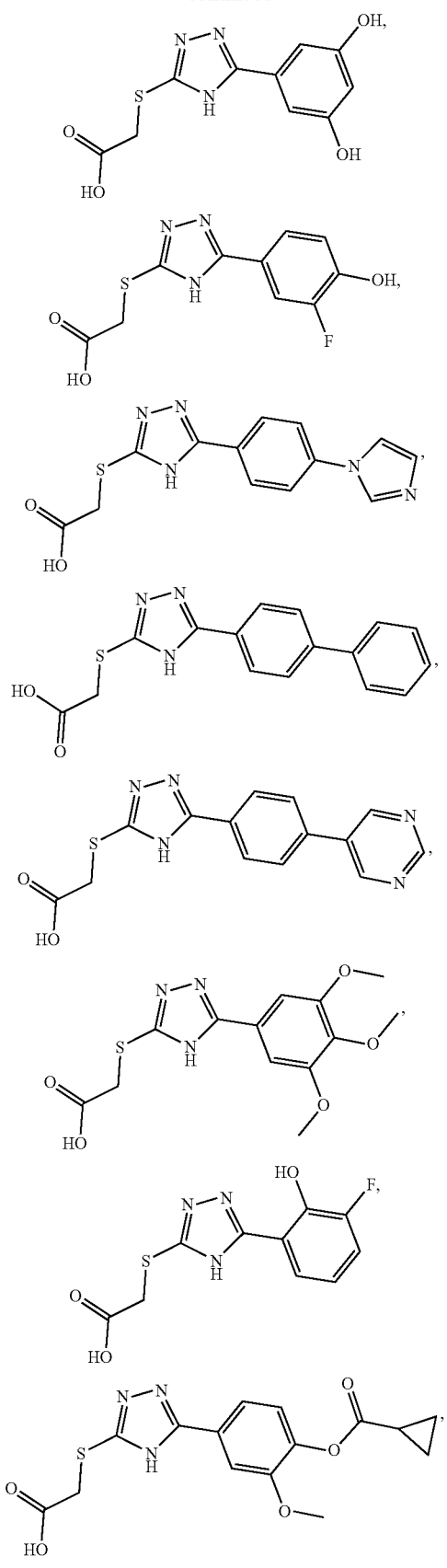
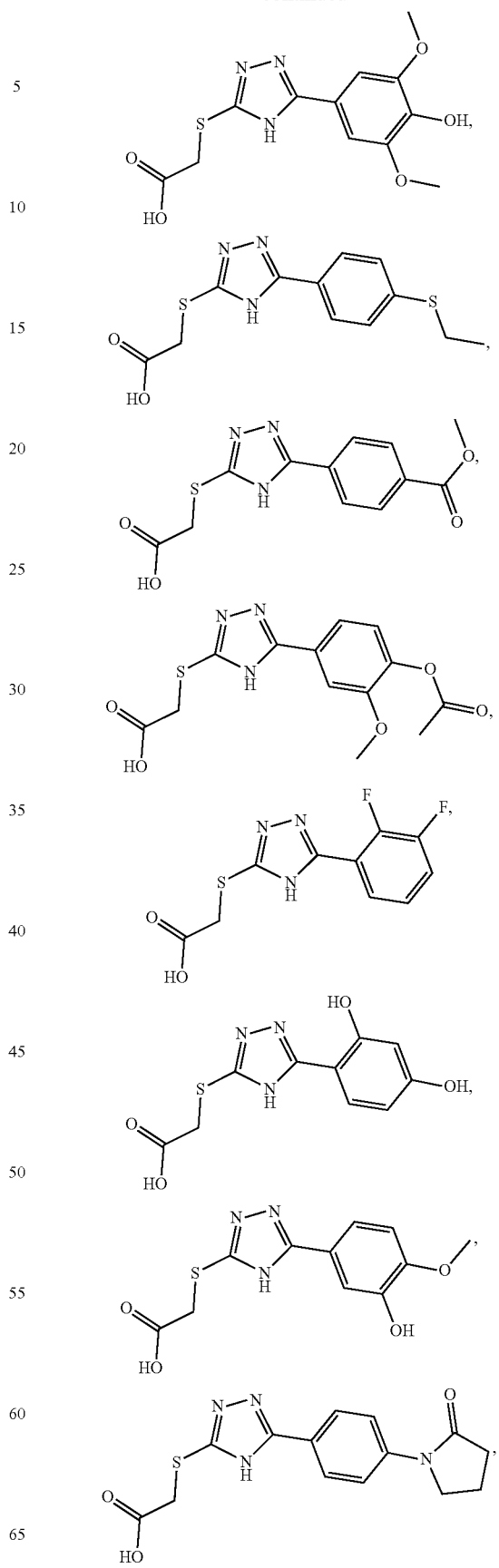

-continued
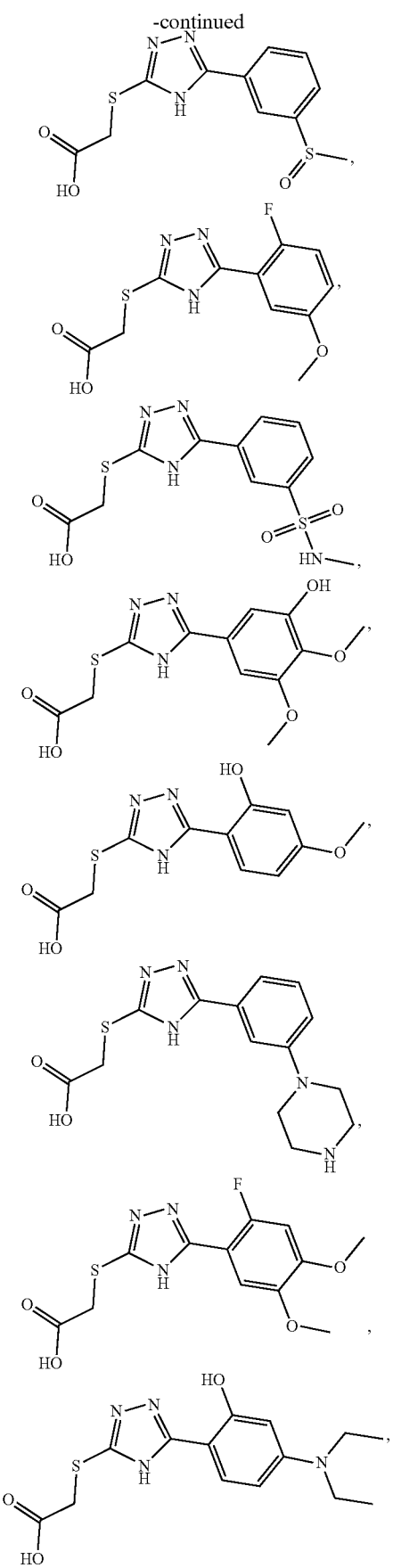
-continued
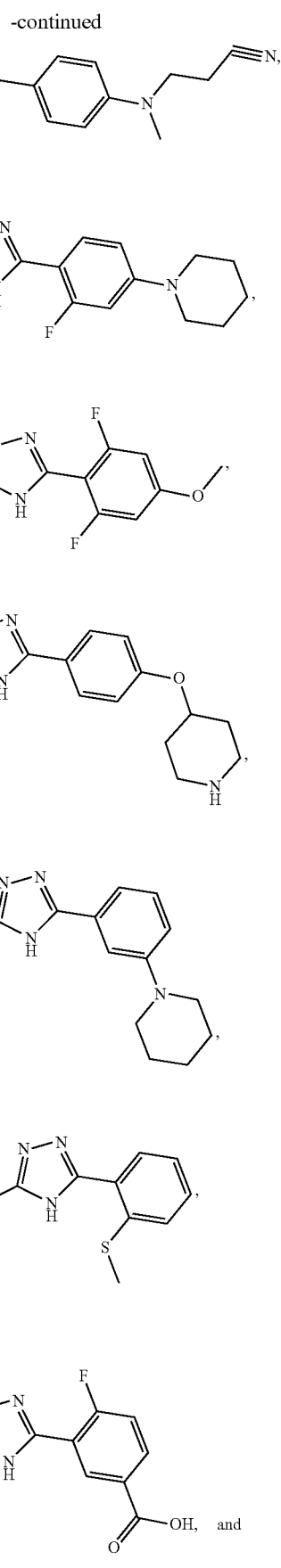

-continued

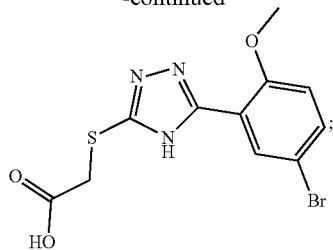

or a pharmaceutically acceptable salt form thereof.

9. A method for inhibiting a G protein coupled receptor 6 kinase polypeptide in a cell, the method comprising contacting the cell with an effective amount of an inhibitor having Formula (4):

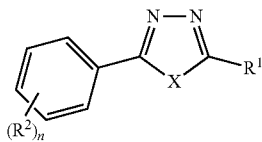

or a pharmaceutically acceptable salt form thereof, the inhibitor has an $IC_{50}$ of <100 μM in a G protein coupled receptor 6 kinase polypeptide inhibition assay,
wherein:
X is selected from the group consisting of $NR^5$;
$R^1$ is selected from the group consisting of: $-NR^3R^4$ and $-SCH_2C(O)OR^3$;
$R^2$ is selected from substituted or unsubstituted $(C_5-C_{14})$ aryl and unsubstituted $(C_5-C_{14})$heteroaryl;
wherein the $(C_5-C_{14})$aryl is optionally substituted with $(C_1-C_6)$alkyl, halo, $(C_1-6)$haloalkyl, —CN, $-NR^8R^9$, $-NO_2$, $-O(C_1-C_6)$haloalkyl, —OC(O)$R^8$, —C(O)$R^8$, —C(O)O$R^8$, —C(O)N$R^8R^9$, —S$R^8$, —S(O)$R^8$, —SO$_2R^8$, —SO$_2NR^8R^9$, $(C_3-C_7)$cycloalkyl, $(C_3-C_7)$heterocycloalkyl, $(C_5-C_{14})$aryl, or $(C_5-C_{14})$heteroaryl, wherein $R^8$ and $R^9$ are independently selected from H or $(C_1-C_6)$alkyl;
$R^3$ and $R^4$ are independently selected from the group consisting of: H and substituted or unsubstituted $(C_1-C_6)$alkyl; and
$R^5$ is H.

10. The method of claim 9, wherein the cell is a cancerous cell.

11. The method of claim 10, wherein the cancerous cell is a B cell cancerous cell.

12. A method for ameliorating or reducing one or more symptoms of a hematological malignancy in a patient, the method comprising administering to the patient in need thereof a therapeutically effective amount of an inhibitor having Formula (4):

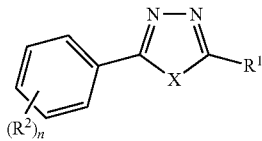

or a pharmaceutically acceptable salt form thereof, the inhibitor has an $IC_{50}$ of <100 μM in a G protein coupled receptor 6 kinase polypeptide inhibition assay,
wherein:
X is selected from the group consisting of $NR^5$ and O;
$R^1$ is selected from the group consisting of: $-NR^3R^4$, and $-S(CH_2)_mC(O)OH$;
each $R^2$ is independently selected from the group consisting of: H, halo, $(C_1-C_6)$haloalkyl, —CN, $-NR^3R^4$, $-O(C_1-C_6)$haloalkyl, $-OR^3$, —OC(O)$R^3$, —C(O)$R^3$, —C(O)O$R^3$, —C(O)N$R^3R^4$, —S$R^3$, —SO$_2R^3$, —SO$_2NR^3R^4$, $(C_3-C_7)$ cycloalkyl, $(C_3-C_7)$heterocycloalkyl, $(C_5-C_{14})$aryl, and unsubstituted $(C_5-C_{14})$heteroaryl;
$R^3$ and $R^4$ are independently selected from the group consisting of: H, $(C_1-C_6)$alkyl, $(C_3-C_7)$ cycloalkyl, $(C_3-C_7)$heterocycloalkyl, $(C_5-C_{14})$aryl, and $(C_5-C_{14})$ heteroaryl;
$R^5$ is selected from the group consisting of: H and $(C_1-C_6)$alkyl;
m is an integer from 1 to 2; and
n is an integer from 1 to 5.

13. The method of claim 12, wherein the hematological malignancy is a B cell cancer.

14. The method of claim 13, wherein the B cell cancer is selected from the group consisting of: a small lymphocytic lymphoma (SLL), a mantle cell lymphoma, a Burkitt's lymphoma, a follicle centre cell lymphoma, a follicular lymphoma, a Burkitt-like lymphoma, a marginal zone B-cell lymphoma (MZBCL), a nodal marginal zone B cell lymphoma, an extra-nodal marginal zone B cell lymphoma, a splenic marginal zone B cell lymphoma, a lymphoplasmacytic lymphoma, and a diffuse large B cell lymphoma.

15. The method of claim 13, wherein the B cell cancer is selected from the group consisting of: a B cell acute lymphocytic leukemia (B-ALL), a precursor B cell acute lymphocytic leukemia (B-ALL), a B cell chronic lymphocytic leukemia (B-CLL), a precursor B-lymphoblastic leukaemia, a precursor B-lymphoblastic lymphoma, a small lymphocytic lymphoma, a B cell prolymphocytic leukemia, an undifferentiated B cell lymphoma, a hairy cell leukemia, a mediastinal large B-cell lymphoma, a plasma cell myeloma, a plasmacytoma, a primary effusive lymphoma, a Burkitt's cell leukemia, and a B cell diffuse mixed lymphoma.

16. A method for ameliorating or reducing one or more symptoms of an inflammatory disease in a patient in need thereof, the method comprising administering to the patient a therapeutically effective amount of an inhibitor having Formula (4):

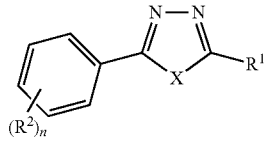

or a pharmaceutically acceptable salt form thereof, the inhibitor has an $IC_{50}$ of <100 μM in a G protein coupled receptor 6 kinase polypeptide inhibition assay,
wherein:
X is selected from the group consisting of $NR^5$ and O;
$R^1$ is selected from the group consisting of: $-NR^3R^4$, and $-S(CH_2)_mC(O)OH$;
each $R^2$ is independently selected from the group consisting of: H, halo $(C_1-C_6)$haloalkyl, —CN, $-NR^3R^4$, $-O(C_1-C_6)$haloalkyl, $-OR^3$, —OC(O)$R^3$, —C(O)$R^3$, —C(O)O$R^3$, —C(O)N$R^3R^4$, —S$R^3$, —SO$_2R^3$, —SO$_2$NR$^3$R$^4$, (C$_3$-C$_7$) cycloalkyl, (C$_3$-C$_7$)heterocycloalkyl, (C$_5$-C$_{14}$)aryl, and unsubstituted (C$_5$-C$_{14}$)heteroaryl;

wherein the (C$_5$-C$_{14}$)aryl is optionally substituted with (C$_1$-C$_6$)alkyl, halo, (C$_{1-6}$)haloalkyl, —CN, —NR$^8$R$^9$, —NO$_2$, —O(C$_1$-C$_6$)haloalkyl, —OR$^8$, —OC(O)R$^8$, —C(O)R$^8$, —C(O)OR$^8$, —C(O)NR$^8$R$^9$, —SR$^8$, —S(O)R$^8$, —SO$_2$R$^8$, —SO$_2$NR$^8$R$^9$, (C$_3$-C$_7$)cycloalkyl, (C$_3$-C$_7$)heterocycloalkyl, (C$_5$-C$_{14}$)aryl, or (C$_5$-C$_{14}$)heteroaryl, wherein R$^8$ and R$^9$ are independently selected from H or (C$_1$-C$_6$)alkyl;

R$^3$ and R$^4$ are independently selected from the group consisting of: H, (C$_1$-C$_6$)alkyl, (C$_3$-C$_7$) cycloalkyl, (C$_3$-C$_7$)heterocycloalkyl, (C$_5$-C$_{14}$)aryl, and (C$_5$-C$_{14}$)heteroaryl;

R$^5$ is H;

m is an integer from 1 to 2; and n is an integer from 1 to 5.

17. The method of claim 16, wherein the inflammatory disease is selected from the group consisting of: encephalitis, inflammatory eye disease, otitis, pharyngitis, pneumonia, gastritis, enteritis, hepatitis, pancreatitis, nephritis, cystitis, urethritis, endometritis, vaginitis, arthritis, peripheral neuritis, malignant tumor, infectious diseases, autoimmune diseases, ischemic diseases, metabolic diseases, injury, scald, chemical corrosion, and neurodegenerative diseases.

18. The method of claim 17, wherein the autoimmune diseases are selected from the group consisting of: rheumatism, systemic lupus erythematosus, and sarcoidosis.

19. The method of claim 17, wherein the ischemic diseases are selected from the group consisting of: myocardial infarction and cerebral infarction.

20. The method of claim 17, wherein the metabolic diseases are selected from the group consisting of: diabetes and gout.

21. The method of claim 17, wherein the neurodegenerative disease is Alzheimer's.

22. A method of suppressing an immune response in a patient, the method comprising administering to the patient a therapeutically effective amount of an inhibitor having Formula (4):

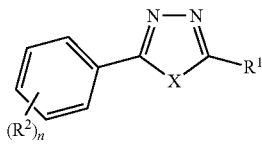

or a pharmaceutically acceptable salt form thereof, the inhibitor has an IC$_{50}$ of <100 µM in a G protein coupled receptor 6 kinase polypeptide inhibition assay, wherein:

X is selected from the group consisting of NR$^5$ and O;

R$^1$ is selected from the group consisting of: —NR$^3$R$^4$, and —S(CH$_2$)$_m$C(O)OH;

each R$^2$ is independently selected from the group consisting of: H, halo, (C$_1$-C$_6$)haloalkyl, —CN, —NR$^3$R$^4$, —O(C$_1$-C$_6$)haloalkyl, —OR$^3$, —OC(O)R$^3$, —C(O)R$^3$, —C(O)OR$^3$, —C(O)NR$^3$R$^4$, SR$^3$, —SO$_2$R$^3$, —SO$_2$NR$^3$R$^4$, (C$_3$-C$_7$) cycloalkyl, (C$_3$-C$_7$)heterocycloalkyl, (C$_5$-C$_{14}$)aryl, and unsubstituted (C$_5$-C$_{14}$)heteroaryl;

wherein the (C$_5$-C$_{14}$)aryl is optionally substituted with (C$_1$-C$_6$)alkyl, halo, (C$_{1-6}$)haloalkyl, —CN, —NR$^8$R$^9$, —NO$_2$, —O(C$_1$-C$_6$)haloalkyl, —OC(O) R$^8$, —C(O)R$^8$, —C(O)OR$^8$, —C(O)NR$^8$R$^9$, —SR$^8$, —S(O)R$^8$, —SO$_2$R$^8$, —SO$_2$NR$^8$R$^9$, (C$_3$-C$_7$)cycloalkyl, (C$_3$-C$_7$)heterocycloalkyl, (C$_5$-C$_{14}$)aryl, or (C$_5$-C$_{14}$)heteroaryl, wherein R$^8$ and R$^9$ are independently selected from H or (C$_1$-C$_6$)alkyl;

R$^3$ and R$^4$ are independently selected from the group consisting of: H, (C$_1$-C$_6$)alkyl (C$_3$-C$_7$) cycloalkyl, (C$_3$-C$_7$)heterocycloalkyl, (C$_5$-C$_{14}$)aryl, and (C$_5$-C$_{14}$)heteroaryl;

R$^5$ is H;

m is an integer from 1 to 2; and n is an integer from 1 to 5.

23. A method for inhibiting a G protein coupled receptor 6 kinase polypeptide in a patient, the method comprising administering to the patient a therapeutically effective amount of an inhibitor selected from the group consisting of

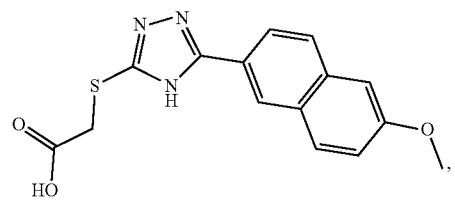

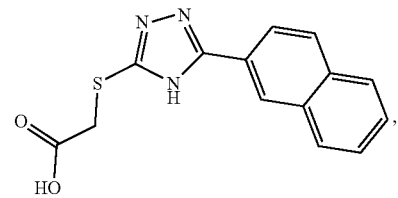

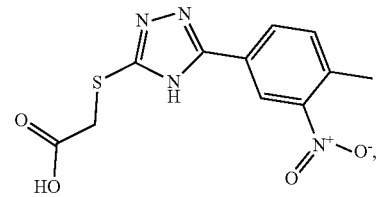

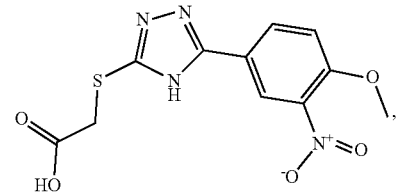

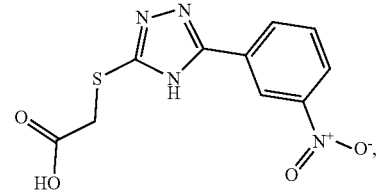

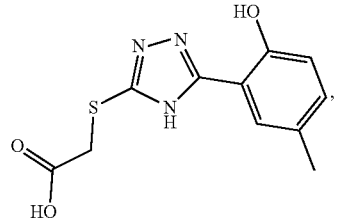

-continued

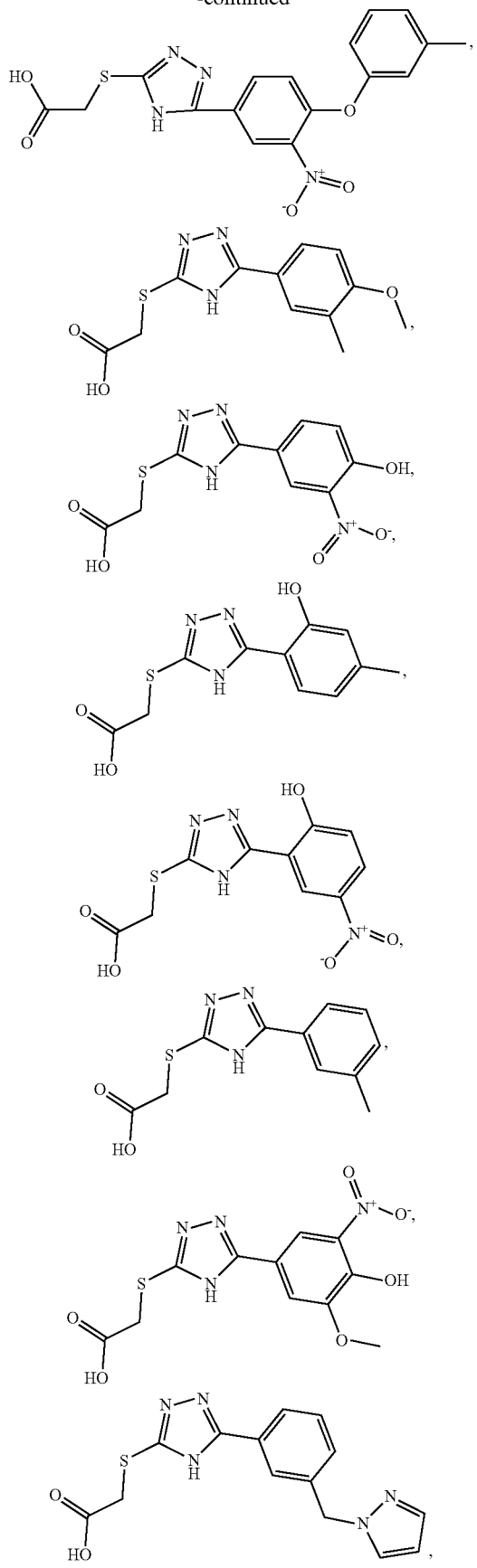

-continued

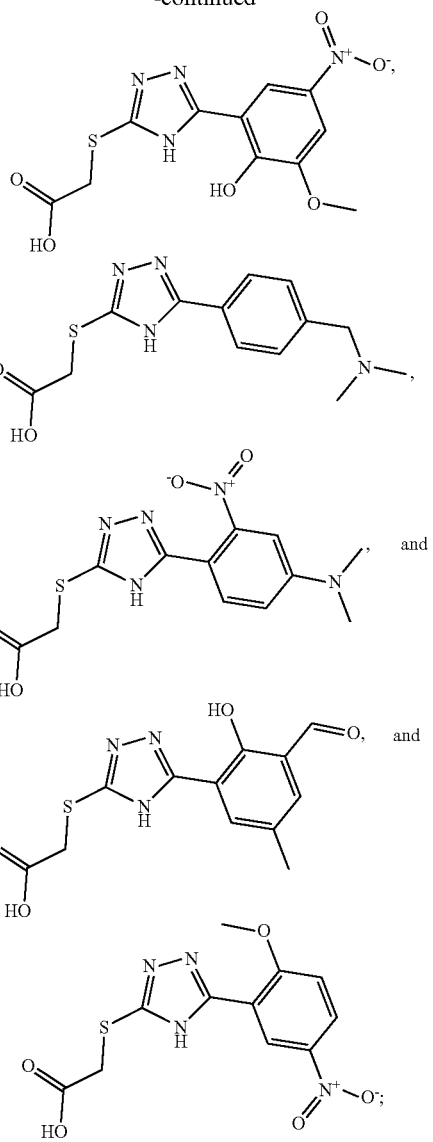

or a pharmaceutically acceptable salt form thereof the inhibitor has an IC$_{50}$ of <100 μM in a G protein coupled receptor 6 kinase polypeptide inhibition assay.

24. The method of claim 1, wherein R$^2$ is independently selected from the group consisting of: H, (C$_1$-C$_6$)haloalkyl, —CN, —O(C$_1$-C$_6$)haloalkyl, —OR$^3$, —OC(O)R$^3$, —C(O)R$^3$, —C(O)OR$^3$, —C(O)NR$^3$R$^4$, —SR$^3$, —SO$_2$R$^3$, —SO$_2$NR$^3$R$^4$, (C$_3$-C$_7$) cycloalkyl, (C$_3$-C$_7$)heterocycloalkyl, (C$_5$-C$_{14}$)aryl, and unsubstituted (C$_5$-C$_{14}$)heteroaryl.

25. The method of claim 12, wherein R$^2$ is independently selected from the group consisting of: H, halo, (C$_1$-C$_6$) haloalkyl, —CN, —NR$^3$R$^4$, —O(C$_1$-C$_6$)haloalkyl, —OR$^3$, —OC(O)R$^3$, —C(O)R$^3$, —C(O)OR$^3$, —C(O)NR$^3$R$^4$, —SR$^3$, —SO$_2$R$^3$, —SO$_2$NR$^3$R$^4$, (C$_3$-C$_7$) cycloalkyl, (C$_3$-C$_7$)heterocycloalkyl, (C$_5$-C$_{14}$)aryl, and unsubstituted (C$_5$-C$_{14}$)heteroaryl.

26. The method of claim 16, wherein R$^2$ is independently selected from the group consisting of: H, (C$_1$-C$_6$)haloalkyl, —CN, —NR$^3$R$^4$, —O(C$_1$-C$_6$)haloalkyl, —OR$^3$, —OC(O)R$^3$, —C(O)R$^3$, —C(O)OR$^3$, —C(O)NR$^3$R$^4$, —SR$^3$, —SO$_2$R$^3$, —SO$_2$NR$^3$R$^4$, (C$_3$-C$_7$) cycloalkyl, (C$_3$-C$_7$)heterocycloalkyl, (C$_5$-C$_{14}$)aryl, and unsubstituted (C$_5$-C$_{14}$)heteroaryl.

27. The method of claim 22, wherein R$^2$ is independently selected from the group consisting of: H, (C$_1$-C$_6$)haloalkyl, —CN, —NR$^3$R$^4$, —O(C$_1$-C$_6$)haloalkyl, —OR$^3$, —OC(O)R$^3$, —C(O)R$^3$, —C(O)OR$^3$, —C(O)NR$^3$R$^4$, —SR$^3$, —SO$_2$R$^3$, —SO$_2$NR$^3$R$^4$, (C$_3$-C$_7$) cycloalkyl, (C$_3$-C$_7$)heterocycloalkyl, (C$_5$-C$_{14}$)aryl, and unsubstituted (C$_5$-C$_{14}$)heteroaryl.

28. The method of claim 23, wherein the inhibitor is

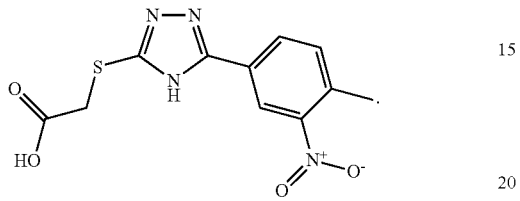

* * * * *

UNITED STATES PATENT AND TRADEMARK OFFICE
CERTIFICATE OF CORRECTION

PATENT NO. : 10,252,984 B2
APPLICATION NO. : 14/354326
DATED : April 9, 2019
INVENTOR(S) : Alexander Keith Stewart et al.

It is certified that error appears in the above-identified patent and that said Letters Patent is hereby corrected as shown below:

In the Claims

Column 86, Line 63, Claim 1, delete "$NR_3R_4$" and insert -- —$NR_3R_4$ --;

Column 87, Line 7, Claim 1, after "haloalkyl," insert -- —$OR^8$, --;

Column 87, Line 8, Claim 1, after "$C(O)NR_8R_9$," insert -- —$SR^8$, --;

Column 87, Lines 10-11 (Approx.), Claim 1, delete "$(C_1-C_6)$alkyl," and insert
-- or $(C_5-C_{14})$heteroaryl, --;

Column 87, Line 12, Claim 1, delete "$(C_5-C_{14})$heteroaryl;" and insert -- $(C_1-C_6)$alkyl; --;

Column 87, Line 15, Claim 1, delete "or $(C_1-C_6)$alkyl" and insert -- $(C_1-C_6)$alkyl, --;

Column 87, Line 47, Claim 6, delete "$C_1-C_6)$haloalkyl," and insert -- $(C_1-C_6)$haloalkyl, --;

Column 87, Line 54, Claim 6, after "haloalkyl," insert -- —$OR^8$, --;

Column 87, Line 59, Claim 1, delete "$(C_1-C_6)$alkyl" and insert -- $(C_1-C_6)$alkyl; --;

Column 95, Line 36, Claim 9, delete "$(C_{1-6})$haloalkyl," and insert -- $(C_1-C_6)$haloalkyl, --;

Column 95, Line 37, Claim 9, after "haloalkyl," insert -- —$OR^8$, --;

Column 96, Line 65, Claim 16, delete "halo" and insert -- halo, --;

Column 97, Line 61, Claim 22, delete "$SR^3$," and insert -- —$SR^3$, --;

Column 97, Line 67, Claim 22, after "haloalkyl," insert -- —$OR^8$, --;

Signed and Sealed this
Nineteenth Day of April, 2022

*Katherine Kelly Vidal*

Katherine Kelly Vidal
*Director of the United States Patent and Trademark Office*

CERTIFICATE OF CORRECTION (continued)
U.S. Pat. No. 10,252,984 B2

Column 98, Line 7, Claim 22, delete "$(C_1-C_6)$alkyl" and insert -- $(C_1-C_6)$alkyl, --;

Column 100, Line 22 (Approx.), Claim 23, delete "and";

Column 100, Line 47, Claim 23, delete "thereof" and insert -- thereof, --;

Column 100, Line 52, Claim 24, after "—CN," insert -- —$NR_3R_4$ --.